US012698268B2

(12) United States Patent
Liu et al.

(10) Patent No.: US 12,698,268 B2
(45) Date of Patent: Aug. 4, 2026

(54) DIHYDROISOQUINOLINONE AND ISOINDOLINONE DERIVATIVES AND USES THEREOF

(71) Applicant: Tarapeutics Science Inc., Bengbu (CN)

(72) Inventors: Qingsong Liu, Hefei (CN); Jing Liu, Hefei (CN); Yun Wu, Hefei (CN); Beilei Wang, Hefei (CN); Aoli Wang, Hefei (CN); Chen Hu, Hefei (CN); Qingwang Liu, Hefei (CN); Fengming Zou, Hefei (CN); Wenchao Wang, Hefei (CN); Zuowei Wang, Hefei (CN); Jiangyan Cao, Hefei (CN); Chenliang Shi, Hefei (CN); Li Wang, Hefei (CN)

(73) Assignee: Tarapeutics Science Inc., Bengbu (CN)

( * ) Notice: Subject to any disclaimer, the term of this patent is extended or adjusted under 35 U.S.C. 154(b) by 544 days.

(21) Appl. No.: 18/038,126

(22) PCT Filed: Oct. 21, 2021

(86) PCT No.: PCT/CN2021/125280

§ 371 (c)(1),
(2) Date: May 22, 2023

(87) PCT Pub. No.: WO2022/105526

PCT Pub. Date: May 27, 2022

(65) Prior Publication Data

US 2023/0416221 A1 Dec. 28, 2023

(30) Foreign Application Priority Data

Nov. 20, 2020 (CN) ........................ 202011308146.4

(51) Int. Cl.

*C07D 401/04* (2006.01)
*A61P 35/00* (2006.01)
*C07D 401/14* (2006.01)
*C07D 403/04* (2006.01)

(52) U.S. Cl.

CPC ............ *C07D 401/04* (2013.01); *A61P 35/00* (2018.01); *C07D 401/14* (2013.01); *C07D 403/04* (2013.01)

(58) Field of Classification Search

CPC .. C07D 401/04; C07D 401/14; C07D 403/04; A61P 35/00
USPC .......................................................... 514/218
See application file for complete search history.

(56) References Cited

FOREIGN PATENT DOCUMENTS

| | | | | |
|---|---|---|---|---|
| CN | 101031539 A | 9/2007 | | |
| CN | 102762548 A | 10/2012 | | |
| CN | 108727363 A | 11/2018 | | |
| CN | 111377907 A | 7/2020 | | |
| CN | 113264920 A | 8/2021 | | |
| JP | 2018-532737 A | 11/2018 | | |
| RU | 2 573 569 C2 | 1/2014 | | |
| WO | 2005074643 A2 | 8/2005 | | |
| WO | 2013/037896 A1 | 3/2013 | | |
| WO | 2014/160017 A1 | 10/2014 | | |
| WO | 2019001572 A1 | 1/2019 | | |
| WO | WO 2020224568 A1 * | 11/2020 | .......... | C07D 471/04 |
| WO | 2022/133215 A1 | 6/2022 | | |

OTHER PUBLICATIONS

Bastin R.J. et al., "Salt Selection and Optimisation Procedures for Pharmaceutical New Chemical Entities", Organic Process Research & Development 4:427-435 (2000), cited in RU OA & SR.
Belikov V.G., "Relationship Between the Chemical Structure, Properties of Substances and Their Effect on the Body", Pharmaceutical Chemistry, Chapter 2.6, MEDpress-inform, Moscow, pp. 27-29 (2007), cited in RU OA & SR.
Cheek S. et al., "Sequence and Structure Classification of Kinases", J. Mol. Biol. 320:855-881 (2002), cited in RU OA & SR.
Healy A.M. et al., "Pharmaceutical Solvates, Hydrates and Amorphous Forms: A Special Emphasis on Cocrystals", Advanced Drug Delivery Reviews 117:25-46 (Aug. 2017), cited in RU OA & SR.
Mashkovsky M.D., Medicines, Moscow, Novaya Volna LLC, Publisher S.B. Divov, 1:11 (2001), cited in RU OA & SR.

(Continued)

*Primary Examiner* — Jeffrey S Lundgren
*Assistant Examiner* — Heather Dahlin
(74) *Attorney, Agent, or Firm* — Scully, Scott, Murphy & Presser, P.C.

(57) ABSTRACT

A kinase inhibitor, comprising a compound of formula (I) or a pharmaceutically acceptable salt, solvate, ester, acid, metabolite or prodrug thereof. A method and a use for using the inhibitor for treatment of diseases related to CDK9 and/or mutagenic activity thereof.

Formula (I)

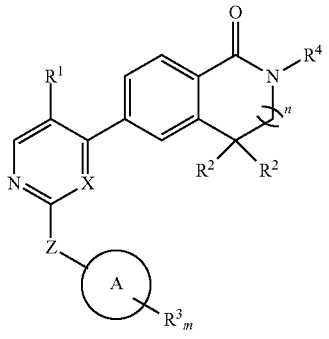

12 Claims, No Drawings

Specification includes a Sequence Listing.

(56) References Cited

OTHER PUBLICATIONS

Ram P.R. et al., "Prodrug as a Novel Approach of Drug Delivery", Journal of Drug Delivery and Therapeutics 5 (3):5-9 (2015), cited in RU OA & SR.

Zawilska J.B. et al., "Prodrugs: A Challenge for the Drug Development", Pharmacological Reports 65(1):1-14 (2013), cited in RU OA & SR.

Chemical Encyclopedic Dictionary, Ch. Ed. I.L. Knunyants, Sov. Encyclopedia, Moscow, 792:130-131 (1983), cited in RU OA & SR.

Big Medical Encyclopedia, Sovetskaya Encyclopedia Publishing House, Moscow, 15:87 (1981), cited in RU OA & SR.

Russian Office Action and Search Report dated Mar. 28, 2024 received in Russian Application No. 2023110506/04 (022395), together with an English-language translation.

Chinese Office Action dated Jan. 8, 2025 received in Chinese Patent Application No. 202111227801.8, together with an English-language translation.

International Search Report dated Jan. 20, 2022 issued in PCT/CN2021/125280, 4 pages.

Wang, Li et al., "Discovery of a novel and highly selective CDK9 kinase inhibitor (JSH-009) with potent antitumor efficacy in preclinical acute myeloid leukemia models", Investigational New Drugs (2020), vol. 38, pp. 1272-1281.

Japanese Notice of Reasons for Refusal dated Aug. 20, 2024 received in Japanese Application No. 2023-530578, together with an English-language translation.

Lv K. et al., "Rational Design and Evaluation of 6-(Pyrimidin-2-ylamino)-3,4-Dihydroquinoxalin-2(1H)-Ones as Polypharmacological Inhibitors of BET and Kinases", Journal of Medicinal Chemistry 63:9787-9802 (2020) (cited in EP Extended Search Report).

European Extended Search Report dated Sep. 27, 2024 received in European Application No. 21 893 674.8.

* cited by examiner

SEQUENCE LISTING

```
<160> NUMBER OF SEQ ID NOS: 2

<210> SEQ ID NO 1
<211> LENGTH: 6856
<212> TYPE: DNA
<213> ORGANISM: Artificial Sequence
<220> FEATURE:
<223> OTHER INFORMATION: Recombinant plasmid DNA C37-CL

<400> SEQUENCE: 1

gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gccaccatgg tggactacag cgtgtgggac cacattgagg tgtctgatga tgaagacgag    960
```

-continued acgcacccca acatcgacac ggccagtctc ttccgctggc ggcatcaggc ccgggtggaa 1020
cgcatggagc agttccagaa ggagaaggag gaactggaca ggggctgccg cgagtgcaag 1080
cgcaaggtgg ccgagtgcca gaggaaactg aaggagctgg aggtggccga gggcggcaag 1140
gcagagctgg agcgcctgca ggccgaggca cagcagctgc gcaaggagga gcggagctgg 1200
gagcagaagc tggaggagat gcgcaagaag gagaagagca tgccctggaa cgtggacacg 1260
ctcagcaaag acggcttcag caagagcatg gtaaatacca agcccgagaa gacggaggag 1320
gactcagagg aggtgaggga gcagaaacac aagaccttcg tggaaaaata cgagaaacag 1380
atcaagcact ttggcatgct tcgccgctgg gatgacagcc aaaagtacct gtcagacaac 1440
gtccacctgg tgtgcgagga gacagccaat tacctggtca tttggtgcat tgacctagag 1500
gtggaggaga aatgtgcact catggagcag gtggcccacc agacaatcgt catgcaattt 1560
atcctggagc tggccaagag cctaaaggtg gacccccggg cctgcttccg gcagttcttc 1620
actaagatta agacagccga tcgccagtac atggagggct tcaacgacga gctggaagcc 1680
ttcaaggagc gtgtgcgggg ccgtgccaag ctgcgcatcg agaaggccat gaaggagtac 1740
gaggaggagg agcgcaagaa gcggctcggc cccggcggcc tggacccegt cgaggtctac 1800
gagtccctcc ctgaggaact ccagaagtgc ttcgatgtga aggacgtgca gatgctgcag 1860
gacgccatca gcaagatgga ccccaccgac gcaaagtacc acatgcagcg ctgcattgac 1920
tctggcctct gggtccccaa ctctaaggcc agcgaggcca aggagggaga ggaggcaggt 1980
cctggggacc cattactgga agctgttccc aagacgggcg atgagaagga tgtcagtgtg 2040
aagcttggta ccgagctcgg atccggtggc ggagggagcg gtggcggagg gagcggcggc 2100
cgcaagcccg acgtcgtcca gattgtccgc aactacaacg cctaccttcg ggccagcgac 2160
gatctgccta agatgttcat cgagtccgac cctgggttct tttccaacgc tattgtcgag 2220
ggagctaaga agttccctaa caccgagttc gtgaaggtga agggcctcca cttcagccag 2280
gaggacgctc cagatgaaat gggtaagtac atcaagagct tcgtggagcg cgtgctgaag 2340
aacgagcaga gtctagaggc tgactacaaa gaccatgacg gtgattataa agatcatgac 2400
atcgactaca aggatgacga tgacaagtga gtttaaaccc gctgatcagc ctcgactgtg 2460
ccttctagtt gccagccatc tgttgtttgc ccctcccccg tgccttcctt gaccctggaa 2520
ggtgccactc ccactgtcct ttcctaataa aatgaggaaa ttgcatcgca ttgtctgagt 2580
aggtgtcatt ctattctggg gggtggggtg gggcaggaca gcaaggggga ggattgggaa 2640
gacaatagca ggcatgctgg ggatgcggtg ggctctatgg cttctgaggc ggaaagaacc 2700
agctggggct ctagggggta tccccacgcg ccctgtagcg gcgcattaag cgcggcgggt 2760
gtggtggtta cgcgcagcgt gaccgctaca cttgccagcg ccctagcgcc cgctcctttc 2820
gctttcttcc cttcctttct cgccacgttc gccggctttc cccgtcaagc tctaaatcgg 2880
gggctccctt tagggttccg atttagtgct ttacggcacc tcgaccccaa aaaacttgat 2940
tagggtgatg gttcacgtag tgggccatcg ccctgataga cggtttttcg ccctttgacg 3000
ttggagtcca cgttctttaa tagtggactc ttgttccaaa ctggaacaac actcaaccct 3060
atctcggtct attcttttga tttataaggg attttgccga tttcggccta ttggttaaaa 3120
aatgagctga tttaacaaaa atttaacgcg aattaattct gtggaatgtg tgtcagttag 3180
ggtgtggaaa gtccccaggc tccccagcag gcagaagtat gcaaagcatg catctcaatt 3240
agtcagcaac caggtgtgga aagtccccag gctccccagc aggcagaagt atgcaaagca 3300
tgcatctcaa ttagtcagca accatagtcc cgcccctaac tccgcccatc ccgcccctaa 3360

-continued

```
ctccgcccag ttccgcccat tctccgcccc atggctgact aattttttt atttatgcag   3420
aggccgaggc cgcctctgcc tctgagctat tccagaagta gtgaggaggc tttttggag   3480
gcctaggctt ttgcaaaaag ctcccgggag cttgtatatc cattttcgga tctgatcaag   3540
agacaggatg aggatcgttt cgcatgattg aacaagatgg attgcacgca ggttctccgg   3600
ccgcttgggt ggagaggcta ttcggctatg actgggcaca acagacaatc ggctgctctg   3660
atgccgccgt gttccggctg tcagcgcagg ggcgcccggt tctttttgtc aagaccgacc   3720
tgtccggtgc cctgaatgaa ctgcaggacg aggcagcgcg gctatcgtgg ctggccacga   3780
cgggcgttcc ttgcgcagct gtgctcgacg ttgtcactga agcgggaagg gactggctgc   3840
tattgggcga agtgccgggg caggatctcc tgtcatctca ccttgctcct gccgagaaag   3900
tatccatcat ggctgatgca atgcggcggc tgcatacgct tgatccggct acctgcccat   3960
tcgaccacca agcgaaacat cgcatcgagc gagcacgtac tcggatggaa gccggtcttg   4020
tcgatcagga tgatctggac gaagagcatc aggggctcgc gccagccgaa ctgttcgcca   4080
ggctcaaggc gcgcatgccc gacggcgagg atctcgtcgt gacccatggc gatgcctgct   4140
tgccgaatat catggtggaa aatggccgct tttctggatt catcgactgt ggccggctgg   4200
gtgtggcgga ccgctatcag gacatagcgt tggctacccg tgatattgct gaagagcttg   4260
gcggcgaatg ggctgaccgc ttcctcgtgc tttacggtat cgccgctccc gattcgcagc   4320
gcatcgcctt ctatcgcctt cttgacgagt tcttctgagc gggactctgg ggttcgaaat   4380
gaccgaccaa gcgacgccca acctgccatc acgagatttc gattccaccg ccgccttcta   4440
tgaaaggttg ggcttcggaa tcgttttccg ggacgccggc tggatgatcc tccagcgcgg   4500
ggatctcatg ctggagttct tcgcccaccc caacttgttt attgcagctt ataatggtta   4560
caaataaagc aatagcatca caaatttcac aaataaagca tttttttcac tgcattctag   4620
ttgtggtttg tccaaactca tcaatgtatc ttatcatgtc tgtataccgt cgacctctag   4680
ctagagcttg gcgtaatcat ggtcatagct gtttcctgtg tgaaattgtt atccgctcac   4740
aattccacac aacatacgag ccggaagcat aaagtgtaaa gcctggggtg cctaatgagt   4800
gagctaactc acattaattg cgttgcgctc actgcccgct ttccagtcgg gaaacctgtc   4860
gtgccagctg cattaatgaa tcggccaacg cgcggggaga ggcggtttgc gtattgggcg   4920
ctcttccgct tcctcgctca ctgactcgct gcgctcggtc gttcggctgc ggcgagcggt   4980
atcagctcac tcaaaggcgg taatacggtt atccacagaa tcaggggata acgcaggaaa   5040
gaacatgtga gcaaaaggcc agcaaaaggc caggaaccgt aaaaaggccg cgttgctggc   5100
gtttttccat aggctccgcc cccctgacga gcatcacaaa aatcgacgct caagtcagag   5160
gtggcgaaac ccgacaggac tataaagata ccaggcgttt ccccctggaa gctccctcgt   5220
gcgctctcct gttccgaccc tgccgcttac cggatacctg tccgcctttc tcccttcggg   5280
aagcgtggcg ctttctcata gctcacgctg taggtatctc agttcggtgt aggtcgttcg   5340
ctccaagctg ggctgtgtgc acgaaccccc cgttcagccc gaccgctgcg ccttatccgg   5400
taactatcgt cttgagtcca acccggtaag acacgactta tcgccactgg cagcagccac   5460
tggtaacagg attagcagag cgaggtatgt aggcggtgct acagagttct tgaagtggtg   5520
gcctaactac ggctacacta gaagaacagt atttggtatc tgcgctctgc tgaagccagt   5580
taccttcgga aaaagagttg gtagctcttg atccggcaaa caaaccaccg ctggtagcgg   5640
tttttttgtt tgcaagcagc agattacgcg cagaaaaaaa ggatctcaag aagatccttt   5700
```

-continued gatcttttct acggggtctg acgctcagtg gaacgaaaac tcacgttaag ggattttggt 5760
catgagatta tcaaaaagga tcttcaccta gatcctttta aattaaaaat gaagttttaa 5820
atcaatctaa agtatatatg agtaaacttg gtctgacagt taccaatgct taatcagtga 5880
ggcacctatc tcagcgatct gtctatttcg ttcatccata gttgcctgac tccccgtcgt 5940
gtagataact acgatacggg agggcttacc atctggcccc agtgctgcaa tgataccgcg 6000
agacccacgc tcaccggctc cagatttatc agcaataaac cagccagccg gaagggccga 6060
gcgcagaagt ggtcctgcaa ctttatccgc ctccatccag tctattaatt gttgccggga 6120
agctagagta agtagttcgc cagttaatag tttgcgcaac gttgttgcca ttgctacagg 6180
catcgtggtg tcacgctcgt cgtttggtat ggcttcattc agctccggtt cccaacgatc 6240
aaggcgagtt acatgatccc ccatgttgtg caaaaaagcg gttagctcct tcggtcctcc 6300
gatcgttgtc agaagtaagt tggccgcagt gttatcactc atggttatgg cagcactgca 6360
taattctctt actgtcatgc catccgtaag atgcttttct gtgactggtg agtactcaac 6420
caagtcattc tgagaatagt gtatgcggcg accgagttgc tcttgcccgg cgtcaatacg 6480
ggataatacc gcgccacata gcagaacttt aaaagtgctc atcattggaa aacgttcttc 6540
ggggcgaaaa ctctcaagga tcttaccgct gttgagatcc agttcgatgt aacccactcg 6600
tgcacccaac tgatcttcag catcttttac tttcaccagc gtttctgggt gagcaaaaac 6660
aggaaggcaa aatgccgcaa aaaagggaat aagggcgaca cggaaatgtt gaatactcat 6720
actcttcctt tttcaatatt attgaagcat ttatcagggt tattgtctca tgagcggata 6780
catatttgaa tgtatttaga aaaataaaca aataggggtt ccgcgcacat ttccccgaaa 6840
agtgccacct gacgtc 6856

<210> SEQ ID NO 2
<211> LENGTH: 7338
<212> TYPE: DNA
<213> ORGANISM: Artificial Sequence
<220> FEATURE:
<223> OTHER INFORMATION: Recombinant plasmid DNA CDK9-NL

<400> SEQUENCE: 2
gacggatcgg gagatctccc gatcccctat ggtgcactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300
tggagttccg cgttacataa cttacggtaa atggcccgcc tggctgaccg cccaacgacc 360
cccgcccatt gacgtcaata atgacgtatg ttcccatagt aacgccaata gggactttcc 420
attgacgtca atgggtggag tatttacggt aaactgccca cttggcagta catcaagtgt 480
atcatatgcc aagtacgccc cctattgacg tcaatgacgg taaatggccc gcctggcatt 540
atgcccagta catgacctta tgggactttc ctacttggca gtacatctac gtattagtca 600
tcgctattac catggtgatg cggttttggc agtacatcaa tgggcgtgga tagcggtttg 660
actcacgggg atttccaagt ctccacccca ttgacgtcaa tgggagtttg ttttggcacc 720
aaaatcaacg ggactttcca aaatgtcgta acaactccgc cccattgacg caaatgggcg 780
gtaggcgtgt acggtgggag gtctatataa gcagagctct ctggctaact agagaaccca 840
ctgcttactg gcttatcgaa attaatacga ctcactatag ggagacccaa gctggctagc 900

-continued

```
gccaccatgg cttccaaggt gtacgacccc gagcaacgca aacgcatgat cactgggcct    960
cagtggtggg ctcgctgcaa gcaaatgaac gtgctggact ccttcatcaa ctactatgat   1020
tccgagaagc acgccgagaa cgccgtgatt tttctgcatg gtaacgctgc ctccagctac   1080
ctgtggaggc acgtcgtgcc tcacatcgag cccgtggcta gatgcatcat ccctgatctg   1140
atcggaatgg gtaagtccgg caagagcggg aatggctcat atcgcctcct ggatcactac   1200
aagtacctca ccgcttggtt cgagctgctg aaccttccaa agaaaatcat ctttgtgggc   1260
cacgactggg gggcttgtct ggcctttcac tactcctacg agcaccaaga caagatcaag   1320
gccatcgtcc atgctgagag tgtcgtggac gtgatcgagt cctgggacga gtggcctgac   1380
atcgaggagg atatcgccct gatcaagagc gaagagggcg agaaaatggt gcttgagaat   1440
aacttcttcg tcgagaccat gctcccaagc aagatcatgc ggaaactgga gcctgaggag   1500
ttcgctgcct acctggagcc attcaaggag aagggcgagg ttagacggcc taccctctcc   1560
tggcctcgcg agatccctct cgttaaggga ggcggtggcg gagggagcgg tggcggaggg   1620
agcaagcttg gtaccgagct cggatccact agatctgtta acgtgtggtg gaattctatg   1680
gcaaagcagt acgactcggt ggagtgccct ttttgtgatg aagtttccaa atacgagaag   1740
ctcgccaaga tcggccaagg caccttcggg gaggtgttca aggccaggca ccgcaagacc   1800
ggccagaagg tggctctgaa gaaggtgctg atggaaaacg agaaggaggg gttccccatt   1860
acagccttgc gggagatcaa gatccttagc ttctaaaaca cgagaatgtg gtcaacttga   1920
ttgagatttg tcgaaccaaa gcttcccccct ataaccgctg caagggtagt atatacctgg   1980
tgttcgactt ctgcgagcat gaccttgctg ggctgttgag caatgttttg gtcaagttca   2040
cgctgtctga gatcaagagg gtgatgcaga tgctgcttaa cggcctctac tacatccaca   2100
gaaacaagat cctgcatagg gacatgaagg ctgctaatgt gcttatcact cgtgatgggg   2160
tcctgaagct ggcagacttt gggctggccc gggccttcag cctggccaag aacagccagc   2220
ccaaccgcta caccaaccgt gtggtgacac tctggtaccg gcccccggag ctgttgctcg   2280
gggagcggga ctacggcccc cccattgacc tgtggggtgc tgggtgcatc atggcagaga   2340
tgtggacccg cagccccatc atgcagggca acacggagca gcaccaactc gccctcatca   2400
gtcagctctg cggctccatc accccctgagg tgtggccaaa cgtggacaac tatgagctgt   2460
acgaaaagct ggagctggtc aagggccaga agcggaaggt gaaggacagg ctgaaggcct   2520
atgtgcgtga cccatacgca ctggacctca tcgacaagct gctggtgctg gaccctgccc   2580
agcgcatcga cagcgatgac gccctcaacc acgacttctt ctggtccgac cccatgccct   2640
ccgacctcaa gggcatgctc tccacccacc tgacgtccat gttcgagtac ttggcaccac   2700
cgcgccggaa gggcagccag atcacccagc agtccaccaa ccagagtcgc aatcccgcca   2760
ccaccaacca gacggagttt gagcgcgtct tctggaattc tgcagatatc cagcacagtg   2820
gcggccgctc gagtctagag gctgactaca aagaccatga cggtgattat aaagatcatg   2880
acatcgacta caaggatgac gatgacaagt gagtttaaac ccgctgatca gcctcgactg   2940
tgccttctag ttgccagcca tctgttgttt gcccctcccc cgtgccttcc ttgaccctgg   3000
aaggtgccac tcccactgtc ctttcctaat aaaatgagga aattgcatcg cattgtctga   3060
gtaggtgtca ttctattctg gggggtgggg tggggcagga cagcaagggg gaggattggg   3120
aagacaatag caggcatgct ggggatgcgg tgggctctat ggcttctgag gcggaaagaa   3180
ccagctgggg ctctaggggg tatccccacg cgccctgtag cggcgcatta agcgcggcgg   3240
```

-continued

```
gtgtggtggt tacgcgcagc gtgaccgcta cacttgccag cgccctagcg cccgctcctt   3300
tcgctttctt cccttccttt ctcgccacgt tcgccggctt tccccgtcaa gctctaaatc   3360
gggggctccc tttagggttc cgatttagtg ctttacggca cctcgacccc aaaaaacttg   3420
attagggtga tggttcacgt agtgggccat cgccctgata gacggttttt cgccctttga   3480
cgttggagtc cacgttcttt aatagtggac tcttgttcca aactggaaca acactcaacc   3540
ctatctcggt ctattctttt gatttataag ggattttgcc gatttcggcc tattggttaa   3600
aaaatgagct gatttaacaa aaatttaacg cgaattaatt ctgtggaatg tgtgtcagtt   3660
agggtgtgga aagtccccag gctccccagc aggcagaagt atgcaaagca tgcatctcaa   3720
ttagtcagca accaggtgtg gaaagtcccc aggctcccca gcaggcagaa gtatgcaaag   3780
catgcatctc aattagtcag caaccatagt cccgccccta actccgccca tcccgcccct   3840
aactccgccc agttccgccc attctccgcc ccatggctga ctaatttttt ttatttatgc   3900
agaggccgag gccgcctctg cctctgagct attccagaag tagtgaggag gcttttttgg   3960
aggcctaggc ttttgcaaaa agctcccggg agcttgtata tccattttcg gatctgatca   4020
agagacagga tgaggatcgt ttcgcatgat tgaacaagat ggattgcacg caggttctcc   4080
ggccgcttgg gtggagaggc tattcggcta tgactgggca caacagacaa tcggctgctc   4140
tgatgccgcc gtgttccggc tgtcagcgca ggggcgcccg gttctttttg tcaagaccga   4200
cctgtccggt gccctgaatg aactgcagga cgaggcagcg cggctatcgt ggctggccac   4260
gacgggcgtt ccttgcgcag ctgtgctcga cgttgtcact gaagcgggaa gggactggct   4320
gctattgggc gaagtgccgg ggcaggatct cctgtcatct caccttgctc ctgccgagaa   4380
agtatccatc atggctgatg caatgcggcg gctgcatacg cttgatccgg ctacctgccc   4440
attcgaccac caagcgaaac atcgcatcga gcgagcacgt actcggatgg aagccggtct   4500
tgtcgatcag gatgatctgg acgaagagca tcaggggctc gcgccagccg aactgttcgc   4560
caggctcaag gcgcgcatgc ccgacggcga ggatctcgtc gtgacccatg gcgatgcctg   4620
cttgccgaat atcatggtgg aaaatggccg cttttctgga ttcatcgact gtggccggct   4680
gggtgtggcg gaccgctatc aggacatagc gttggctacc cgtgatattg ctgaagagct   4740
tggcggcgaa tgggctgacc gcttcctcgt gctttacggt atcgccgctc ccgattcgca   4800
gcgcatcgcc ttctatcgcc ttcttgacga gttcttctga gcgggactct ggggttcgaa   4860
atgaccgacc aagcgacgcc caacctgcca tcacgagatt tcgattccac cgccgccttc   4920
tatgaaaggt tgggcttcgg aatcgttttc cgggacgccg gctggatgat cctccagcgc   4980
ggggatctca tgctggagtt cttcgcccac cccaacttgt ttattgcagc ttataatggt   5040
tacaaataaa gcaatagcat cacaaatttc acaaataaag catttttttc actgcattct   5100
agttgtggtt tgtccaaact catcaatgta tcttatcatg tctgtatacc gtcgacctct   5160
agctagagct tggcgtaatc atggtcatag ctgtttcctg tgtgaaattg ttatccgctc   5220
acaattccac acaacatacg agccggaagc ataaagtgta aagcctgggg tgcctaatga   5280
gtgagctaac tcacattaat tgcgttgcgc tcactgcccg ctttccagtc gggaaacctg   5340
tcgtgccagc tgcattaatg aatcggccaa cgcgcgggga gaggcggttt gcgtattggg   5400
cgctcttccg cttcctcgct cactgactcg ctgcgctcgg tcgttcggct gcggcgagcg   5460
```

-continued

```
gtatcagctc actcaaaggc ggtaatacgg ttatccacag aatcagggga taacgcagga   5520
aagaacatgt gagcaaaagg ccagcaaaag gccaggaacc gtaaaaaggc cgcgttgctg   5580
gcgtttttcc ataggctccg cccccctgac gagcatcaca aaaatcgacg ctcaagtcag   5640
aggtggcgaa acccgacagg actataaaga taccaggcgt ttccccctgg aagctccctc   5700
gtgcgctctc ctgttccgac cctgccgctt accggatacc tgtccgcctt tctcccttcg   5760
ggaagcgtgg cgctttctca tagctcacgc tgtaggtatc tcagttcggt gtaggtcgtt   5820
cgctccaagc tgggctgtgt gcacgaaccc cccgttcagc ccgaccgctg cgccttatcc   5880
ggtaactatc gtcttgagtc caacccggta agacacgact tatcgccact ggcagcagcc   5940
actggtaaca ggattagcag agcgaggtat gtaggcggtg ctacagagtt cttgaagtgg   6000
tggcctaact acggctacac tagaagaaca gtatttggta tctgcgctct gctgaagcca   6060
gttaccttcg gaaaaagagt tggtagctct tgatccggca aacaaaccac cgctggtagc   6120
ggtttttttg tttgcaagca gcagattacg cgcagaaaaa aaggatctca agaagatcct   6180
ttgatctttt ctacggggtc tgacgctcag tggaacgaaa actcacgtta agggattttg   6240
gtcatgagat tatcaaaaag gatcttcacc tagatccttt taaattaaaa atgaagtttt   6300
aaatcaatct aaagtatata tgagtaaact tggtctgaca gttaccaatg cttaatcagt   6360
gaggcaccta tctcagcgat ctgtctattt cgttcatcca tagttgcctg actccccgtc   6420
gtgtagataa ctacgatacg ggagggctta ccatctggcc ccagtgctgc aatgataccg   6480
cgagacccac gctcaccggc tccagattta tcagcaataa accagccagc cggaagggcc   6540
gagcgcagaa gtggtcctgc aactttatcc gcctccatcc agtctattaa ttgttgccgg   6600
gaagctagag taagtagttc gccagttaat agtttgcgca acgttgttgc cattgctaca   6660
ggcatcgtgg tgtcacgctc gtcgtttggt atggcttcat tcagctccgg ttcccaacga   6720
tcaaggcgag ttacatgatc ccccatgttg tgcaaaaaag cggttagctc cttcggtcct   6780
ccgatcgttg tcagaagtaa gttggccgca gtgttatcac tcatggttat ggcagcactg   6840
cataattctc ttactgtcat gccatccgta agatgctttt ctgtgactgg tgagtactca   6900
accaagtcat tctgagaata gtgtatgcgg cgaccgagtt gctcttgccc ggcgtcaata   6960
cgggataata ccgcgccaca tagcagaact ttaaaagtgc tcatcattgg aaaacgttct   7020
tcggggcgaa aactctcaag gatcttaccg ctgttgagat ccagttcgat gtaacccact   7080
cgtgcaccca actgatcttc agcatctttt actttcacca gcgtttctgg gtgagcaaaa   7140
acaggaaggc aaaatgccgc aaaaaaggga ataagggcga cacggaaatg ttgaatactc   7200
atactcttcc tttttcaata ttattgaagc atttatcagg gttattgtct catgagcgga   7260
tacatatttg aatgtattta gaaaaataaa caaatagggg ttccgcgcac atttccccga   7320
aaagtgccac ctgacgtc                                                 7338
```

DIHYDROISOQUINOLINONE AND ISOINDOLINONE DERIVATIVES AND USES THEREOF

TECHNICAL FIELD

The invention relates to the pharmaceutical field, in particular to compounds containing dihydroisoquinolinone/isoindolinone structure and pyrimidine/pyridine structure and their preparation methods, as well as methods and uses for treating and/or preventing diseases.

INCORPORATION BY REFERENCE OF SEQUENCE LISTING

The Sequence Listing in an ASCII text file, named as 42054_Sequence_Listing.txt of 19 KB, created on Apr. 29, 2023, and submitted to the United States Patent and Trademark Office via EFS-Web, is incorporated herein by reference.

BACKGROUND

The family of cyclin-dependent kinase (CDK) protein consists of members that are key regulators of the cell division cycle (cell cycle CDKs), members that are involved in regulation of gene transcription (transcription CDKs), and members with other functions. CDKs equire for activation the association with a regulatory cyclin subunit. The cell cycle CDKs CDK1/cyclin B, CDK2/cyclin A, CDK2/cyclin E, CDK4/cyclin D, and CDK6/cyclin D in cell cycle CDKs get activated in a sequential order to drive a cell into and through the cell division cycle. The transcriptional CDKs CDK9/cyclin T and CDK7/cyclin H regulate the activity of RNA polymerase II via phosphorylation of the carboxyl-terminal domain (CTD). Positive transcription factor b (P-TEFb) is a heterodimer of CDK9 and one of four cyclin partners (cyclin T1, cyclin K, cyclin T2a or T2b).

Whereas CDK9 (NCBI GenBank Gene ID 1025) is exclusively involved in transcriptional regulation, CDK7 in addition participates in cell cycle regulation as CDK-activating kinase (CAK).

Transcription of genes by RNA polymerase II is initiated by assembly of the pre-initiation complex at the promoter region and phosphorylation of Ser 5 and Ser 7 of the CTD by CDK7/cyclin H. For a major fraction of genes RNA polymerase II stops mRNA transcription after it moved 20-40 nucleotides along the DNA template. This promoter-proximal pausing of RNA polymerase II is mediated by negative elongation factors and is recognized as a major control mechanism to regulate expression of rapidly induced genes in response to a variety of stimuli (Cho et al., Cell Cycle 9, 1697, 2010). P-TEFb is crucially involved in overcoming promoter-proximal pausing of RNA polymerase II and transition into a productive elongation state by phosphorylation of Ser2 of the CTD as well as by phosphorylation and inactivation of negative elongation factors.

Activity of P-TEFb itself is regulated by several mechanisms. About half of cellular P-TEFb exists in an inactive complex with 7SK small nuclear RNA (7SK snRNA), La-related protein 7 (LARP7/PIP7S) and hexamethylene bis-acetamide inducible proteins ½ (HEXIM1/2, He et al., Mol Cell 29, 588, 2008). The remaining half of P-TEFb exists in an active complex containing the bromodomain protein Brd4 (Yang et al., Mol Cell 19, 535, 2005). Brd4 recruits P-TEFb through interaction with acetylated histones to chromatin areas primed for gene transcription. Through alternately interacting with its positive and negative regulators, P-TEFb is maintained in a functional equilibrium: P-TEFb bound to the 7SK snRNA complex represents a reservoir from which active P-TEFb can be released on demand of cellular transcription and cell proliferation. Furthermore, the activity of P-TEFb is regulated by posttranslational modifications including phosphorylation/de-phosphorylation, ubiquitination, and acetylation.

Deregulated activity of CDK9 kinase activity of the P-TEFb heterodimer is associated with a variety of human pathological settings such as hyper-proliferative diseases (e.g. cancer), virally induced infectious diseases or cardiovascular diseases.

Cancer is regarded as a hyper-proliferative disorder mediated by a disbalance of proliferation and cell death (apoptosis). High levels of anti-apoptotic Bcl-2-family proteins are found in various human tumors and account for prolonged survival of tumor cells and therapy resistance. Inhibition of P-TEFb kinase activity was shown to reduce transcriptional activity of RNA polymerase II leading to a decline of short-lived anti-apoptotic proteins (especially Mcl-1 and XIAP), reinstalling the ability of tumor cells to undergo apoptosis. A number of other proteins associated with the transformed tumor phenotype (such as Myc, NF-kB responsive gene transcripts, mitotic kinases) are either short-lived proteins or are encoded by short-lived transcripts (sensitive to reduced RNA polymerase II activity mediated by P-TEFb inhibition).

There is no research on the drug resistance of CDK9 inhibitor. In this invention, the cell lines resistant to CDK9 inhibitor were obtained through long-term administration, and the compounds of the invention were found to inhibit the cell lines that have drug resistant due to the long-term administration of CDK9 inhibitor. After further protein expression of CDK9 mutant protein in drug-resistant cell lines and detection, it was found that the compounds of the invention can overcome the drug-resistant mutation of CDK9.

In addition, many viruses rely on the transcriptional machinery of the host cell for the transcription of their own genome. In case of HIV-1, RNA polymerase II gets recruited to the promoter region within the viral LTR's. The viral transcription activator (Tat) protein binds to nascent viral transcripts and overcomes promoter-proximal RNA polymerase II pausing by recruitment of P-TEFb which in turn promotes transcriptional elongation. Furthermore, the Tat protein increases the fraction of active P-TEFb by replacement of the P-TEFb inhibitory proteins HEXIM1/2 within the 7SK snRNA complex. Recent data have shown that inhibition of the kinase activity of P-TEFb is sufficient to block HIV-1 repliction at kinase inhibitor concentrations that are not cytotoxic to the host cells (reviewed in Wang & Fischer, Trends Pharmacol Sci 29, 302, 2008). Similarly, recruitment of P-TEFb by viral proteins has been reported for other viruses such as B-cell cancer-associated Epstein-Barr virus, where the nuclear antigen EBNA2 protein interacts with P-TEFb (Bark-Jones et al., Oncogene, 25, 1775, 2006), and the human T-lymphotropic virus type 1 (HTLV-1), where the transcriptional activator Tax recruits P-TEFb (Zhou et al., J Virol. 80, 4781, 2006).

Cardiac hypertrophy, the heart's adaptive response to mechanical overload and pressure (hemodynamic stress e.g. hypertension, myocardial infarction), can lead, on a long term, to heart failure and death. Cardiac hypertrophy was shown to be associated with increased transcriptional activity and RNA polymerase II CTD phosphorylation in cardiac muscle cells. P-TEFb was found to be activated by dissociation from the inactive 7SK snRNA/HEXIM1/2 complex. These findings suggest pharmacological inhibition of P-TEFb kinase activity as a therapeutic approach to treat cardiac hypertrophy (reviewed in Dey et al., Cell Cycle 6, 1856, 2007).

In summary, multiple lines of evidence suggest that selective inhibition of the CDK9 kinase activity of the P-TEFb heterodimer (=CDK9 and one of four cyclin partners, cyclin T1, cyclin K, cyclin T2a or T2b) represents an innovative approach for the treatment of diseases such as cancer, viral diseases, and/or diseases of the heart. CDK9 belongs to a family of at least 13 closely related kinases of which the subgroup of the cell cycle CDK's fulfills multiple roles in regulation of cell proliferation. Thus, co-inhibition of cell cycle CDKs (e.g. CDK1/cyclin B, CDK2/cyclin A, CDK2/cyclin E, CDK4/cyclin D, CDK6/cyclin D) and of CDK9, is expected to impact normal proliferating tissues such as intestinal mucosa, lymphatic and hematopoietic organs, and reproductive organs. To maximize the therapeutic margin of CDK9 kinase inhibitors, molecules with high selectivity towards CDK9 are required.

In general, although various CDK inhibitors are known, selective CDK9 inhibitors are still required to treat diseases such as hyperproliferative diseases, viral diseases and/or diseases of the heart, which can provide one or more advantages over the compounds known in the prior arts.

SUMMARY OF INVENTION

The invention relates to a kinase inhibitor, comprising a compound of formula (I) or a pharmaceutically acceptable salt, solvate, ester, acid, metabolite or prodrug thereof, Formula (I)

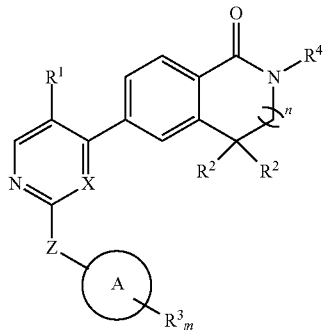

wherein, A is selected from the group consisting of cyclohexyl, phenyl, pyridinyl and piperidyl;

X is CH or N;

Z is —NH— or —NH—C(=O)—;

n is 0 or 1;

$R^1$ is selected from the group consisting of hydrogen, halogen, cyano, (C1-C6)alkyl, and (C1-C6)haloalkyl;

$R^2$ are selected from the group consisting of hydrogen and (C1-C6)alkyl, or two $R^2$ together form a (C3-C6) cycloalkyl;

m is selected from the integer of 1-3, and each $R^3$ is independently selected from the group consisting of hydrogen, —NH—(C1-C3)alkyl-(C1-C3)alkoxy, halogen, (C1-C6)alkyl, (C1-C6)alkoxy, (C1-C6)haloalkyl, (C1-C6)alkylacylamino, (C1-C6)alkylsulfonyl, (C1-C6)alkylsulfonamido, aminosulfonyl, (C1-C6)alkylaminosulfonyl, heterocyclyl sulfonyl with heteroatom (s) being optionally substituted by (C1-C6)alkyl, carboxyl(C1-C3)alkyl, aminosulfonyl(C1-C3)alkyl, (C1-C3)alkylsulfonyl(C1-C3)alkyl, (C1-C3)alkylsulfonyl(C3-C6)cycloalkyl, heterocyclyl aminoacyl with heteroatom(s) being optionally substituted by (C1-C6)alkyl, heterocyclyl with heteroatom(s) being optionally substituted by (C1-C6)alkyl, —S(=O)(=NH)(C1-C3)alkyl, and —(C1-C3)alkyl-S(=O)(=NH)(C1-C3)alkyl;

$R^4$ is selected from the group consisting of hydrogen and (C1-C6)alkyl.

In a preferred embodiment, the invention relates to a compound of formula (Ia) or a pharmaceutically acceptable salt, solvate, ester, acid, metabolite or prodrug thereof, Formula (Ia)

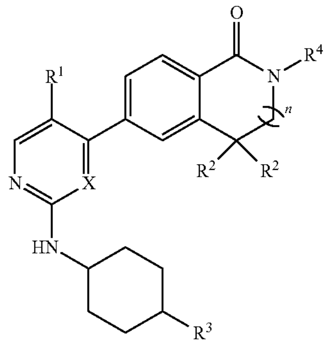

wherein, X, n, $R^1$, $R^2$, $R^3$, and $R^4$ are defined as above.

In this embodiment, X is preferably N; in another embodiment, $R^3$ is preferably —NH—(C1-C3)alkyl-(C1-C3)alkoxy or carboxyl(C1-C3)alkyl.

In another preferred embodiment, the invention relates to a compound of formula (Ib) or a pharmaceutically acceptable salt, solvate, ester, acid, metabolite or prodrug thereof, Formula (Ib)

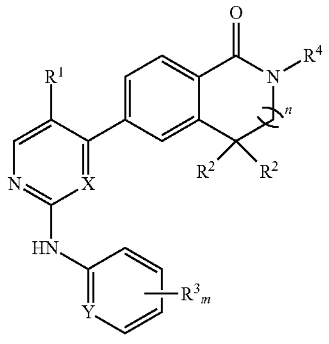

wherein, Y is CH or N; X, m, n, $R^1$, $R^2$, $R^3$, and $R^4$ are defined as above.

In a more preferred aspect, X is N; in another preferred aspect, Y is CH.

In another preferred aspect, each $R^3$ is independently selected from the group consisting of halogen, (C1-C6)alkyl, (C1-C6)alkoxy, (C1-C6)haloalkyl, (C1-C6)alkylsulfonyl, (C1-C6)alkylsulfonamido, aminosulfonyl, (C1-C6)alkylaminosulfonyl, heterocyclyl sulfonyl with heteroatom(s) being optionally substituted by (C1-C6)alkyl, aminosulfonyl (C1-C3)alkyl, (C1-C3)alkylsulfonyl(C1-C3)alkyl, (C1-C3) alkylsulfonyl(C3-C6)cycloalkyl, heterocyclyl aminoacyl with heteroatom(s) being optionally substituted by (C1-C6)

alkyl, heterocyclyl with heteroatom(s) being optionally substituted by (C1-C6)alkyl, —S(═O)(═NH)(C1-C3)alkyl, and —(C1-C3)alkyl-S(═O)(═NH)(C1-C3)alkyl.

In another preferred embodiment, the invention relates to a compound of formula (Ic) or a pharmaceutically acceptable salt, solvate, ester, acid, metabolite or prodrug thereof, Formula (Ic)

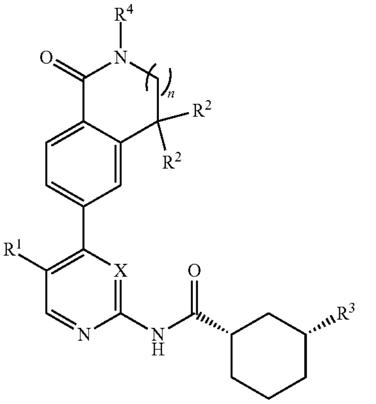

wherein, X, n, $R^1$, $R^2$, $R^3$ and $R^4$ are defined as above.

In a more preferred aspect, $R^3$ is (C1-C6)alkylacylamino.

In another preferred embodiment, the invention relates to a compound of formula (Id) or a pharmaceutically acceptable salt, solvate, ester, acid, metabolite or prodrug thereof, Formula (Id)

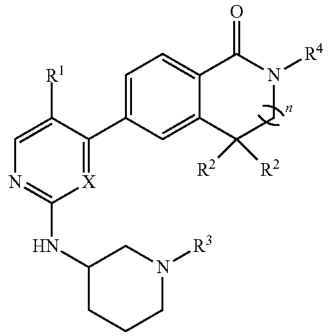

wherein, X, n, $R^1$, $R^2$, $R^3$ and $R^4$ are defined as above.

In this embodiment, X is preferably N; in a more preferred aspect, $R^3$ is (C1-C6)alkylsulfonyl.

In another aspect, the application also relates to a pharmaceutical composition comprising the kinase inhibitor of the invention and a pharmaceutically acceptable diluent or carrier.

In another aspect, the application relates to a use of the kinase inhibitor of the invention in the preparation of medicament for treating hyperproliferative disorders, virus induced infectious diseases and cardiovascular diseases.

In another aspect, the application also relates to a method for treating hyperproliferative disorders, virus induced infectious diseases and cardiovascular diseases by using the kinase inhibitor of the invention.

DETAILED DESCRIPTION

Definitions

Unless otherwise defined, all technical and scientific terms used herein have the same meaning as commonly understood by one of ordinary skill in the art to which this invention belongs. In the specification, the singular forms also include the plural unless the context clearly dictates otherwise. All publications, patent applications, patents and other references mentioned herein are incorporated by reference. In the case of conflict, the present specification, including definitions, will control. In addition, the materials, methods and examples are illustrative only and are not intended to be limiting.

Unless otherwise indicated, conventional methods of mass spectroscopy, NMR, HPLC, protein chemistry, biochemistry, recombinant DNA techniques and pharmacology that are within the skill of the art are employed in the invention. Unless specific definitions are provided, the nomenclature employed in connection with, and the laboratory procedures and techniques of, analytical chemistry, synthetic organic chemistry, and medicinal and pharmaceutical chemistry described herein are those known in the art. The foregoing techniques and procedures can be generally performed with conventional methods well known in the art and those as described in various general and more specific references that are cited and discussed throughout the present specification.

The term "alkyl" refers to an aliphatic hydrocarbon group, which may be branched or straight alkyl. Depending on the structure, an alkyl group may be a monoradical or a diradical (i.e., an alkylene group). In the invention, the alkyl group is preferably an alkyl having 1 to 8 carbon atoms, more preferably a "lower alkyl" having 1 to 6 carbon atoms, and even more preferably an alkyl having 1 to 3 carbon atoms. Typical alkyl groups include, but are not limited to, methyl, ethyl, propyl, butyl, pentyl, hexyl, and the like. It should be understood that the "alkyl" as mentioned herein encompasses all configurations and conformations that may exist of the alkyl, e.g., the "propyl" as mentioned herein intends to encompass n-propyl and isopropyl, "butyl" as mentioned herein intends to encompass n-butyl, isobutyl, and tertiary butyl, and "pentyl" as mentioned herein intends to encompass n-pentyl, isopentyl, neopentyl, tert-pentyl, pent-3-yl, etc.

The term "alkoxy" refers to a —O-alkyl group, where alkyl is as defined herein. Typical alkoxy groups include, but are not limited to, methoxy, ethoxy, propoxy, butoxy, pentyloxy, hexyloxy, and the like.

The term "alkoxyalkyl" refers to an alkyl group as defined herein is substituted with alkoxy as defined herein.

The term "cycloalkyl" refers to a monocyclic or polycyclic radical that contains only carbon and hydrogen. Cycloalkyl groups include groups having from 3 to 12 ring atoms. Depending on the structure, a cycloalkyl group can be a monoradical or a diradical (e.g., a cycloalkylene group). In the invention, the cycloalkyl group is preferably a cycloalkyl having 3 to 8 carbon atoms, and more preferably a "lower cycloalkyl" having 3 to 6 carbon atoms. Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl.

The term "alkyl(cycloalkyl)" or "cycloalkylalkyl" refers to an alkyl group as defined herein is substituted with cycloalkyl as defined herein. Non-limiting examples of cycloalkylalkyl include cyclopropylmethyl, cyclobutylmethyl, cyclopentylmethyl, cyclohexylmethyl, etc.

The term "aromatic" refers to a planar ring having a delocalized 71-electron system containing 4n+2 $\pi$ electrons, where n is an integer. Aromatic rings can be formed by five, six, seven, eight, nine, or more than nine atoms. Aromatics can be optionally substituted. The term "aromatic" includes both carbocyclic aryl (e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

As used herein, the term "aryl" refers to an aromatic ring wherein each of the atoms forming the ring is a carbon atom. Aryl rings can be formed by five, six, seven, eight, nine, or more than nine carbon atoms. Aryl groups can be optionally substituted. Examples of aryl groups include, but are not limited to phenyl, naphthalenyl, phenanthrenyl, anthracenyl, fluorenyl, and indenyl. Depending on the structure, an aryl group can be a monoradical or a diradical (i.e., an arylene group).

The term "aryloxy" refers to —O-aryl, wherein aryl is as defined herein.

The term "heteroaryl" refers to an aryl group that includes one or more ring heteroatoms selected from nitrogen, oxygen and sulfur. An N-containing "heteroaryl" moiety refers to an aromatic group in which at least one of the skeletal atoms of the ring is a nitrogen atom. Depending on the structure, the heteroaryl group may be a monoradical or a diradical (i.e., a heteroarylene group). Examples of heteroaryl groups include, but are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuryl, indazolyl, indolizinyl, phthalazinyl, pyridazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, naphthyridinyl, furopyridinyl, and the like.

The term "heteroalkyl" used herein refers to an alkyl defined herein with one or more chain backbone atom(s) being heteroatoms, such as oxygen, nitrogen, sulfur, silicon, phosphorus or their combination. The heteroatoms (one or more) may locate at any position with the heteroalkyl or at the position where the heteroalkyl is connected with the rest of the molecule.

As used herein, the term "heterocycloalkyl" or "heterocyclyl" refers to a non-aromatic ring wherein one or more atoms forming the ring is a heteroatom selected from the group consisting of nitrogen, oxygen and sulfur. Heterocycloalkyl rings can be monocyclic or bicyclic ring formed by three, four, five, six, seven, eight, nine, or more than nine atoms. Heterocycloalkyl rings can be optionally substituted. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, imidazolidine, pyrrolidone, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Depending on the structure, a heterocycloalkyl group can be a monoradical or a diradical (i.e., a heterocycloalkylene group).

The term "alkyl(heterocycloalkyl)" or "heterocycloalkylalkyl" refers to an alkyl group as defined herein that is substituted with heterocycloalkyl as defined herein.

The term "halo" or "halogen" refers to fluoro, chloro, bromo and iodo.

The terms "haloalkyl", "haloalkoxy" and "haloheteroalkyl" include alkyl, alkoxy or heteroalkyl structures in which at least one hydrogen is replaced with a halogen atom. In certain embodiments in which two or more hydrogen atoms are replaced with halogen atoms, the halogen atoms are the same or different from each other.

The term "hydroxy" refers to an —OH group.

The term "cyano" refers to a —CN group.

The term "carboxyl" refers to a —COOH group.

The term "ester" refers to a chemical moiety having formula —COOR, wherein R is selected from the group consisting of alkyl, cycloalkyl, aryl, heteroaryl (connected via cyclocarbon) and heterocyclyl (connected via cyclocarbon).

The term "amino" refers to a $—NH_2$ group.

The term "aminoacyl" refers to a $—CO—NH_2$ group.

The term "alkyl aminoacyl" refers to a —CO—NH—R group, wherein R is alkyl as defined herein.

The term "amide" or "amido" refers to —NR—CO—R', wherein R and R' are independently hydrogen or alkyl.

The term "alkylamino" refers to an amino substituent which is further substituted with one or two alkyl groups, specifically refers to the group —NRR', wherein R and R' are each independently selected from the group consisting of hydrogen or lower alkyl, with the proviso that —NRR' is not $—NH_2$. "Alkylamino" includes groups of compounds in which the nitrogen atom of $—NH_2$ is attached to at least one alkyl group. Examples of alkylamino groups include, but are not limited to, methylamino, ethylamino, and the like. "Dialkylamino" includes groups in which the nitrogen atom of $—NH_2$ is attached to at least two other alkyl groups. Examples of dialkylamino groups include, but are not limited to, dimethylamino, diethylamino, and the like.

The term "cycloalkylamino" refers to an amino substituent further substituted with one or two cycloalkyl groups as defined herein.

The term "heterocycloalkylamino" refers to an amino radical, as defined herein, substituted with a heterocycloalkyl group, as defined herein.

The term "alkylaminoalkyl" refers to an alkyl radical, as defined herein, substituted with an alkylamino group, as defined herein.

The term "aminoalkyl" refers to an alkyl substituent further substituted with one or more amino groups.

The term "aminoalkoxy" refers to an alkoxy substituent further substituted with one or more amino groups.

The term "hydroxyalkyl" or "hydroxylalkyl" refers to an alkyl substituent further substituted with one or more hydroxy groups.

The term "cyanoalkyl" refers to an alkyl substituent further substituted with one or more cyano groups.

The term "carboxylalkyl" refers to alkyl substituents further substituted with one or more carboxyl groups.

The term "acyl" refers to a monovalent atomic radical remaining after removal of the hydroxyl group from an organic or inorganic oxyacid, represented by a general formula of R-M(O)—, wherein M is usually C.

The term "carbonyl" is an organic functional group (C═O) formed by carbon atom and oxygen atom through a double bond linkage.

The term "alkanoyl" or "alkylcarbonyl" refers to a carbonyl group further substituted with an alkyl group. Typical alkanoyl groups include, but are not limited to, acetyl, propionyl, butyryl, valeryl, hexanoyl and the like.

The term "sulfuryl" or "sulfonyl" refers to a functional group after the sulfonic acid loses the hydroxyl group, and specifically refers to a —S(=O)$_2$— group.

The term "aminosulfuryl" or "aminosulfonyl" refers to a —S(=O)$_2$—NH$_2$ group.

The term "alkylsulfuryl" or "alkylsulfonyl" refers to —S(=O)$_2$—R, where R is an alkyl group.

The term "alkylsulfurylamido" or "alkylsulfonamido", and "cycloalkylsulfurylamido" or "cycloalkylsulfonamido" refer to an amino radical, as defined herein, substituted with an alkylsulfuryl group or a cycloalkylsulfuryl group, as defined herein, that is, —NH—S(=O)$_2$—R, wherein R is alkyl or cycloalkyl, respectively.

The terms "cycloalkylsulfuryl" and "cycloalkylsulfonyl" refer to —S(=O)$_2$—R, where R is a cycloalkyl group.

The term "optionally" means that one or more events described hereinafter may or may not occur, and include both the event(s) that may occur and the event(s) that may not occur. The term "optionally substituted" or "substituted" refers to that the mentioned group may be substituted with one or more additional groups which are each independently selected from alkyl, cycloalkyl, aryl, heteroaryl, heterocyclyl, hydroxy, alkoxy, cyano, halo, amide, nitro, haloalkyl, amino, methylsulfonyl, alkylcarbonyl, alkoxy carbonyl, heteroarylalkyl, heterocycloalkylalkyl, aminoacyl, amino protecting group, etc., wherein, the amino protecting group is preferably selected from the group consisting of pivaloyl, tert-butoxycarbonyl, benzyloxycarbonyl, 9-fluorenylmethoxycarbonyl, benzyl, p-methoxybenzyl, allyloxycarbonyl, trifluoroacetyl, and the like.

Herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

A "metabolite" of a compound disclosed herein is a derivative of that compound that is formed when the compound is metabolized. The term "active metabolite" refers to a biologically active derivative of a compound that is formed when the compound is metabolized. The term "metabolized" as used herein, refers to the sum of the processes (including, but not limited to, hydrolysis reactions and reactions catalyzed by enzymes, such as, oxidation reactions) by which a particular substance is changed by an organism.

Thus, enzymes may produce specific structural alterations to a compound. For example, cytochrome P450 catalyzes a variety of oxidative and reductive reactions while uridine diphosphate glucuronyl transferases catalyze the transfer of an activated glucuronic acid molecule to aromatic alcohol, aliphatic alcohol, carboxylic acid, amine and free sulfhydryl group. Further information on metabolism may be obtained from *The Pharmacological Basis of Therapeutics,* 9th Edition, McGraw-Hill (1996). Metabolites of the compounds disclosed herein can be identified either by administration of compounds to a host and analysis of tissue samples from the host, or by incubation of compounds with hepatic cells in vitro and analysis of the resulting compounds. Both methods are well known in the art. In some embodiments, metabolites of a compound are formed by oxidative processes and correspond to the corresponding hydroxy-containing compound. In some embodiments, a compound is metabolized to pharmacologically active metabolites.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "prodrug" or "a precursor of a drug" refers to derivatives that may not possess pharmacological activity, but may, in certain instances, be administered orally or parenterally and thereafter metabolized in the body to form compounds of the invention which are pharmacologically active. Non-limiting examples of prodrugs include esters, carbonate esters, hemi-esters, phosphate esters, nitro esters, sulfate esters, sulfoxides, amides, carbamates, azo-compounds, phosphamides, glycosides, ethers, acetals, and ketals, etc.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "treating" as used herein refers to alleviate of at least one symptom of the disease, disorder or condition. The term encompasses the administration and/or application of one or more compounds described herein, to a subject, for the purpose of providing management of, or remedy for a condition. "Treatment" for the purposes of this disclosure, may, but does not have to, provide a cure; rather, "treatment" may be in the form of management of the condition. When the compounds described herein are used to treat unwanted proliferating cells, including cancers, "treatment" includes partial or total destruction of the undesirable proliferating cells with minimal destructive effects on normal cells. A desired mechanism of treatment of unwanted rapidly proliferating cells, including cancer cells, at the cellular level is apoptosis.

The term "preventing" as used herein includes either preventing or slowing the onset of a clinically evident disease progression altogether or preventing or slowing the onset of a preclinically evident stage of a disease in individuals at risk. This includes prophylactic treatment of those at risk of developing a disease.

The term "subject" or "patient" includes organisms which are capable of suffering from a cell proliferative disorder or a disorder associated with reduced or insufficient programmed cell death (apoptosis) or who could otherwise benefit from the administration of a compound of the invention, such as human and non-human animals.

Preferred humans include human patients suffering from or prone to suffering from diseases or related conditions as described herein. The term "non-human animal" includes vertebrates, e.g., mammals, such as non-human primates, sheep, cattle, dogs, cats and rodents, e.g., mice, and non-mammals, such as chickens, amphibians, reptiles, etc.

As used herein, $GI_{50}$ refers to a concentration of a medicine required for inhibiting the growth of 50% cells i.e., the medicine concentration at which the growth of 50% cells (such as cancer cells) is inhibited or controlled.

As used herein, $IC_{50}$ refers to an amount, concentration or dosage of a particular test compound that achieves a 50% inhibition of a maximal response, in an assay that measures such response.

As used herein, $EC_{50}$ refers to a dosage, concentration or amount of a test compound that elicits a dose-dependent response at 50% of maximal expression of a particular response that is induced, provoked or potentiated by the particular test compound.

The term "diseases relating to CDK9 and/or its mutations" or "diseases mediated by CDK9 and/or its mutations" shall include diseases associated with the activities of CDK9 and/or its mutations or involving the activities of CDK9 and/or its mutations (such as hyperactivity of CDK9 and/or its mutations), as well as the conditions accompanying these diseases. Examples of "diseases relating to CDK9 and/or its mutations" or "diseases mediated by CDK9 and/or its mutations" include diseases resulting from increased activities of CDK9 and/or its mutations due to mutations in genes regulating the activities of CDK9 and/or its mutations (such as LARP7, HEXIM1/2 or 7sk snRNA), diseases resulting from increased activities of CDK9 and/or its mutations due to activation of CDK9/cyclin T/RNA polymerase II complex by viral proteins (such as HIVTAT or HTLV-TAX), or diseases resulting from increased activities of CDK9 and/or its mutations due to activation of mitogenic signaling pathways.

The term "hyperactivity of CDK9" refers to an increased enzymatic activity of CDK9 and/or its mutations compared to normal non-diseased cells, or to increased CDK9 activity leading to undesired cell proliferation or to reduced or insufficient programmed cell death (apoptosis), or to mutations leading to constitutive activation of CDK9.

The term "hyper-proliferative disorder" includes disorders involving the undesired or uncontrolled cell proliferation, and it includes disorders involving reduced or insufficient programmed cell death (apoptosis).

Kinase Inhibitor of the Invention

The invention relates to a kinase inhibitor, comprising a compound of formula (I) or a pharmaceutically acceptable salt, solvate, ester, acid, metabolite or prodrug thereof, Formula (I)

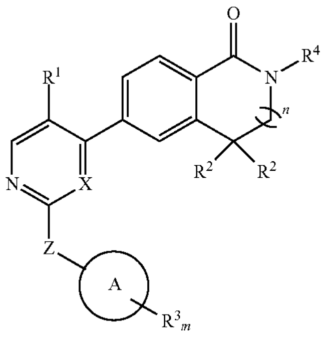

wherein, A is selected from the group consisting of cyclohexyl, phenyl, pyridinyl and piperidyl;

n is 0 or 1;

X is CH or N;

Z is —NH— or —NH—C(═O)—;

$R^1$ is selected from the group consisting of hydrogen, halogen, cyano, (C1-C6)alkyl, and (C1-C6)haloalkyl;

$R^2$ are selected from the group consisting of hydrogen and (C1-C6)alkyl, or two $R^2$ together form a (C3-C6) cycloalkyl;

m is selected from the integer of 1-3, and each $R^3$ is independently selected from the group consisting of hydrogen, —NH—(C1-C3)alkyl-(C1-C3)alkoxy, halogen, (C1-C6)alkyl, (C1-C6)alkoxy, (C1-C6)haloalkyl, (C1-C6)alkylacylamino, (C1-C6)alkylsulfonyl, (C1-C6)alkylsulfonamido, aminosulfonyl, (C1-C6)alkylaminosulfonyl, heterocyclyl sulfonyl with heteroatom(s) being optionally substituted by (C1-C6)alkyl, carboxyl(C1-C3)alkyl, aminosulfonyl(C1-C3)alkyl, (C1-C3)alkylsulfonyl(C1-C3)alkyl, (C1-C3)alkylsulfonyl(C3-C6)cycloalkyl, heterocyclyl aminoacyl with heteroatom(s) being optionally substituted by (C1-C6)alkyl, heterocyclyl with heteroatom(s) being optionally substituted by (C1-C6)alkyl, —S(═O)(═NH)(C1-C3)alkyl, and —(C1-C3)alkyl-S(═O)(═NH)(C1-C3)alkyl;

$R^4$ is selected from the group consisting of hydrogen and (C1-C6)alkyl.

In a preferred embodiment, the invention relates to a compound of formula (Ia) or a pharmaceutically acceptable salt, solvate, ester, acid, metabolite or prodrug thereof, Formula (Ia)

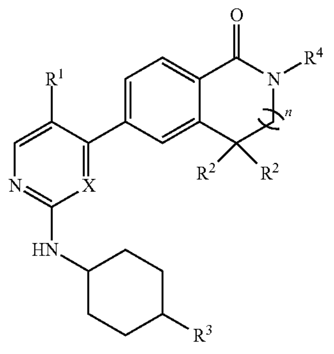

wherein, X, n, $R^1$, $R^2$, $R^3$, and $R^4$ are defined as above.

In this embodiment, X is preferably N; in another embodiment, $R^3$ is preferably —NH—(C1-C3)alkyl-(C1-C3)alkoxy or carboxyl(C1-C3)alkyl.

In another preferred embodiment, the invention relates to a compound of formula (Ib) or a pharmaceutically acceptable salt, solvate, ester, acid, metabolite or prodrug thereof, Formula (Ib)

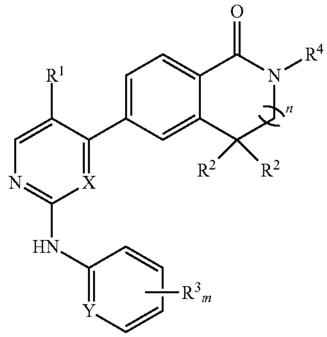

wherein, Y is CH or N; X, m, n, $R^1$, $R^2$, $R^3$, and $R^4$ are defined as above.

In a more preferred aspect, X is N; in another preferred aspect, Y is CH.

In another preferred aspect, each $R^3$ is independently selected from the group consisting of halogen, (C1-C6)alkyl, (C1-C6)alkoxy, (C1-C6)haloalkyl, (C1-C6)alkylsulfonyl, (C1-C6)alkylsulfonamido, aminosulfonyl, (C1-C6)alkylaminosulfonyl, heterocyclyl sulfonyl with heteroatom(s) being optionally substituted by (C1-C6)alkyl, aminosulfonyl (C1-C3)alkyl, (C1-C3)alkylsulfonyl(C1-C3)alkyl, (C1-C3) alkylsulfonyl(C3-C6)cycloalkyl, heterocyclyl aminoacyl with heteroatom(s) being optionally substituted by (C1-C6) alkyl, heterocyclyl with heteroatom(s) being optionally substituted by (C1-C6)alkyl, —S(═O)(═NH)(C1-C3)alkyl, and —(C1-C3)alkyl-S(═O)(═NH)(C1-C3)alkyl.

In another preferred embodiment, the invention relates to a compound of formula (Ic) or a pharmaceutically acceptable salt, solvate, ester, acid, metabolite or prodrug thereof, Formula (Ic)

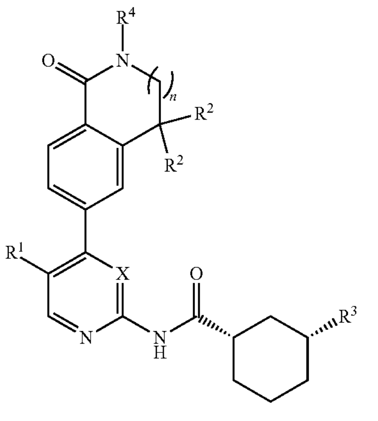

wherein, X, n, $R^1$, $R^2$, $R^3$ and $R^4$ are defined as above.

In a more preferred aspect, $R^3$ is (C1-C6)alkylacylamino.

In another preferred embodiment, the invention relates to a compound of formula (Id) or a pharmaceutically acceptable salt, solvate, ester, acid, metabolite or prodrug thereof, Formula (Id)

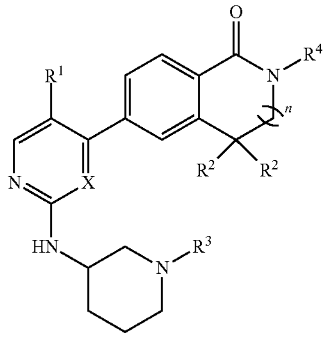

wherein, X, n, $R^1$, $R^2$, $R^3$ and $R^4$ are defined as above.

In this embodiment, X is preferably N; in a more preferred aspect, $R^3$ is (C1-C6)alkylsulfonyl.

In the exemplary embodiment of the invention, $R^1$ is preferably selected from the group consisting of hydrogen, chlorine, fluorine, cyano, (C1-C3)alkyl (more preferably methyl), and (C1-C3)haloalkyl (more preferably trifluoromethyl).

In another exemplary embodiment, $R^2$ are preferably selected from the group consisting of hydrogen, (C1-C3) alkyl (more preferably methyl), or two $R^2$ together form cyclopropyl or cyclobutyl.

In other exemplary embodiments, each $R^3$ is independently selected from the group consisting of hydrogen, (2-methoxy)ethylamino, chlorine, fluorine, methyl, methoxy, trifluoromethyl, acetylamino, methanesulfonyl, methanesulfonylamino, sulfamoyl, methylsulfamoyl, dimethylsulfamoyl, morpholinosulfonyl, carboxymethyl, sulfamoyl methyl, methanesulfonylmethyl, methanesulfonylcyclopropyl (N-methylpiperidin-4-yl)aminoacyl, N-methylpiperazin-1-yl, N-ethylpiperazin-1-yl, N-isopropylpiperazin-1-yl, homopiperazin-1-yl, —S(═O)(═NH)methyl, and -methyl-S(═O)(═NH)methyl.

In another exemplary embodiment, $R^4$ is preferably selected from the group consisting of hydrogen and (C1-C3)alkyl (more preferably methyl).

This description describes a novel kinase inhibitor. Also described is the pharmaceutically acceptable salts, solvates, esters, acids, metabolites and prodrugs of the compounds.

The compounds of the invention can exist in free form, e.g. as a free base, or as a free acid, or as a zwitterion, or can exist in the form of a salt. Said salt may be any salt, either an organic or inorganic addition salt, particularly any physiologically acceptable organic or inorganic addition salt, customarily used in pharmacy.

Salts which are preferred for the purposes of the invention are physiologically acceptable salts of the compounds according to the invention. However, salts which are not suitable for pharmaceutical applications per se, but which, for example, can be used for the isolation or purification of the compounds according to the invention, are also comprised.

The term "pharmaceutically acceptable salt" refers to a relatively non-toxic, inorganic or organic acid addition salt of a compound of the invention, for example, see S. M. Berge, et al. "Pharmaceutical Salts," J. Pharm. Sci. 1977, 66, 1-19.

Pharmaceutically acceptable salts of the compounds according to the invention encompass acid addition salts of mineral acids, carboxylic acids and sulfonic acids, for example salts of hydrochloric acid, hydrobromic acid, hydroiodic, sulfuric acid, bisulfuric acid, phosphoric acid, nitric acid; or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methanesulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Pharmaceutically acceptable salts of the compounds according to the invention also comprise salts of conventional bases, such as, by way of example and by preference, alkali metal salts (for example sodium and potassium salts), alkaline earth metal salts (for example calcium and magnesium salts) and ammonium salts derived from ammonia or organic amines with 1 to 16 C atoms, such as, by way of example and by preference, ethylamine, diethylamine, triethylamine, ethyldiisopropylamine, monoethanolamine, diethanolamine, triethanolamine, dicyclohexylamine, dimethylaminoethanol, procaine, dibenzylamine, V-methylmorpholine, arginine, lysine, ethylenediamine, V-methylpiperidine, -mefhylglucamine, dimethylglucamine, ethylglucamine, 1,6-hexadiamine, glucosamine, sarcosine, serinol, tris(hydroxymethyl)aminomethane, aminopropanediol, Sovak base, and 1-amino-2,3,4-butanetriol.

The invention includes all possible salts of the compounds of the invention as single salts, or as any mixture of said salts, in any ratio.

Solvates is the term used for the purposes of the invention for those forms of the compounds according to the invention which form a complex with solvent molecules by coordination in the solid or liquid state. Hydrates are a special form of solvates in which the coordination takes place with water. Hydrates are preferred as solvates within the scope of the invention.

In addition, the present invention also encompasses prodrugs of the compounds according to the invention. The term "prodrugs" encompasses compounds which themselves may be biologically active or inactive, but are converted (for example by metabolism or hydrolysis) to compounds according to the invention during their residence time in the body.

Furthermore, the invention includes all possible crystalline forms, or polymorphs, of the compounds of the invention, either as single polymorphs, or as a mixture of more than one polymorphs, in any ratio.

In this description, for convenience in some cases, the formula of the compound represents a specific isomer, but the invention includes all isomers, such as geometric isomers, optical isomers based on asymmetric carbon atoms, stereoisomers, tautomers, etc.

The chiral compounds involved in the invention may be of any configuration or mixed racemates. When a compound useful in accordance with the invention contains more than one chiral center, it may exist in diastereoisomeric forms. The diastereoisomeric compounds may be separated by methods known to those skilled in the art (for example, chromatography or crystallization) and the individual enantiomers may be separated as described above. The invention includes the use of various diastereoisomers of compounds useful in accordance with the invention, and mixtures thereof. Compounds useful in accordance with the invention may exist in different tautomeric forms or as different geometric isomers, and the invention includes the use of each tautomer and/or geometric isomer of compounds useful in accordance with the invention, and mixtures thereof. Compounds useful in accordance with the invention may exist in zwitterionic form. The invention includes the use of each zwitterionic form of compounds useful in accordance with the invention, and mixtures thereof.

The screening and characterization of the pharmaceutically acceptable salts, polymorphs and/or solvates may be accomplished using a variety of techniques including, but not limited to, thermal analysis, x-ray diffraction, spectroscopy, microscopy, and elemental analysis. The various spectroscopic techniques used include, but are not limited to, Raman, FTTR, UVIS, and NMR (liquid and solid state). The various microscopy techniques include, but are not limited to, IR microscopy and Raman microscopy.

Accordingly, the invention includes all possible salts, polymorphs, metabolites, hydrates, solvates, or prodrugs (e.g.: esters) of the compounds of the invention as single salt, polymorph, metabolite, hydrate, solvate, or prodrug (e.g.: ester), or as mixture of more than one salt, polymorph, metabolite, hydrate, solvate, or prodrug (e.g.: ester) in any ratio.

Treatment Method and Use

Another subject of the invention is the method and use of the kinase inhibitor of the invention for treating and/or preventing diseases, preferably diseases associated with or mediated by the activity of CDK9 and the mutations thereof, especially hyperproliferative diseases, virus induced infectious diseases and/or cardiovascular diseases, more preferably hyperproliferative diseases.

The compound of the invention can be used to inhibit the activity or expression of CDK9 and its mutants. Therefore, compounds of formulas (I), (Ia), (Ib), (Ic) or (Id) are valuable as therapeutic agents. In an embodiment, the invention provides a method for treating diseases associated with or mediated by the activity of CDK9 and the mutations thereof in a patient who needs to be treated, which comprises administering an effective amount of the compounds of formulas (I), (Ia), (Ib), (Ic) or (Id) as defined above to the patient. In some embodiments, the diseases associated with the activity of CDK9 and the mutants thereof are hyperproliferative disease, virus induced infectious diseases and/or cardiovascular diseases, more preferably hyperproliferative disease, especially cancer, and more preferably leukemia, liver cancer, ovarian cancer, cervical cancer, colorectal cancer, gastrointestinal stromal tumor, or lymphoma.

Hyperproliferative disorders in the context of the invention include, but are not limited to, e.g., psoriasis, keloids and other hyperplasias affecting the skin, endometriosis, skeletal disorders, angiogenic or blood vessel proliferative disorders, pulmonary hypertension, fibrotic disorders, mesangial cell proliferative disorders, colonic polyps, polycystic kidney disease, benign prostate hyperplasia, and solid tumors, such as cancers of the breast, respiratory tract, brain, reproductive organs, digestive tract, urinary tract, eye, liver, skin, head and neck, thyroid, parathyroid, and their distant metastases, lymphomas, sarcomas and leukemias.

Examples of breast cancer include, but are not limited to invasive ductal carcinoma, invasive lobular carcinoma, ductal carcinoma in situ, and lobular carcinoma in situ, canine or feline mammary carcinoma.

Examples of cancers of the respiratory tract include, but are not limited to small-cell and non-small-cell lung carcinoma, as well as bronchial adenoma, pleuropulmonary blastoma, and mesothelioma.

Examples of brain cancers include, but are not limited to brain stem and hypophtalmic glioma, cerebellar and cerebral astrocytoma, glioblastoma, medulloblastoma, ependymoma, as well as neuroectodermal and pineal tumor.

Tumors of reproductive organs include, but are not limited to prostate cancer, testicular cancer, endometrial cancer, cervical cancer, ovarian cancer, vaginal cancer, vulvar cancer, as well as sarcoma of the uterus.

Tumors of the digestive tract include, but are not limited to anal, colon, colorectal, esophageal, gallbladder, gastric, pancreatic, rectal, small-intestine, salivary gland cancers, and anal gland adenocarcinomas.

Tumors of the urinary tract include, but are not limited to bladder, penile, kidney, renal pelvis, ureter, urethral, and hereditary and sporadic papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, non-melanoma skin cancer, and mast cell tumors.

Head-and-neck cancers include, but are not limited to laryngeal, hypopharyngeal, nasopharyngeal, oropharyngeal cancer, lip cancer, oral cavity cancer, squamous cell cancer, and oral melanoma.

Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, rhabdomyosarcoma, malignant histiocytosis, fibrosarcoma, hemangiosarcoma, hemangiopericytoma, and leiomyosarcoma.

Leukemias include, but are not limited to acute myeloid leukemia, acute lymphoblastic leukemia, chronic lymphocytic leukemia, chronic myelogenous leukemia, and hairy cell leukemia.

The preferred subject of the invention is the treatment and/or prevention of lung cancer (especially non-small-cell lung carcinoma), prostate cancer (especially hormone-independent human prostate cancer), cervical cancer (including multidrug resistant human cervical cancer), colorectal cancer, melanoma, ovarian cancer or leukemia (especially acute myeloid leukemia).

Fibrotic proliferative disorders (i.e. the abnormal formation of extracellular matrices) that may be treated with the compounds and methods of the invention include lung fibrosis, atherosclerosis, restenosis, hepatic cirrhosis, and mesangial cell proliferative disorders, including renal diseases such as glomerulonephritis, diabetic nephropathy, malignant nephrosclerosis, thrombotic microangiopathy syndromes, transplant rejection, and glomerulopathies.

Other conditions in humans or other mammals that may be treated by administering a compound of the invention include tumor growth, retinopathy (including diabetic retinopathy, ischemic retinal-vein occlusion, retinopathy of prematurity and age-related macular degeneration), rheumatoid arthritis, psoriasis, and bullous disorders associated with subepidermal blister formation (including bullous pemphigoid, erythema multiforme and dermatitis herpetiformis).

The compounds of the invention may also be used to prevent and treat diseases of the airways and the lung, diseases of the gastrointestinal tract as well as diseases of the bladder and bile duct.

The disorders mentioned above have been well characterized in humans, but also exist with a similar etiology in other animals, including mammals, and can be treated by administering pharmaceutical compositions of the invention.

In a further aspect of the invention, the compounds according to the invention are used in a method for preventing and/or treating infectious diseases, in particular virally induced infectious diseases. The diseases include, but are not limited to virally induced infectious diseases, including opportunistic diseases, that are caused by retroviruses, hepadnaviruses, herpesviruses, flaviviridae, and/or adenoviruses. In a further preferred embodiment of this method, the retroviruses are selected from lentiviruses or oncoretroviruses, wherein the lentivirus is selected from the group comprising: HIV-1, HIV-2, FIV, BIV, SIV, SHIV, CAEV, VMV or EIAV, preferably HIV-1 or HIV-2; and wherein the oncoretrovirus is selected from the group of: HTLV-I, HTLV-II or BLV In a further preferred embodiment of this method, the hepadnavirus is selected from HBV, GSHV or WHV, preferably HBV; the herpesvirus is selected from the group comprising: HSV I, HSV II, EBV, VZV, HCMV or HHV 8, preferably HCMV; and the flaviviridae is selected from HCV, West nile or Yellow Fever.

The compounds of the invention are also useful for prophylaxis and/or treatment of cardiovascular diseases such as cardiac hypertrophy, adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, subdural hematoma, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome, mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome.

The compounds of the invention are preferably used for preventing and/or treating cardiac hypertrophy, adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis.

Another subject of the invention is the use of the kinase inhibitors of formulas (I), (Ia), (Ib), (Ic) or (Id) of the invention in the preparation of drugs.

Another subject of the invention is the use of the kinase inhibitors of formulas (I), (Ia), (Ib), (Ic) or (Id) of the invention in the preparation of madicament for the treatment and/or prevention of diseases, especially the above-mentioned diseases.

Pharmaceutical Composition

Another aspect of the invention relates to a pharmaceutical composition, which comprises the kinase inhibitor of the invention and a pharmaceutically acceptable diluent or carrier, as well as optionally one or more other active ingredient(s).

Another aspect of the invention relates to a pharmaceutical composition, which comprises the combination of the kinase inhibitor of formulas (I), (Ia), (Ib), (Ic) or (Id) of the invention with an inert, non-toxic, pharmaceutically appropriate adjuvant.

Another aspect of the invention relates to the use of the pharmaceutical composition of the invention for the treatment and/or prevention of diseases, in particular the above-mentioned diseases.

Another aspect of the invention relates to the use of the pharmaceutical composition of the invention for the treatment and/or prevention of lung carcinomas (especially non-small-cell lung carcinomas), prostate carcinomas (especially hormone-independent human prostate carcinomas), cervical carcinomas (including multidrug-resistant human cervical carcinomas), colorectal carcinomas, melanomas, ovarian carcinomas or leukemias (especially acute myeloid leukemias).

Compounds of the invention may be administered as the sole pharmaceutical agent or in combination with one or more additional therapeutic agents where the combination causes no unacceptable adverse effects. This pharmaceutical combination includes administration of a single pharmaceutical dosage formulation which contains a compound of the invention and one or more additional therapeutic agents, as well as administration of the compound of the invention and each additional therapeutic agent in its own separate pharmaceutical dosage formulation. For example, a compound of formulas (I), (Ia), (Ib), (Ic) or (Id) and a therapeutic agent may be administered to the patient together in a single oral dosage composition such as a tablet or capsule, or each agent may be administered in separate dosage formulations.

Where separate dosage formulations are used, the compound of the invention and one or more additional therapeutic agents may be administered at essentially the same time (e.g., concurrently) or at separately staggered times (e.g., sequentially).

In particular, the compounds of the present invention may be used in fixed or separate combination with other anti-tumor agents such as alkylating agents, anti-metabolites, plant-derived anti-tumor agents, hormonal therapy agents, topoisomerase inhibitors, camptothecin derivatives, kinase inhibitors, targeted drugs, antibodies, interferons and/or biological response modifiers, anti-angiogenic compounds, and other anti-tumor drugs. In this regard, the following is a non-limiting list of examples of secondary agents that may be used in combination with the compounds of the present invention: 1311-chTNT, abarelix, abiraterone, aclarubicin, aldesleukin, alemtuzumab, alitretinoin, altretamine, aminoglutethimide, amrubicin, amsacrine, anastrozole, arglabin, arsenic trioxide, asparaginase, azacitidine, basiliximab, BAY 80-6946, BAY 1000394, belotecan, bendamustine, bevacizumab, bexarotene, bicalutamide, bisantrene, bleomycin, bortezomib, buserelin, busulfan, cabazitaxel, calcium folinate, calcium levofolinate, capecitabine, carboplatin, carmofur, carmustine, catumaxomab, celecoxib, celmoleukin, cetuximab, chlorambucil, chlormadinone, chlormethine, cisplatin, cladribine, clodronic acid, clofarabine, crisantaspase, cyclophosphamide, cyproterone, cytarabine, dacarbazine, dactinomycin, darbepoetin alfa, dasatinib, daunorubicin, decitabine, degarelix, denileukin diftitox, denosumab, deslorelin, dibrospidium chloride, docetaxel, doxifluridine, doxorubicin, doxorubicin+estrone, eculizumab, edrecolomab, elliptinium acetate, eltrombopag, endostatin, enocitabine, epirubicin, epitiostanol, epoetin alfa, epoetin beta, eptaplatin, eribulin, erlotinib, estradiol, estramustine, etoposide, everolimus, exemestane, fadrozole, filgrastim, fludarabine, fluorouracil, flutamide, formestane, fotemustine, fulvestrant, gallium nitrate, ganirelix, gefitinib, gemcitabine, gemtuzumab, glutoxim, goserelin, histamine dihydrochloride, histrelin, hydroxycarbamide, I-125 seeds, ibandronic acid, ibritumomab tiuxetan, idarubicin, ifosfamide, imatinib, imiquimod, improsulfan, interferon alfa, interferon beta, interferon gamma, ipilimumab, irinotecan, ixabepilone, lanreotide, lapatinib, lenalidomide, lenograstim, lentinan, letrozole, leuprorelin, levamisole, lisuride, lobaplatin, lomustine, lonidamine, masoprocol, medroxyprogesterone, megestrol, melphalan, mepitiostane, mercaptopurine, methotrexate, methoxsalen, Methyl aminolevulinate, methyltestosterone, mifamurtide, miltefosine, miriplatin, mitobronitol, mitoguazone, mitolactol, mitomycin, mitotane, mitoxantrone, nedaplatin, nelarabine, nilotinib, nilutamide, nimotuzumab, nimustine, nitracrine, ofatumumab, omeprazole, oprelvekin, oxaliplatin, p53 gene therapy, paclitaxel, palifermin, palladium-103 seed, pamidronic acid, panitumumab, pazopanib, pegaspargase, PEG-epoetin beta (methoxy PEG-epoetin beta), pegfilgrastim, peginterferon alfa-2b, pemetrexed, pentazocine, pentostatin, peplomycin, perfosfamide, picibanil, pirarubicin, plerixafor, plicamycin, poliglusam, polyestradiol phosphate, polysaccharide-K, porfimer sodium, pralatrexate, prednimustine, procarbazine, quinagolide, radium-223 chloride, raloxifene, raltitrexed, ranimustine, razoxane, refametinib, regorafenib, risedronic acid, rituximab, romidepsin, romiplostim, sargramostim, sipuleucel-T, sizofiran, sobuzoxane, sodium glycididazole, sorafenib, streptozocin, sunitinib, talaporfin, tamibarotene, tamoxifen, tasonermin, teceleukin, tegafur, tegafur+gimeracil+oteracil, temoporfin, temozolomide, temsirolimus, teniposide, testosterone, tetrofosmin, thalidomide, thiotepa, thymalfasin, tioguanine, tocilizumab, topotecan, toremifene, tositumomab, trabectedin, trastuzumab, treosulfan, tretinoin, trilostane, triptorelin, trofosfamide, tryptophan, ubenimex, valrubicin, vandetanib, vapreotide, vemurafenib, vinblastine, vincristine, vindesine, vinflunine, vinorelbine, vorinostat, vorozole, yttrium-90 glass microspheres, zinostatin, zinostatin stimalamer, zoledronic acid, and zorubicin.

The compounds of the invention may also be employed in cancer treatment in conjunction with radiation therapy and/or surgical intervention.

The compounds according to the invention can act systemically and/or locally. For this purpose, they can be administered in a suitable way, such as, for example, by the oral, parenteral, pulmonal, nasal, sublingual, lingual, buccal, rectal, dermal, transdermal, conjunctival or otic route, or as an implant or stent.

For these administration routes, it is possible to administer the compounds according to the invention in suitable application forms.

Suitable for oral administration are administration forms which work as described in the prior art and deliver the compounds according to the invention rapidly and/or in modified form, which comprise the compounds according to the invention in crystalline and/or amorphous and/or dissolved form, such as, for example, tablets (coated or uncoated, for example tablets provided with enteric coatings or coatings whose dissolution is delayed or which are insoluble and which control the release of the compound according to the invention), tablets which rapidly decompose in the oral cavity, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (for example intravenously, intraarterially, intracardially, intraspinally or intralumbally) or with inclusion of absorption (for example intramuscularly, subcutaneously, intracutaneously, percutaneously or intraperitoneally). Administration forms suitable for parenteral administration are, inter alia, preparations for injection and infusion in the form of solutions, suspensions, emulsions, lyophilizates or sterile powders.

Examples suitable for the other administration routes are pharmaceutical forms for inhalation (inter alia powder inhalers, nebulizers), nasal drops/solutions/sprays; tablets to be administered lingually, sublingually or buccally, films/wafers or capsules, suppositories, preparations for the eyes or ears, vaginal capsules, aqueous suspensions (lotions, shaking mixtures), lipophilic suspensions, ointments, creams, transdermal therapeutic systems (such as plasters), milk, pastes, foams, dusting powders, implants or stents.

The compounds according to the invention can be converted into the stated administration forms. This can take place in a manner known per se by mixing with inert, nontoxic, pharmaceutically suitable adjuvants. These adjuvants include, inter alia, carriers (for example microcrystalline cellulose, lactose, mannitol), solvents (for example liquid polyethylene glycols), emulsifiers and dispersants or wetting agents (for example sodium dodecyl sulphate, polyoxysorbitan oleate), binders (for example polyvinylpyrrolidone), synthetic and natural polymers (for example albumin), stabilizers (for example antioxidants, such as, ascorbic acid), colorants (for example inorganic pigments, such as, iron oxides) and flavour- and/or odour-masking agents.

The invention furthermore provides medicaments comprising at least one compound according to the invention, usually together with one or more inert, nontoxic, pharmaceutically suitable adjuvants, and their use for the purposes mentioned above.

Regardless of the route of administration selected, the kinase inhibitors of the invention and/or the pharmaceutical compositions of the invention are formulated into pharmaceutically acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient without being toxic to the patient.

Preparation of Compounds

Compounds of the invention may be synthesized using standard synthetic techniques known to those of skill in the art or using methods known in the art in combination with methods described herein. In addition, solvents, temperatures and other reaction conditions presented herein may vary according to those of skill in the art. As a further guide the following synthetic methods may also be utilized.

The reactions can be used sequentially to provide the compounds described herein; or they can be used to synthesize fragments, which are then combined by the methods described herein and/or methods known in the art.

The starring materials used for the synthesis of the compounds described herein may be synthesized or can be obtained from commercial sources. The compounds described herein and other related compounds having different substituents can be synthesized using techniques and materials known to those of skill in the art. General methods for the preparation of compounds as disclosed herein may be derived from known reactions in the field, and the reactions may be modified by the use of appropriate reagents and conditions, as would be recognized by the skilled person, for the introduction of the various moieties into the molecules as provided herein.

The products of the reactions may be isolated and purified, if desired, using conventional techniques, including, but not limited to, filtration, distillation, crystallization, chromatography and the like. Such products may be characterized using conventional means, including physical constants and spectral data.

Non-limiting examples for of the synthesis scheme for preparing the compounds of formula (I) are described below.

EXAMPLES

The following specific non-limiting examples should be interpreted as illustrative only, but not limiting the invention in any way. Although no further detailed description is required, it is believed that those skilled in the art can fully utilize the present disclosure based on the description herein.

Example 1: Synthesis of 6-(2-(((4-((2-methoxyethyl)amino)cyclohexyl)amino) pyrimidin-4-yl)-3,4-dihydroisoquinolin-1(2H)-one

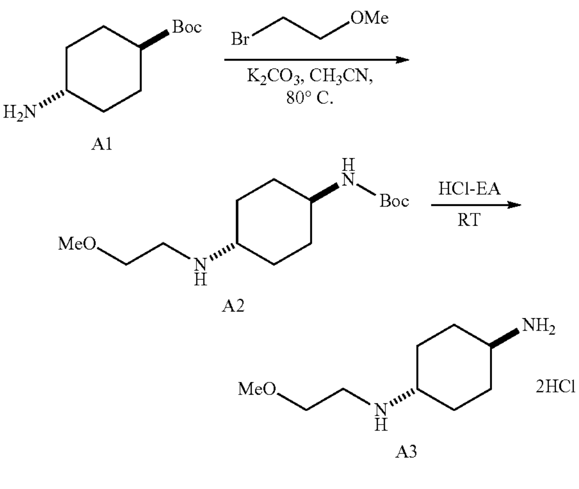

A1
A2
A3

-continued

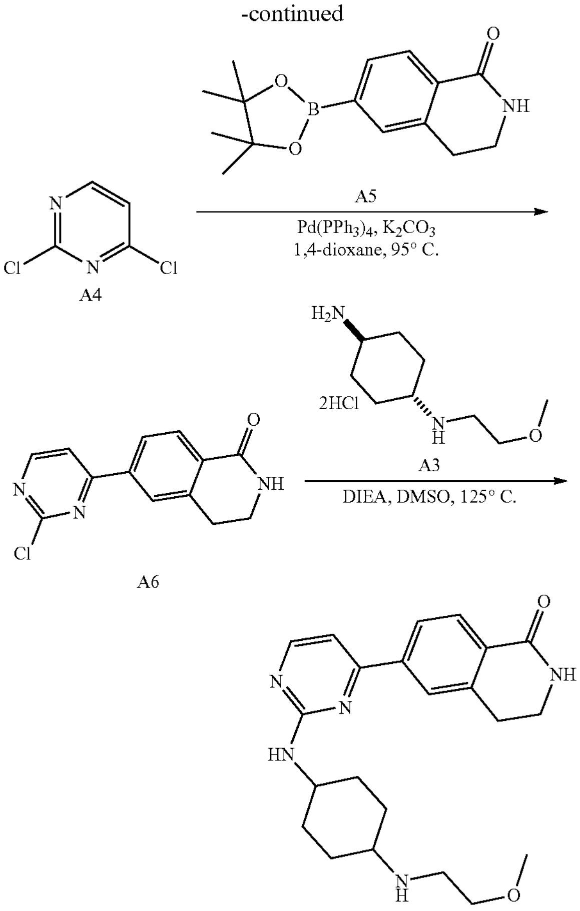

1

((1r, 4r)-4-((2-Methoxyethyl)amino)cyclohexyl)carbamic acid tert-butyl ester (A2): Compound A1 (10.0 g, 46.7 mmol), 2-bromoethylmethyl ether (5.2 g, 37.4 mmol) and potassium carbonate (12.9 g, 93.4 mmol) were added to acetonitrile (150 mL) and stirred at 80° C. for 16 hours. The reaction was stopped after TLC monitoring, showing that a small amount of raw material was left. The reaction solution was cooled to room temperature, filtered, and the filtrate was removed by rotary evaporation. The resultant was loaded on silica gel for column chromatography (eluent system: DCM/MeOH=100:1→40:1→20:1) to provide 6.3 g of yellow-white solid A2 in a yield of 50%.

(1r, 4r)-N1-(2-Methoxyethyl)cyclohexane-1,4-diamine hydrochloride (A3): Compound A2 (6 g, 22.0 mmol) was dissolved in HCl-EA (80 mL) and stirred at room temperature for 2 hours. A large amount of solid precipitations were obtained. The reaction solution was filtered and the filter cake was dried to obtain 5.1 g of white solid (dihydrochloride) A3, in a yield of 94.8%.

6-(2-Chloropyrimidin-4-yl)-3,4-dihydroisoquinolin-1(2H)-one (A6): A4 (81 mg, 0.54 mmol, 1.5 eq) was dissolved in 1,4-dioxane (10 mL), and then A5 (100 mg, 0.36 mmol, 1.0 equiv.), potassium carbonate (99 mg, 0.72 mmol, 2 equiv.) and $Pd(PPh_3)_4$ (41 mg, 0.036 mmol, 0.1 eq) were added, and the reaction was stir at 95° C. for 4 hours. The reaction was shown to be completed by TLC. The reaction system was loaded on crude silica gel, and separated by column chromatography (eluent system: DCM/EA=3:1) to provide compound A6 (60 mg, 64%).

6-(2-(((4-((2-methoxyethyl)amino)cyclohexyl)amino)pyrimidin-4-yl)-3,4-dihydro isoquinolin-1(2H)-one (1): Compound A6 (50 mg, 0.19 mmol, 1.0 equiv.), A3 (56 mg, 0.22 mmol, 1.2 equiv.), DIEA (73 mg, 0.57 mmol, 3.0 equiv.) and DMSO (2 mL) were added to a bottle respectively, and stirred overnight at 125° C. LC-MS showed that the raw materials have been consumed. The resultant was added with water, extracted with dichloromethane, dried over anhydrous sodium sulfate, and then filtered, concentrated. The residue was separated by column (eluent system: DCM/MeOH=30:1) to provide target compound 1 (white solid, 30 mg, 40%). MS: (M+1) 396.2. $^{1}$H NMR (500 MHz, DMSO-d6) δ 8.37 (s, 1H), 8.08-7.97 (m, 3H), 7.94 (d, J=8.0 Hz, 1H), 7.15 (t, J=6.5 Hz, 2H), 3.74 (s, 1H), 3.41 (s, 4H), 3.26 (s, 3H), 2.98 (t, J=6.6 Hz, 2H), 2.75 (d, J=5.7 Hz, 2H), 2.46 (s, 1H), 1.95 (s, 4H), 1.35-1.27 (m, 2H), 1.16 (s, 2H).

The following Examples 2-25 were synthesized in a similar way as Example 1 unless otherwise specified.

Example 2: 6-(5-chloro-2-(((1r,4r)-4-((2-methoxyethyl)amino)cyclohexyl)amino) pyrimidin-4-yl)-3,4-dihydroisoquinolin-1(2H)-one 2

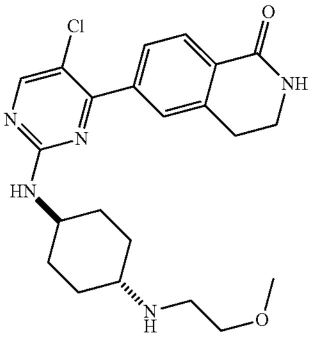

MS(ESI) m/z(M+1)+: 430.2.

Example 3: 6-(5-fluoro-2-(((1r,4r)-4-((2-methoxyethyl)amino)cyclohexyl)amino) pyrimidin-4-yl)-3,4-dihydroisoguinolin-1(2H)-one 3

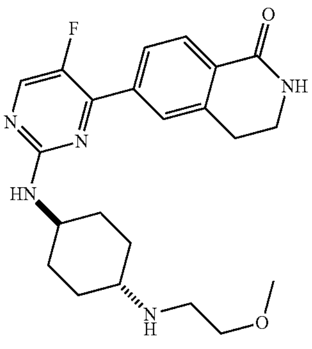

MS(ESI) m/z(M+1)+: 414.22.

Example 4: 6-(2-(((1r,4r)-4-((2-methoxyethyl) amino)cyclohexyl)amino)pyrimidin-4-yl)-2-methyl-3,4-dihydroisoquinolin-1(2H)-one 4

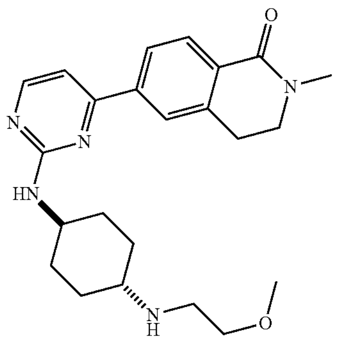

MS(ESI) m/z(M+1)+: 410.26.

Example 5: 5-(2-(((1r,4r))-4-((2-methoxyethyl) amino)cyclohexyl)amino)pyrimidin-4-yl)isoindo-line-1-one 5

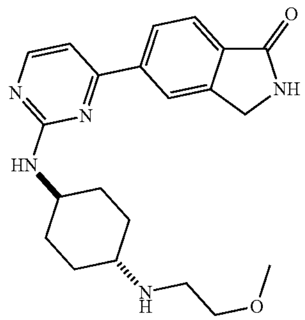

MS(ESI) m/z(M+1)+: 382.22.

Example 6: 6-(2-(((1r,4r)-4-((2-methoxyethyl) amino)cyclohexyl)amino)-5-methylpyridin-4-yl)-4,4-dimethyl-3,4-dihydroisoquinolin-1(2H)-one 6

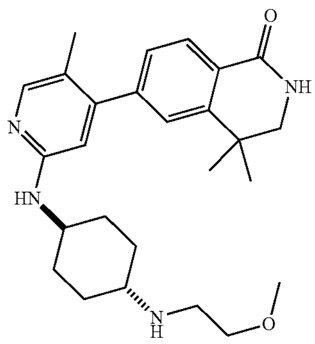

The synthesis of compound 6 was completed by using steps similar to those described in Example 1, replacing 2,4-dichloropyrimidine with 4-bromo-2-fluoro-5-methylpyridine. MS(ESI) m/z(M+1)+: 437.29.

Example 7: 6-(2-(((1r,4r)-4-((2-methoxyethyl) amino)cyclohexyl)amino)-5-methylpyrimidin-4-yl)-34-dihydroisoquinolin-1(2H)-one 7

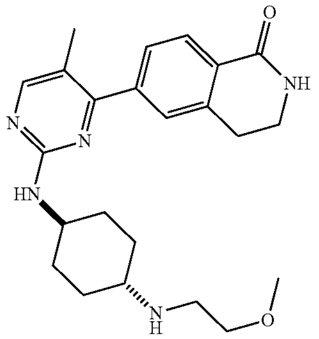

MS(ESI) m/z(M+1)+: 410.26.

Example 8: 6-(5-chloro-2-(((1r,4r)-4-((2-methoxy-ethyl)amino)cyclohexyl)amino) pyridin-4-yl)-3,4-dihydroisoquinolin-1(2H)-one 8

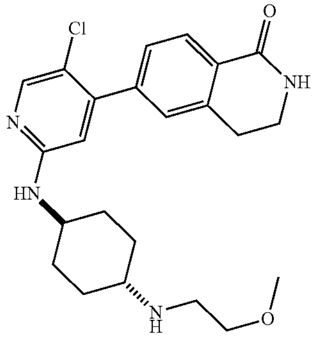

The compound of Example 8 was synthesized by using steps similar to those described in Example 6. MS(ESI) m/z(M+1)+: 429.21.

Example 9: 2-(((1r,4r)-4-((2-methoxyethyl)amino) cyclohexyl)amino)-4-(1-oxo-1,2,3,4-tetrahydroiso-quinolin-6-yl)pyrimidine-5-carbonitrile 9

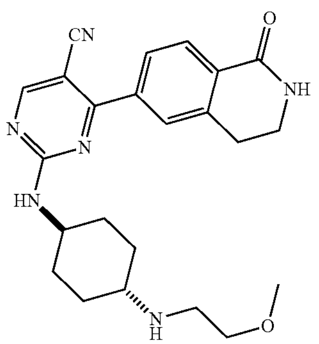

MS(ESI) m/z(M+1)+: 421.24.

Example 10: 6-(5-chloro-2-(((1r,4r)-4-((2-methoxyethyl)amino)cyclohexyl)amino) pyridin-4-yl)-4,4-dimethyl-3,4-dihydroisoquinolin-1(2H)-one 10

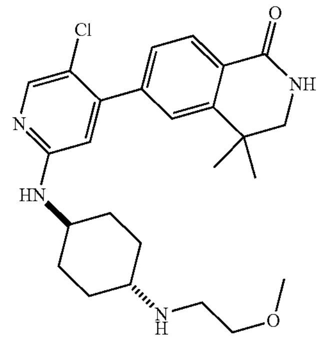

The compound of Example 10 was synthesized by using steps similar to those described in Example 6. MS(ESI) m/z(M+1)+: 457.24.

Example 11: 6-(2-(((1r,4r)-4-((2-methoxyethyl) amino)cyclohexyl)amino)pyrimidin-4-yl)-4,4-dimethyl-3,4-dihydroisoquinolin-1(2H)-one 11

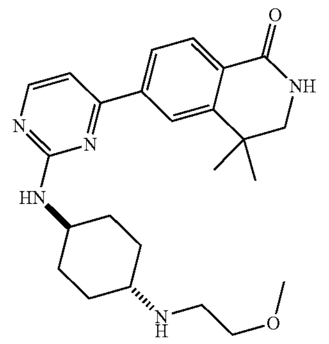

MS(ESI) m/z(M+1)+: 424.27.

Example 12: 6'-(2-(((1r,4r)-4-((2-methoxyethyl) amino)cyclohexyl)amino) pyrimidin-4-yl)-2',3'-dihydron-1'H-spiro[cyclopropane-1,4'-isoquinoline]-1'-one 12

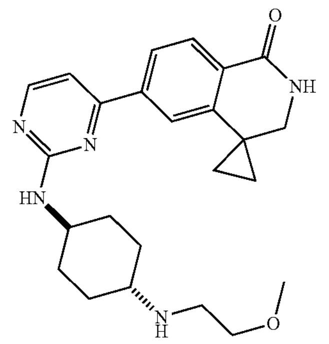

MS(ESI) m/z(M+1)+: 422.26.

Example 13: 4,4-diethyl-6-(2-(((1r,4r)-4-((2-methoxyethyl)amino)cyclohexyl) amino)pyrimidin-4-yl)-3,4-dihydroisoquinolin-1(2H)-one 13

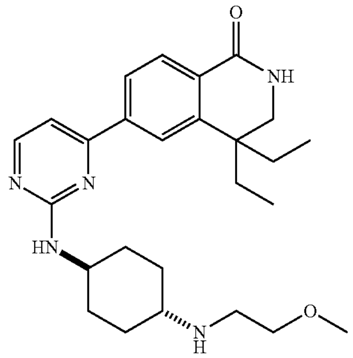

MS(ESI) m/z(M+1)+: 452.30.

Example 14: 4,4-diisopropyl-6-(2-(((1r,4r)-4-((2-methoxyethyl)amino)cyclohexyl) amino)pyrimidin-4-yl)-3,4-dihydroisoquinolin-1(2H)-one 14

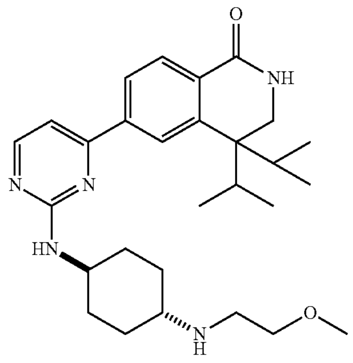

MS(ESI) m/z(M+1)+: 480.33.

Example 15: 6-(5-chloro-2-(((1r,4r)-4-((2-methoxyethyl)amino)cyclohexyl)amino) pyrimidin-4-yl)-4,4-dimethyl-3,4-dihydroisoquinolin-1(2H)-one 15

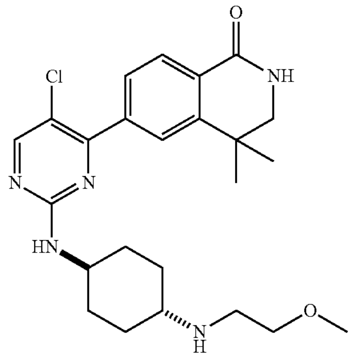

MS(ESI) m/z(M+1)+: 458.23.

Example 16: 6-(5-fluoro-2-(((1r,4r)-4-((2-methoxyethyl)amino)cyclohexyl)amino) pyrimidin-4-yl)-4,4-dimethyl-3,4-dihydroisoquinolin-1(2H)-one 16

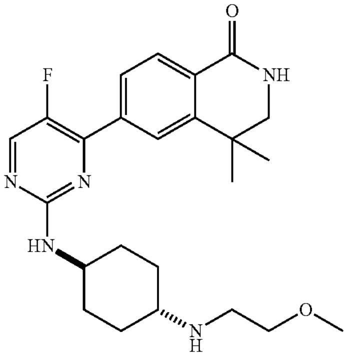

MS(ESI) m/z(M+1)+: 442.26.

Example 17: 6-(2-(((1r,4r)-4-((2-methoxyethyl) amino)cyclohexyl)amino)-5-methylpyrimidin-4-yl)-4,4-dimethyl-3,4-dihydroisoquinolin-1(2H)-one 17

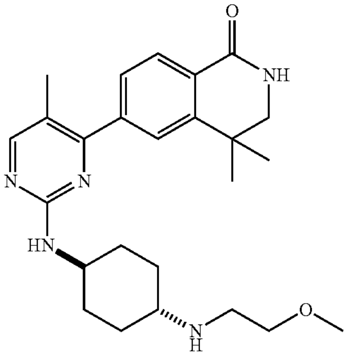

MS(ESI) m/z(M+1)+: 438.29.

Example 18: 6-(2-(((1r,4r)-4-((2-methoxyethyl) amino)cyclohexyl)amino)pyrimidin-4-yl)-2,4,4-trimethyl-3,4-dihydroisoquinolin-1(2H)-one 18

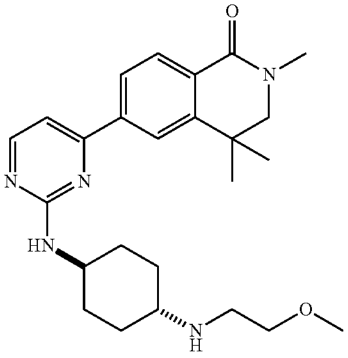

MS(ESI) m/z(M+1)+: 424.27.

Example 19: 6-(5-chloro-2-(((1r,4r)-4-((2-methoxyethyl)amino)cyclohexyl)amino) pyrimidin-4-yl)-2,4,4-trimethyl-3,4-dihydroisoquinolin-1(2H)-one 19

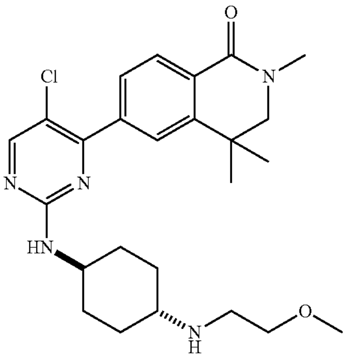

MS(ESI) m/z(M+1)+: 472.25.

Example 20: 5-(5-fluoro-2-(((1r,4r)-4-((2-methoxyethyl)amino)cyclohexyl)amino) pyrimidin-4-yl)-3,3-dimethylisoindoline-1-one 20

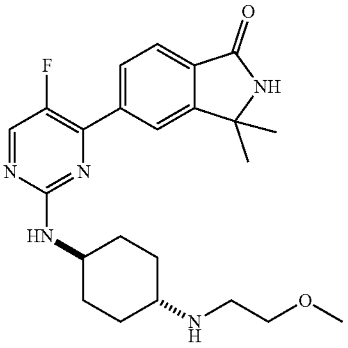

MS(ESI) m/z(M+1)+: 428.25.

Example 21: 5-(2-(((1r,4r)-4-((2-methoxyethyl) amino)cyclohexyl)amino)pyrimidin-4-yl)-3,3-dimethylisoindoline-1-one 21

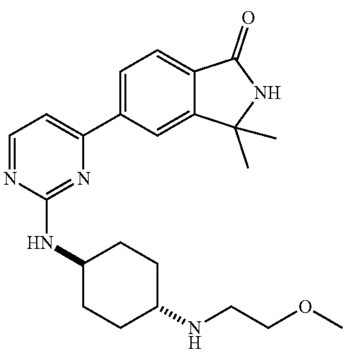

MS(ESI) m/z(M+1)+: 410.26.

Example 22: 5-(5-chloro-2-(((1r,4r)-4-((2-methoxyethyl)amino)cyclohexyl)amino) pyrimidin-4-yl)-3,3-dimethylisoindoline-1-one 22

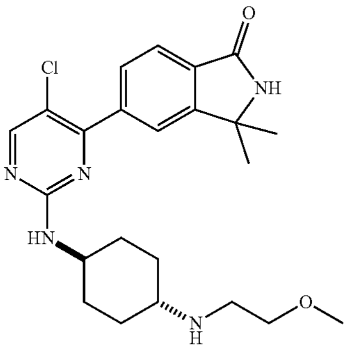

MS(ESI) m/z(M+1)+: 444.22.

Example 23: 5-(2-(((1r,4r)-4-((2-methoxyethyl) amino)cyclohexyl)amino)pyrimidin-4-yl)-2,3,3-trimethylisoindoline-1-one 23

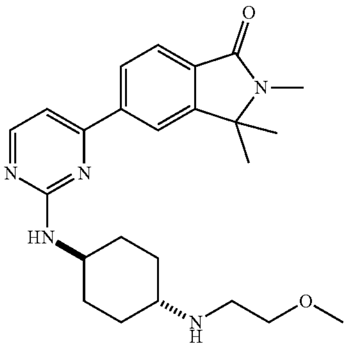

MS(ESI) m/z(M+1)+: 424.27.

Example 24: 5-(5-chloro-2-(((1r,4r)-4-((2-methoxyethyl)amino)cyclohexyl)amino) pyrimidin-4-yl)-2,3,3-trimethylisoindoline-1-one 24

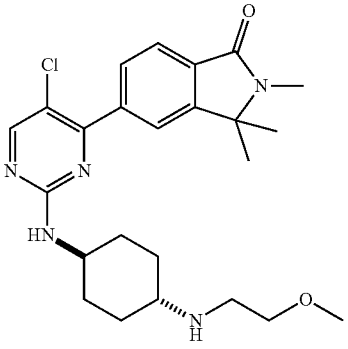

MS(ESI) m/z(M+1)+: 458.23.

Example 25: 6'-(2-(((1r,4r)-4-((2-methoxyethyl) amino)cyclohexyl)amino) pyrimidin-4-yl)-2',3'-dihydro-1'H-spiro[cyclobutane-1,4'-isoquinoline]-1'-one 25

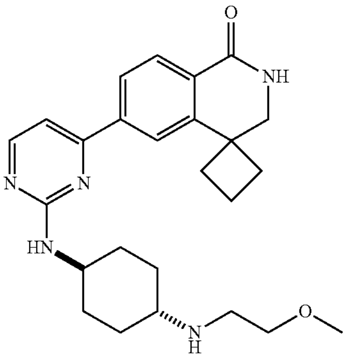

MS(ESI) m/z(M+1)+: 436.27.

Example 26: Synthesis of 3-((4-(4,4-dimethyl-1-oxo-1,2,3,4-tetrahydroisoquinolin-6-yl)pyrimidin-2-yl)amino)benzenesulfonamide 26

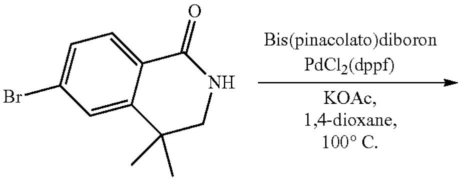

A7

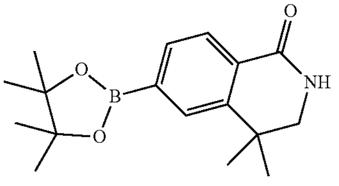

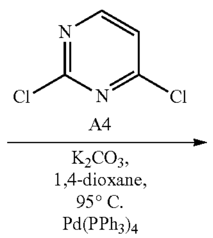

A8

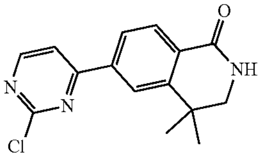

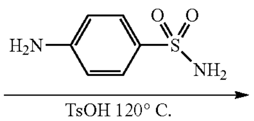

A9

-continued

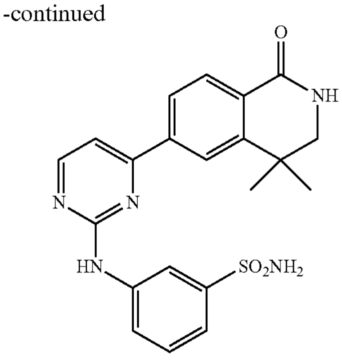

26

4,4-dimethyl-6-(4,4,5,5-tetramethyl-1,3,2-dioxaborolan-2-yl)-3,4-dihydroisoquinol in-1(2H)-one (A8): Compound A7 (1.0 g, 3.93 mmol), bis(pinacolato)diboron (1.2 g, 4.72 mmol, 1.2 equiv.), potassium acetate (0.77 g, 7.86 mmol, 2 equiv.) and $PdCl_2$(dppf) (0.32 g, 0.39 mmol, 0.1 equiv.) were added to 1,4-dioxane (20 mL) and stirred at 100° C. for 5 hours. The reaction was stopped after TLC monitoring, showing no starting material remained. The reaction solution was cooled to room temperature, and loaded on silica gel for column chromatography (eluent system: DCM/EA=3:1) to obtain reddish-brown solid A8 (0.9 g, 76%).

6-(2-chloropyrimidin-4-yl)-4,4-dimethyl-3,4-dihydroisoquinolin-1(2H)-one (A9): A8 (300 mg, 0.99 mmol, 1.0 eq) was dissolved in 1,4-dioxane (10 mL), which was then added with A4 (178 mg, 1.19 mmol, 1.2 equiv.), potassium carbonate (0.27 g, 1.98 mmol, 2 equiv.) and $Pd(PPh_3)_4$ (0.11 g, 0.099 mmol, 0.1 eq), and stirred at 95° C. for 4 hours. TLC showed that the reaction has been completed. The system was loaded on crude silica gel for column chromatography (eluent system: DCM/EA=3:1) to obtain the target compound A9 (130 mg, 45%).

3-((4-(4,4-dimethyl-1-oxo-1,2,3,4-tetrahydroisoquinolin-6-yl)pyrimidin-2-yl)amin o)benzenesulfonamide (26): Compound A9 (50 mg, 0.17 mmol, 1.0 equiv.), 4-aminobenzenesulfonamide (30 mg, 0.17 mmol, 1.0 equiv.), p-toluenesulfonic acid (29 mg, 0.17 mmol, 1.0 equiv.) and sec-butanol (2 mL) were added to a bottle respectively, and stirred overnight at 120° C. After filtration, the filter cake was washed with a small amount of methanol and methyl tert-butyl ether to obtain a light yellow solid. The solid was transferred into a vial, added with saturated sodium bicarbonate solution and stirred, and finally filtered. The solid was washed with methanol and methyl tert-butyl ether to obtain target compound 26 (white solid, 30 mg, 41%). MS: (M+1): 424.14. 1H NMR (500 MHz, DMSO-$d_6$) δ 10.08 (s, 1H), 8.65 (d, J=5.2 Hz, 1H), 8.54 (s, 1H), 8.20-8.18 (m, 2H), 8.10 (s, 1H), 8.01 (d, J=8.1 Hz, 1H), 7.97-7.94 (m, 1H), 7.59 (d, J=5.2 Hz, 1H), 7.52-7.44 (m, 2H), 7.31 (s, 2H), 3.23 (d, J=3.0 Hz, 2H), 1.37 (s, 6H).

The following Examples 27-95 and 99-101 were synthesized in a similar way as Example 26 unless otherwise specified.

Example 27: (3-((4-(4,4-dimethyl-1-oxo-1,2,3,4-tetrahydroisoquinolin-6-yl) pyrimidin-2-yl)amino) phenyl)methanesulfamide 27

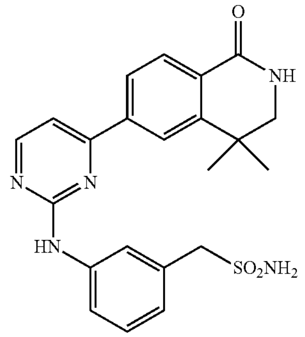 [SMILES: CC1(C)CNC(=O)c2ccc(-c3ccnc(Nc4cccc(CS(N)(=O)=O)c4)n3)cc21]

MS(ESI) m/z(M+1)+: 438.16.

Example 28: 4,4-dimethyl-6-(2-((3-((methylsulfonyl)methyl)phenyl)amino) pyrimidin-4-yl)-3,4-dihydroisoquinolin-1(2H)-one 28

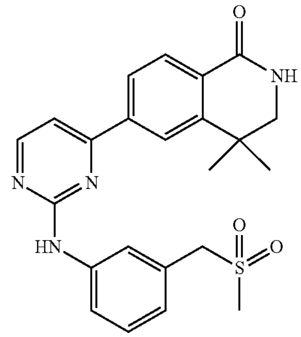

MS(ESI) m/z(M+1)+: 437.16.

Example 29: 3-((4-(4,4-dimethyl-1-oxo1,2,3,4-tetrahydroisoquinolin-6-yl) pyrimidin-2-yl)amino)-N,N-dimethylbenzenesulfonamide 29

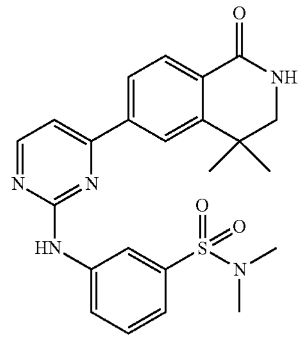

MS(ESI) m/z(M+1)+: 452.18.

Example 30: 4,4-dimethyl-6-(2-((3-(morpholinosulfonyl)phenyl)amino)pyrimidin-4-yl)-3,4-dihydroisoquinolin-1(2H)-one 30

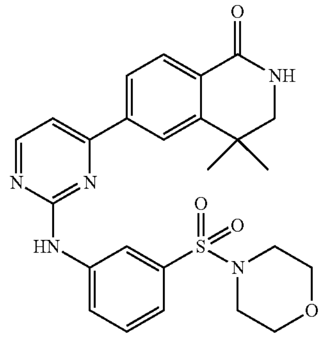 [SMILES: CC1(C)CNC(=O)c2ccc(-c3ccnc(Nc4cccc(S(=O)(=O)N5CCOCC5)c4)n3)cc21]

MS(ESI) m/z(M+1)+: 494.19.

Example 31: 3-((4-(4,4-dimethyl-1-oxo-1,2,3,4-tetrahydroisoquinolin-6-yl) pyrimidin-2-yl)amino)-N-methylbenzenesulfonamide 31

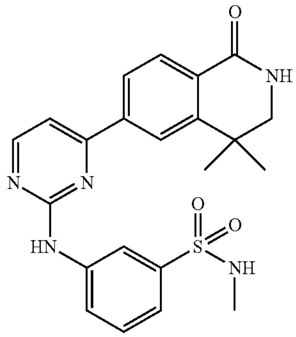 [SMILES: CNS(=O)(=O)c1cccc(Nc2nccc(-c3ccc4c(c3)C(C)(C)CNC4=O)n2)c1]

MS(ESI) m/z(M+1)+: 438.16.

Example 32: 4,4-dimethyl-6-(2-((3-(methylsulfonyl) phenyl)amino)pyrimidin-4-yl)-3,4-dihydroisoquinolin-1(2H)-one 32

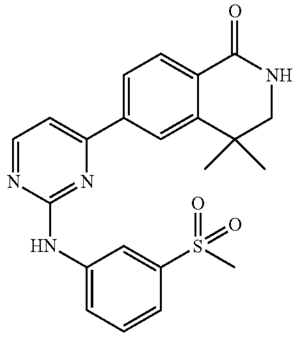 [SMILES: CC1(C)CNC(=O)c2ccc(-c3ccnc(Nc4cccc(S(C)(=O)=O)c4)n3)cc21]

MS(ESI) m/z(M+1)+: 423.15.

Example 33: 3-((4-(4,4-dimethyl-1-oxo-1,2,3,4-tetrahydroisoquinolin-6-yl) pyrimidin-2-yl)amino)-N-(1-methylpiperidin-4-yl)benzamide 33

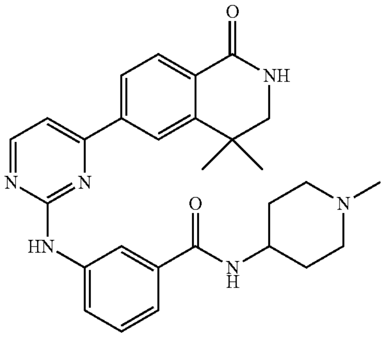 [SMILES: CN1CCC(NC(=O)c2cccc(Nc3nccc(-c4ccc5c(c4)C(C)(C)CNC5=O)n3)c2)CC1]

MS(ESI) m/z(M+1)+: 485.27.

Example 34: N-(5-((4-(4,4-dimethyl-1-oxo-1,2,3,4-tetrahydroisoquinolin-6-yl) pyrimidin-2-yl)amino)-2-fluorophenyl)methanesulfamide 34

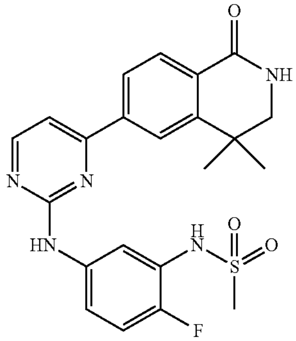 [SMILES: CC1(C)CNC(=O)c2ccc(-c3ccnc(Nc4ccc(F)c(NS(C)(=O)=O)c4)n3)cc21]

MS(ESI) m/z(M+1)+: 456.15.

Example 35: 6-(2-((3-(1,4-homopiperazin-1-yl)phenyl)amino)pyrimidin-4-yl)-4,4-dimethyl-3,4-dihydroisoquinolin-1(2H)-one 35

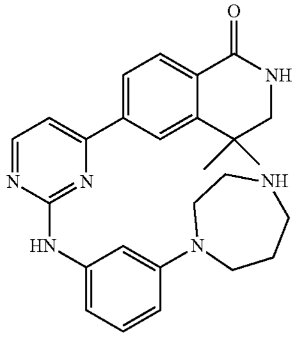 [SMILES: CC1(C)CNC(=O)c2ccc(-c3ccnc(Nc4cccc(N5CCCNCC5)c4)n3)cc21]

MS(ESI) m/z(M+1)+: 443.26.

Example 36: 6-(2-((4-fluoro-3-((methylsulfonyl)methyl)phenyl)amino)pyrimidin-4-yl)-4,4-dimethyl-3,4-dihydroisoquinolin-1(2H)-one 36

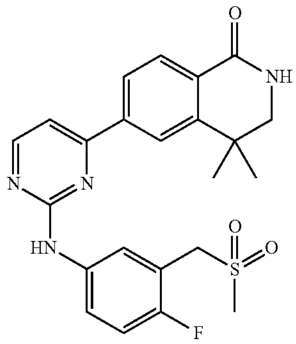 [SMILES: CC1(C)CNC(=O)c2ccc(-c3ccnc(Nc4ccc(F)c(CS(C)(=O)=O)c4)n3)cc21]

MS(ESI) m/z(M+1)+: 455.16.

Example 37: 4,4-dimethyl-6-(2-((3-(4-methylpiperazin-1-yl)phenyl)amino) pyrimidin-4-yl)-3,4-dihydroisoquinolin-1(2H)-one 37

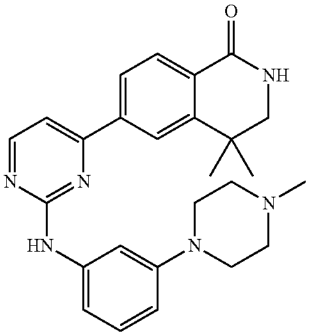 [SMILES: CN1CCN(c2cccc(Nc3nccc(-c4ccc5c(c4)C(C)(C)CNC5=O)n3)c2)CC1]

MS(ESI) m/z(M+1)+: 433.26.

Example 38: 4,4-dimethyl-6-(2-((3-(S-methylsulfonamide)phenyl)amino)pyrimidin-4-yl)-3,4-dihydroisoquinolin-1(2H)-one 38

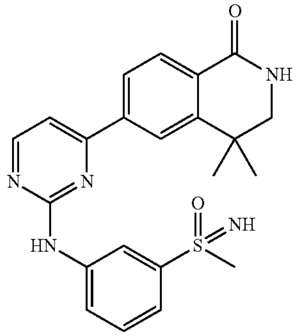 [SMILES: CC1(C)CNC(=O)c2ccc(-c3ccnc(Nc4cccc(S(C)(=N)=O)c4)n3)cc21]

MS(ESI) m/z(M+1)+: 422.17.

Example 39: 4,4-dimethyl-6-(2-((4-(methylsulfonyl)phenyl)amino)pyrimidin-4-yl)-3,4-dihydroisoquinolin-1(2H)-one 39

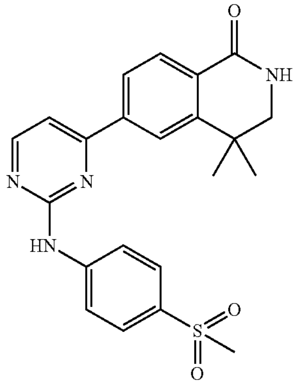 [SMILES: CC1(C)CNC(=O)c2ccc(-c3ccnc(Nc4ccc(S(C)(=O)=O)cc4)n3)cc21]

MS(ESI) m/z(M+1)+: 423.15.

Example 40: 4,4-dimethyl-6-(2-((4-(4-methylpiperazin-1-yl)phenyl)amino) pyrimidin-4-yl)-3,4-dihydroisoquinolin-1(2H)-one 40

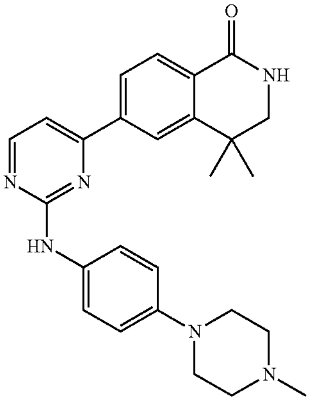 [SMILES: CN1CCN(c2ccc(Nc3nccc(-c4ccc5c(c4)C(C)(C)CNC5=O)n3)cc2)CC1]

MS(ESI) m/z(M+1)+: 443.26.

Example 41: 5-((4-(4,4-dimethyl-1-oxo-1,2,3,4-tetrahydroisoquinolin-6-yl) pyrimidin-2-yl)amino-2-fluoro-N-(1-methylpiperidin-4-yl)benzamide 41

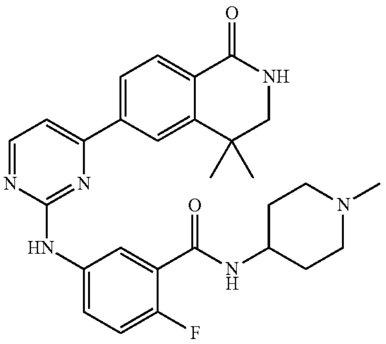 [SMILES: CN1CCC(NC(=O)c2cc(Nc3nccc(-c4ccc5c(c4)C(C)(C)CNC5=O)n3)ccc2F)CC1]

MS(ESI) m/z(M+1)+: 503.26.

Example 42: 4,4-dimethyl-6-(2-((4-methyl-3-((methylsulfonyl)methyl)phenyl) amino)pyrimidin-4-yl)-3,4-dihydroisoquinolin-1(2H)-one 42

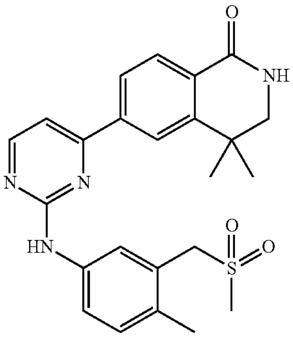 [SMILES: Cc1ccc(Nc2nccc(-c3ccc4c(c3)C(C)(C)CNC4=O)n2)cc1CS(C)(=O)=O]

MS(ESI) m/z(M+1)+: 451.18.

Example 43: 6-(2-((2,4-difluoro-5-((methylsulfonyl) methyl)phenyl)amino) pyrimidin-4-yl)-4,4-dimethyl-3,4-dihydroisoquinolin-1(2H)-one 43

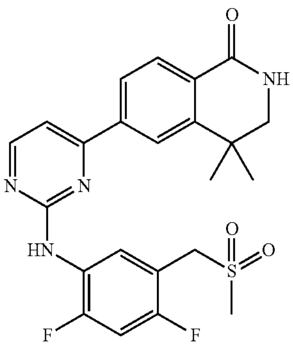 [SMILES: CC1(C)CNC(=O)c2ccc(-c3ccnc(Nc4cc(CS(C)(=O)=O)c(F)cc4F)n3)cc21]

MS(ESI) m/z(M+1)+: 473.15.

Example 44: 4,4-dimethyl-6-(2-((3-((methylsulfonyl)methyl)-4-(trifluoromethyl) phenyl)amino)pyrimidin-4-yl)-3,4-dihydroisoquinolin-1(2H)-one 44

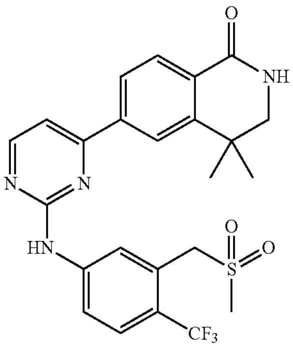 [SMILES: CC1(C)CNC(=O)c2ccc(-c3ccnc(Nc4ccc(C(F)(F)F)c(CS(C)(=O)=O)c4)n3)cc21]

MS(ESI) m/z(M+1)+: 505.15.

Example 45: 6-(2-((4-methoxy-3-((methylsulfonyl) methyl)phenyl)amino) pyrimidin-4-yl)-4,4-dimethyl-3,4-dihydroisoquinolin-1(2H)-one 45

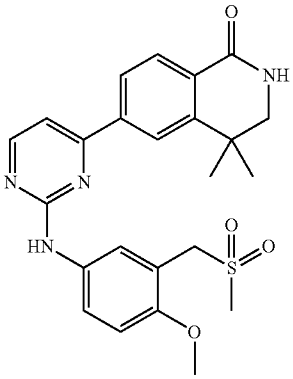 [SMILES: COc1ccc(Nc2nccc(-c3ccc4c(c3)C(C)(C)CNC4=O)n2)cc1CS(C)(=O)=O]

MS(ESI) m/z(M+1)+: 467.18.

Example 46: 6-(2-((4-fluoro-3-((methylsulfonyl) methyl)phenyl)amino)pyridin-4-yl)-4,4-dimethyl-3,4-dihydroisoquinolin-1(2H)-one 46

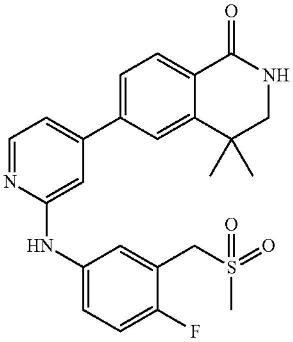 [SMILES: CC1(C)CNC(=O)c2ccc(-c3ccnc(Nc4ccc(F)c(CS(C)(=O)=O)c4)c3)cc21]

MS(ESI) m/z(M+1)+: 454.16.

Example 47: 4,4-dimethyl-6-(2-((2-((methylsulfonyl)methyl)pyridin-4-yl)amino) pyridin-4-yl)-3,4-dihydroisoquinolin-1(2H)-one 47

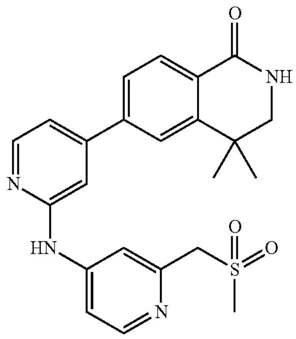 [SMILES: CC1(C)CNC(=O)c2ccc(-c3ccnc(Nc4ccnc(CS(C)(=O)=O)c4)c3)cc21]

MS(ESI) m/z(M+1)+: 437.16.

Example 48: 5-(2-((4-fluoro-3-((methylsulfonyl) methyl)phenyl)amino)pyrimidin-4-yl)-3,3-dimethylisoindoline-1-one 48

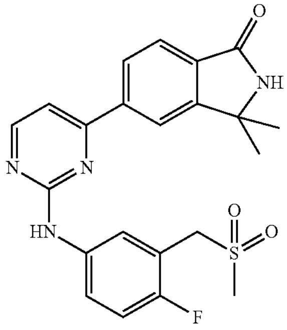 [SMILES: CC1(C)NC(=O)c2ccc(-c3ccnc(Nc4ccc(F)c(CS(C)(=O)=O)c4)n3)cc21]

MS(ESI) m/z(M+1)+: 441.14.

Example 49: 3,3-dimethyl-5-(2-((4-((methylsulfonyl)methyl)phenyl)amino) pyrimidin-4-yl)isoindoline-1-one 49

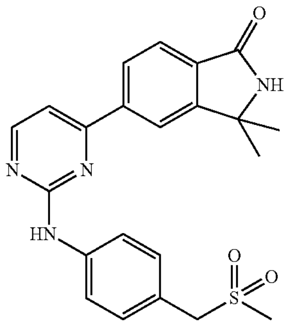 [SMILES: CC1(C)NC(=O)c2ccc(-c3ccnc(Nc4ccc(CS(C)(=O)=O)cc4)n3)cc21]

MS(ESI) m/z(M+1)+: 423.15.

Example 50: 5-(5-fluoro-2-((4-fluoro-3-((methylsulfonyl)methyl)phenyl)amino) pyrimidin-4-yl)-3,3-dimethylisoindoline-1-one 50

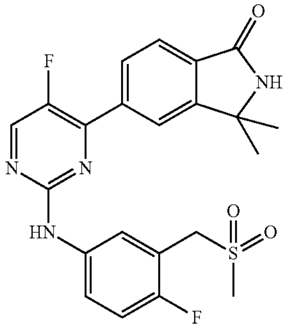 [SMILES: CC1(C)NC(=O)c2ccc(-c3nc(Nc4ccc(F)c(CS(C)(=O)=O)c4)ncc3F)cc21]

MS(ESI) m/z(M+1)+: 459.13.

Example 51: 5-(5-chloro-2-((4-fluoro-3-((methylsulfonyl)methyl)phenyl)amino) pyrimidin-4-yl)-3,3-dimethylisoindoline-1-one 51

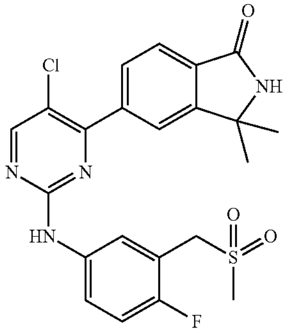 [SMILES: CC1(C)NC(=O)c2ccc(-c3nc(Nc4ccc(F)c(CS(C)(=O)=O)c4)ncc3Cl)cc21]

MS(ESI) m/z(M+1)+: 475.10.

Example 52: 5-(5-chloro-2-((2,4-difluoro-5-((methylsulfonyl)methyl)phenyl)amino) pyrimidin-4-yl)-3, 3-dimethylisoindoline-1-one 52

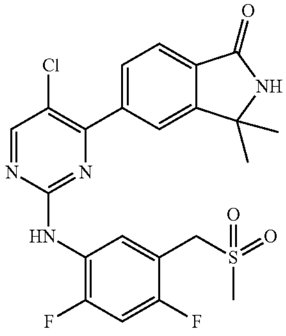 [SMILES: CC1(C)NC(=O)c2ccc(-c3nc(Nc4cc(CS(C)(=O)=O)c(F)cc4F)ncc3Cl)cc21]

MS(ESI) m/z(M+1)+: 493.09.

Example 53: 5-(2-((2,4-difluoro-5-((methylsulfonyl) methyl)phenyl)amino)-5-fluoropyrimidin-4-yl)-3,3-dimethylisoindoline-1-one 53

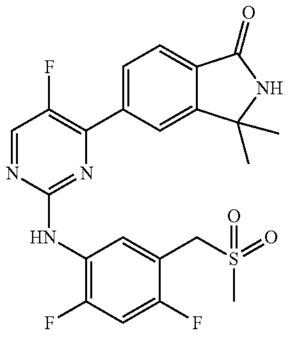

MS(ESI) m/z(M+1)+: 477.12.

Example 54: 5-(5-chloro-2-((4-methyl-3-((methyl-sulfonyl)methyl)phenyl)amino) pyrimidin-4-yl)-3,3-dimethylisoindoline-1-one 54

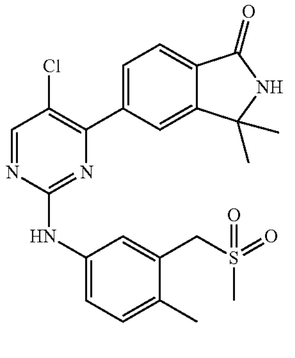

MS(ESI) m/z(M+1)+: 471.13.

Example 55: 5-(5-fluoro-2-((4-methyl-3-((methyl-sulfonyl)methyl)phenyl)amino) pyrimidin-4-yl)-3,3-dimethylisoindoline-1-one 55

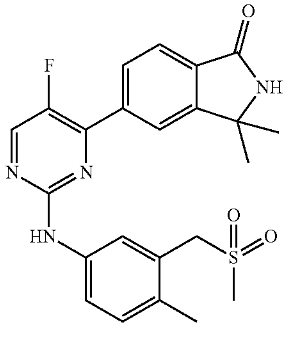 [SMILES: Cc1ccc(Nc2ncc(F)c(-c3ccc4c(c3)C(C)(C)NC4=O)n2)cc1CS(C)(=O)=O]

MS(ESI) m/z(M+1)+: 455.16.

Example 56: 4,4-dimethyl-6-(2-((2-((methylsulfonyl)methyl)pyridin-4-yl)amino) pyrimidin-4-yl)-3,4-dihydroisoquinolin-1(2H)-one 56

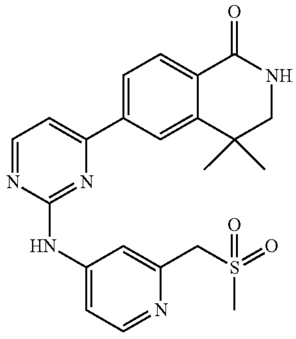

MS(ESI) m/z(M+1)+: 438.16.

Example 57: 4,4-dimethyl-6-(2-((4-((methylsulfonyl)methyl)pyridin-2-yl)amino) pyrimidin-4-yl)-3,4-dihydroisoquinolin-1(2H)-one 57

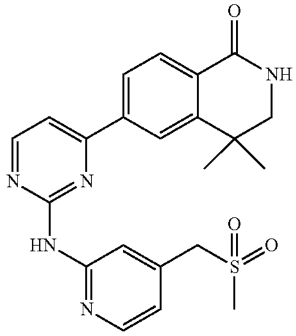

MS(ESI) m/z(M+1)+: 438.16.

Example 58: 4,4-dimethyl-6-(2-((4-((S-methylsulfonimide)methyl)pyridin-2-yl) amino)pyrimidin-4-yl)-3,4-dihydroisoquinolin-1(2H)-one 58

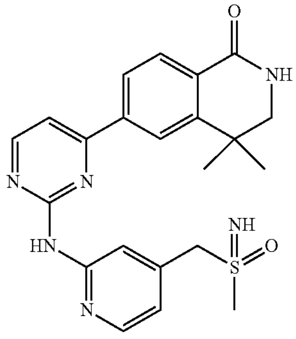

MS(ESI) m/z(M+1)+: 437.18.

Example 59: 4,4-dimethyl-6-(2-((4-(1-(methylsulfonyl)cyclopropyl)phenyl)amino) pyrimidin-4-yl)-3,4-dihydroisoquinolin-1(2H)-one 59

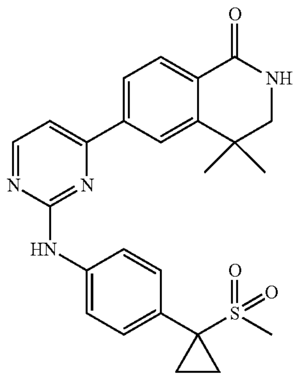 [SMILES: CC1(C)CNC(=O)c2ccc(-c3ccnc(Nc4ccc(C5(S(C)(=O)=O)CC5)cc4)n3)cc21]

MS(ESI) m/z(M+1)+: 463.18.

Example 60: 6-(5-chloro-2-((4-(1-(methylsulfonyl) cyclopropyl)phenyl)amino) pyrimidin-4-yl)-4,4-dimethyl-3,4-dihydroisoquinolin-1(2H)-one 60

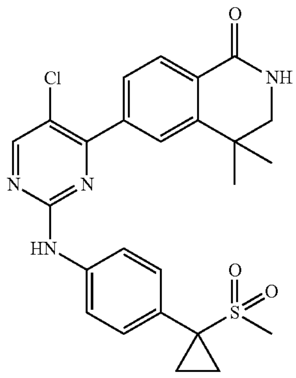

MS(ESI) m/z(M+1)+: 497.14.

Example 61: 6-(5-fluoro-2-((4-(1-(methylsulfonyl) cyclopropyl)phenyl)amino) pyrimidin-4-yl)-4,4-dimethyl-3,4-dihydroisoquinolin-1(2H)-one 61

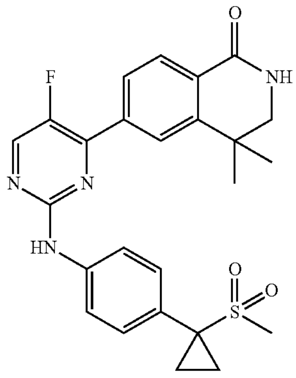

MS(ESI) m/z(M+1)+: 481.17.

Example 62: 6-(5-chloro-2-((4-fluoro-3-(1-(methylsulfonyl)cyclopropyl)phenyl) amino)pyrimidin-4-yl)-4,4-dimethyl-3,4-dihydroisoquinolin-1(2H)-one 62

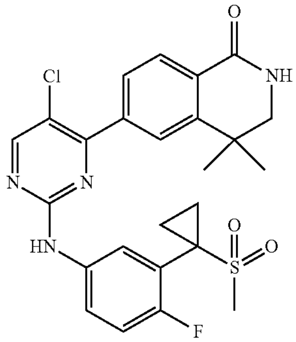

MS(ESI) m/z(M+1)+: 515.13.

Example 63: 6-(5-fluoro-2-((4-fluoro-3-(1-(methylsulfonyl)cyclopropyl)phenyl) amino)pyrimidin-4-yl)-4,4-dimethyl-3,4-dihydroisoquinolin-1(2H)-one 63

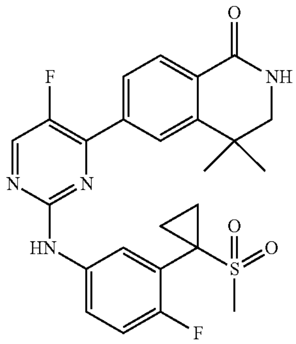

MS(ESI) m/z(M+1)+: 499.16.

Example 64: 6-(5-chloro-2-((2,4-difluoro-5-((methylsulfonyl)methyl)phenyl)amino) pyrimidin-4-yl)-4,4-dimethyl-3,4-dihydroisoquinolin-1(2H)-one 64

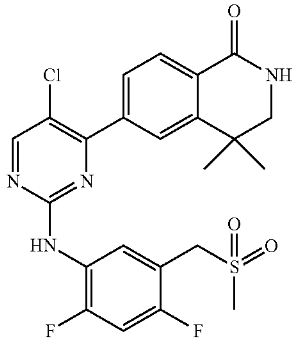 [SMILES: CC1(C)CNC(=O)c2ccc(-c3nc(Nc4cc(CS(C)(=O)=O)c(F)cc4F)ncc3Cl)cc21]

MS(ESI) m/z(M+1)+: 507.11.

Example 65: 6-(2-((4-fluoro-3-(1-(methylsulfonyl) cyclopropyl)phenyl)amino) pyrimidin-4-yl)-2,4,4-trimethyl-3,4-dihydroisoquinolin-1(2H)-one 65

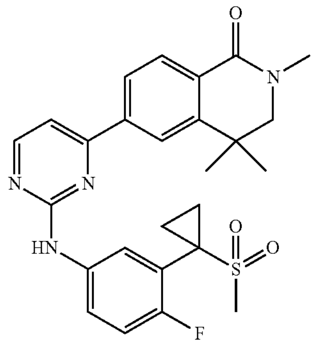

MS(ESI) m/z(M+1)+: 495.19.

Example 66: 6-(5-chloro-2-((4-fluoro-3-(1-(methylsulfonyl)cyclopropyl)phenyl) amino)pyrimidin-4-yl)-2,4,4-trimethyl-3,4-dihydroisoquinolin-1(2H)-one 66

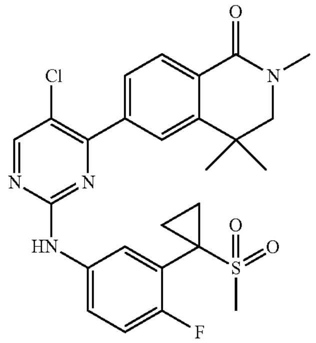

MS(ESI) m/z(M+1)+: 529.15.

Example 67: 6-(5-fluoro-2-((4-fluoro-3-(1-(methylsulfonyl)cyclopropyl)phenyl) amino)pyrimidin-4-yl)-2,4,4-trimethyl-3,4-dihydroisoquinolin-1(2H)-one 67

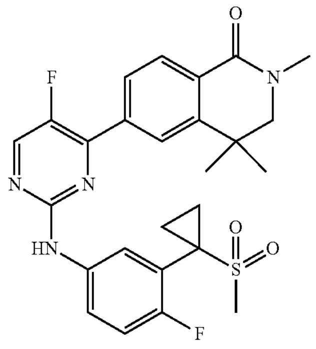

MS(ESI) m/z(M+1)+: 513.18.

Example 68: 6-(5-chloro-2-((3-(4-methylpiperazin-1-yl)phenyl)amino)pyrimidin-4-yl)-4,4-dimethyl-3,4-dihydroisoquinolin-1(2H)-one 68

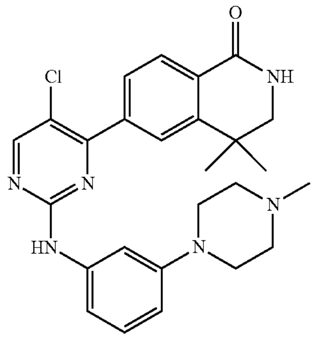

MS(ESI) m/z(M+1)+: 477.22.

Example 69: 6-(5-fluoro-2-((3-(4-methylpiperazin-1-yl)phenyl)amino)pyrimidin-4-yl)-4,4-dimethyl-3,4-dihydroisoquinolin-1(2H)-one 69

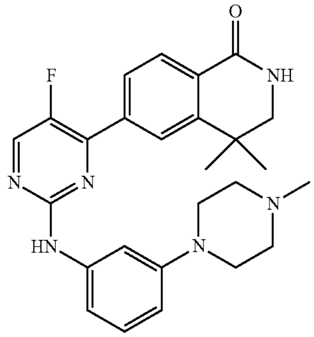

MS(ESI) m/z(M+1)+: 461.25.

Example 70: 4,4-dimethyl-6-(5-methyl-2-((3-(4-methylpiperazin-1-yl)phenyl) amino)pyrimidin-4-yl)-3,4-dihydroisoquinolin-1(2H)-one 70

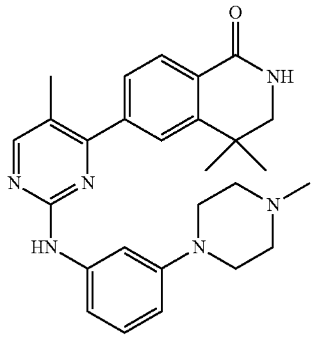

MS(ESI) m/z(M+1)+: 457.27.

Example 71: 6-(5-fluoro-2-((4-methyl-3-(4-methylpiperazin-1-yl)phenyl)amino) pyrimidin-4-yl)-4,4-dimethyl-3,4-dihydroisoquinolin-1(2H)-one 71

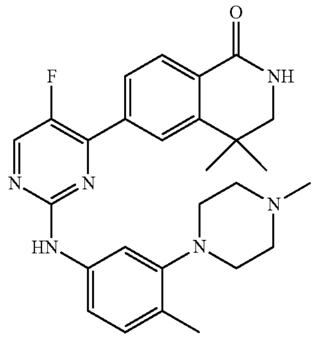

MS(ESI) m/z(M+1)+: 475.26.

Example 72: 6-(5-fluoro-2-((4-fluoro-3-(4-methylpiperazin-1-yl)phenyl)amino) pyrimidin-4-yl)-4,4-dimethyl-3,4-dihydroisoquinolin-1(2H)-one 72

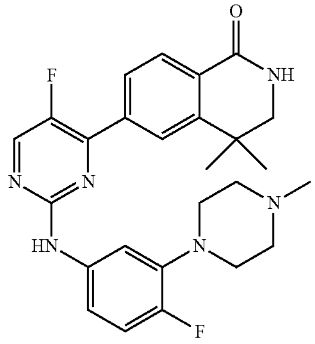

MS(ESI) m/z(M+1)+: 479.24.

Example 73: 6-(5-fluoro-2-((3-fluoro-5-(4-methylpiperazin-1-yl)phenyl)amino) pyrimidin-4-yl)-4,4-dimethyl-3,4-dihydroisoquinolin-1(2H)-one 73

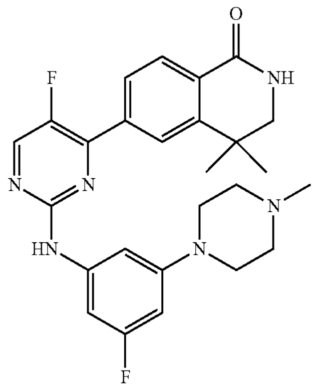 [SMILES: CN1CCN(c2cc(F)cc(Nc3ncc(F)c(-c4ccc5c(c4)C(C)(C)CNC5=O)n3)c2)CC1]

MS(ESI) m/z(M+1)+: 479.24.

Example 74: 6-(5-chloro-2-((4-methyl-3-(4-methylpiperazin-1-yl)phenyl)amino) pyrimidin-4-yl)-4,4-dimethyl-3,4-dihydroisoquinolin-1(2H)-one 74

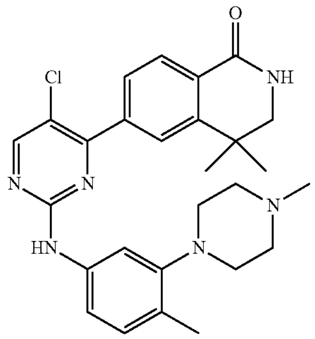

MS(ESI) m/z(M+1)+: 491.23.

Example 75: 6-(5-chloro-2-((4-fluoro-3-(4-methylpiperazin-1-yl)phenyl)amino) pyrimidin-4-yl)-4,4-dimethyl-3,4-dihydroisoquinolin-1(2H)-one 75

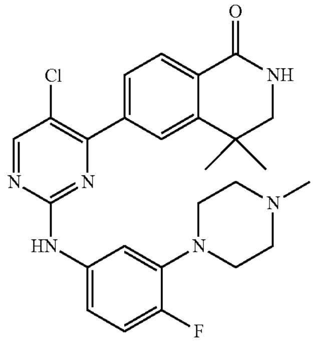

MS(ESI) m/z(M+1)+: 495.21.

Example 76: 6-(5-chloro-2-((3-(4-ethylpiperazin-1-yl)-4-fluorophenyl)amino) pyrimidin-4-yl)-4,4-dimethyl-3,4-dihydroisoquinolin-1(2H)-one 76

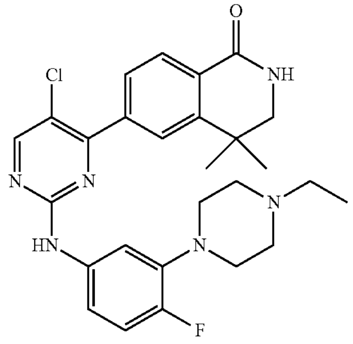 [SMILES: CCN1CCN(c2cc(Nc3ncc(Cl)c(-c4ccc5c(c4)C(C)(C)CNC5=O)n3)ccc2F)CC1]

MS(ESI) m/z(M+1)+: 509.22.

Example 77: 6-(5-chloro-2-((4-fluoro-3-(4-isopropylpiperazin-1-yl)phenyl)amino) pyrimidin-4-yl)-4,4-dimethyl-3,4-dihydroisoquinolin-1(2H)-one 77

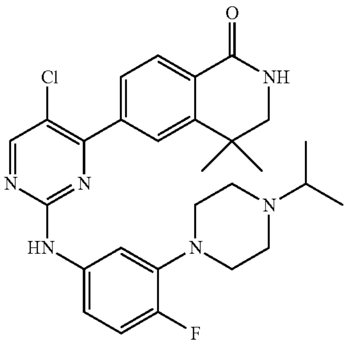 [SMILES: CC(C)N1CCN(c2cc(Nc3ncc(Cl)c(-c4ccc5c(c4)C(C)(C)CNC5=O)n3)ccc2F)CC1]

MS(ESI) m/z(M+1)+: 523.24.

Example 78: 6-(5-chloro-2-((3-(4-isopropylpiperazin-1-yl)-4-methylphenyl)amino) pyrimidin-4-yl)-4,4-dimethyl-3,4-dihydroisoquinolin-1(2H)-one 78

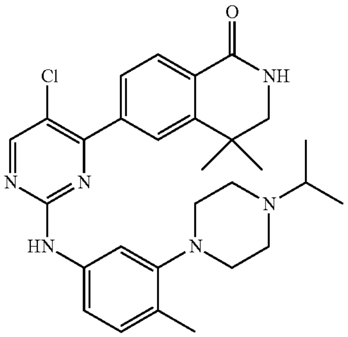 [SMILES: Cc1ccc(Nc2ncc(Cl)c(-c3ccc4c(c3)C(C)(C)CNC4=O)n2)cc1N1CCN(C(C)C)CC1]

MS(ESI) m/z(M+1)+: 519.26.

Example 79: 6-(2-((3-(4-ethylpiperazin-1-yl)-4-fluorophenyl)amino)5-fluoropyrimidin-4-yl)-4,4-dimethyl-3,4-dihydroisoquinolin-1(2H)-one 79

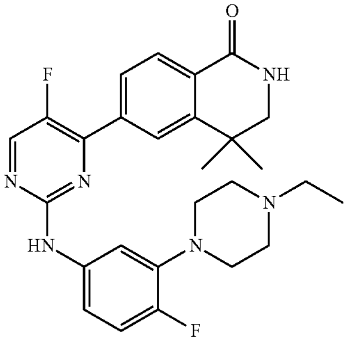 [SMILES: CCN1CCN(c2cc(Nc3ncc(F)c(-c4ccc5c(c4)C(C)(C)CNC5=O)n3)ccc2F)CC1]

MS(ESI) m/z(M+1)+: 493.25.

Example 80: 6-(5-fluoro-2-((4-fluoro-3-(4-isopropylpiperazin-1-yl)phenyl)amino) pyrimidin-4-yl)-4,4-dimethyl-3,4-dihydroisoquinolin-1(2H)-one 80

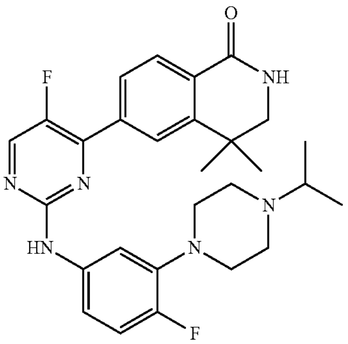 [SMILES: CC(C)N1CCN(c2cc(Nc3ncc(F)c(-c4ccc5c(c4)C(C)(C)CNC5=O)n3)ccc2F)CC1]

MS(ESI) m/z(M+1)+: 507.27.

Example 81: 6-(2-((4-fluoro-3-(4-methylpiperazin-1-yl)phenyl)amino)pyrimidin-4-yl)-4,4-dimethyl-3,4-dihydroisoquinolin-1(2H)-one 81

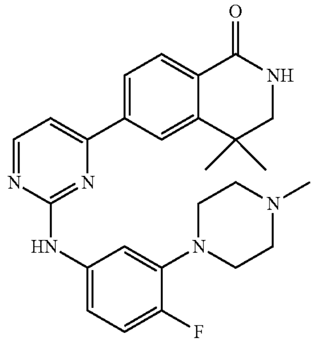 [SMILES: CN1CCN(c2cc(Nc3nccc(-c4ccc5c(c4)C(C)(C)CNC5=O)n3)ccc2F)CC1]

MS(ESI) m/z(M+1)+: 461.25.

Example 82: 4,4-methyl-6-(2-((4-methyl-3-(4-methylpiperazin-1-yl)phenyl)amino) pyrimidin-4-yl)-dihydroisoquinolin-1(2H)-one 82

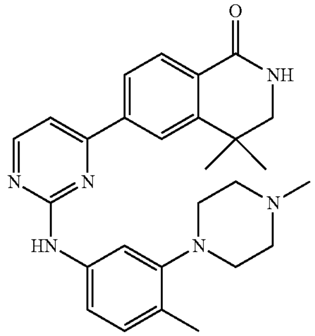 [SMILES: Cc1ccc(Nc2nccc(-c3ccc4c(c3)C(C)(C)CNC4=O)n2)cc1N1CCN(C)CC1]

MS(ESI) m/z(M+1)+: 457.27.

Example 83: 6-(5-fluoro-2-((4-(4-methylpiperazin-1-yl)phenyl)amino)pyrimidin-4-yl)-4,4-dimethyl-3,4-dihydroisoquinolin-1(2H)-one 83

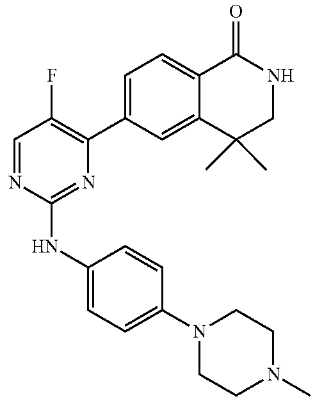

MS(ESI) m/z(M+1)+: 461.25.

Example 84: 6-(2-((3-(4-ethylpiperazin-1-yl)-4-fluorophenyl)amino)pyrimidin-4-yl)-4,4-dimethyl-3,4-dihydroisoquinolin-1(2H)-one 84

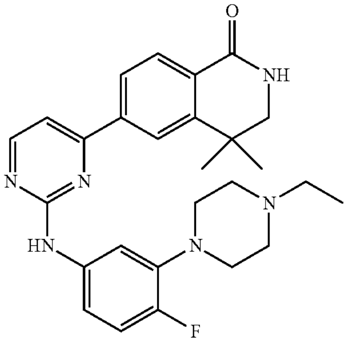 [SMILES: CCN1CCN(c2cc(Nc3nccc(-c4ccc5c(c4)C(C)(C)CNC5=O)n3)ccc2F)CC1]

MS(ESI) m/z(M+1)+: 475.26.

Example 85: 6-(2-((4-fluoro-3-(4-isopropylpiperazin-1-yl)phenyl)amino)pyrimidin-4-yl)-4,4-dimethyl-3,4-dihydroisoquinolin-1(2H)-one 85

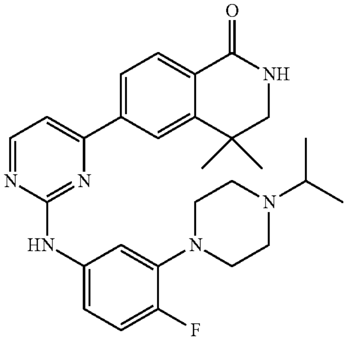 [SMILES: CC(C)N1CCN(c2cc(Nc3nccc(-c4ccc5c(c4)C(C)(C)CNC5=O)n3)ccc2F)CC1]

MS(ESI) m/z(M+1)+: 489.28.

Example 86: 6-(2-((3-(4-ethylpiperazin-1-yl)-4-methylphenyl)amino)pyrimidin-4-yl)-4,4-dimethyl-3,4-dihydroisoquinolin-1(2H)-one 86

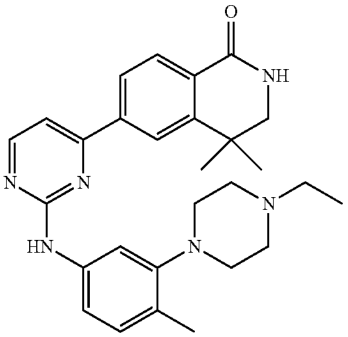

MS(ESI) m/z(M+1)+: 471.29.

Example 87: 6-(2-((3-(4-isopropylpiperazin-1-yl)-4-methylphenyl)amino) pyrimidin-4-yl)-4,4-dimethyl-3,4-dihydroisoquinolin-1(2H)-one 87

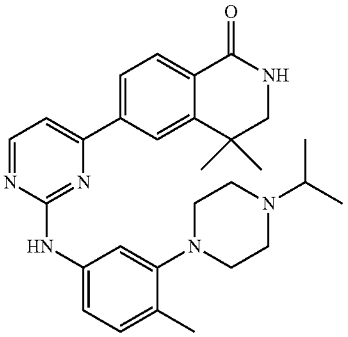 [SMILES: Cc1ccc(Nc2nccc(-c3ccc4c(c3)C(C)(C)CNC4=O)n2)cc1N1CCN(C(C)C)CC1]

MS(ESI) m/z(M+1)+: 485.30.

Example 88: 6-(5-chloro-2-((4-(4-methylpiperazin-1-yl)phenyl)amino)pyrimidin-4-yl)-4,4-dimethyl-3,4-dihydroisoquinolin-1(2H)-one 88

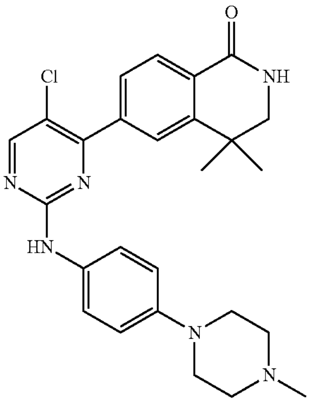

MS(ESI) m/z(M+1)+: 477.22.

Example 89: 6-(5-fluoro-2-((4-((methylsulfonyl)methyl)pyridin-2-yl)amino) pyrimidin-4-yl)-4,4-dimethyl-3,4-dihydroisoquinolin-1(2H)-one 89

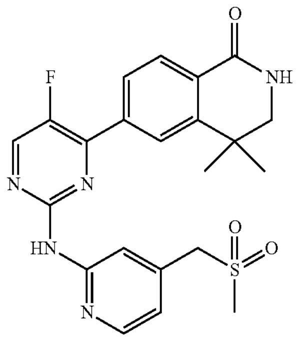

MS(ESI) m/z(M+1)+: 456.15.

Example 90: 6-(5-chloro-2-((4-((methylsulfonyl)methyl)pyridin-2-yl)amino) pyrimidin-4-yl)-4,4-dimethyl-3,4-dihydroisoquinolin-1(2H)-one 90

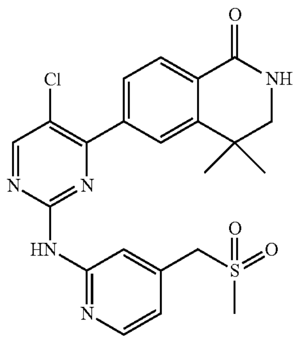

MS(ESI) m/z(M+1)+: 472.12.

Example 91: 4,4-dimethyl-6-(5-methyl-2-((4-((methylsulfonyl)methyl)pyridin-2-yl) amino)pyrimidin-4-yl)-3,4-dihydroisoquinolin-1(2H)-one 91

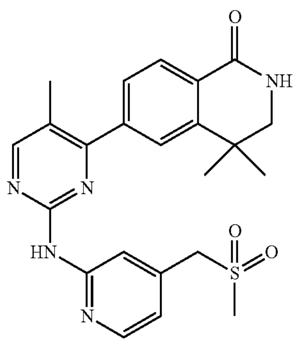

MS(ESI) m/z(M+1)+: 452.18.

Example 92: 4,4-dimethyl-6-(2-((4-((methylsulfonyl)methyl)pyridin-2-yl)amino)-5-(trifluoromethyl) pyrimidin-4-yl)-3,4-dihydroisoquinolin-1(2H)-one 92

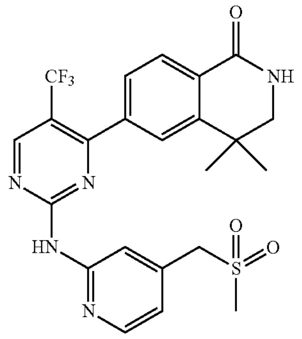

MS(ESI) m/z(M+1)+: 506.15.

Example 93: 6-(5-fluoro-2-((4-((S-methylsulfonimide)methyl)pyridin-2-yl)amino) pyrimidin-4-yl)-4,4-dimethyl-3,4-dihydroisoquinolin-1(2H)-one 93

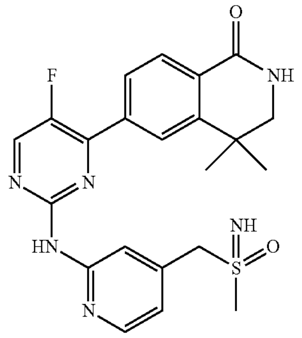

MS(ESI) m/z(M+1)+: 455.17.

Example 94: 6-(5-chloro-2-((4-((S-methylsulfonimide)methyl)pyridin-2-yl)amino) pyrimidin-4-yl)-4,4-dimethyl-3,4-dihydroisoquinolin-1(2H)-one 94

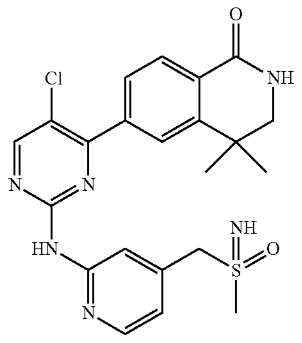

MS(ESI) m/z(M+1)+: 471.14.

Example 95: 4,4-dimethyl-6-(5-methyl-2-((4-((S-methylsulfonimide)methyl) pyridin-2-yl)amino)pyrimidin-4-yl)-4,4-dimethyl-3,4-dihydroisoquinolin-1 (2H)-one 95
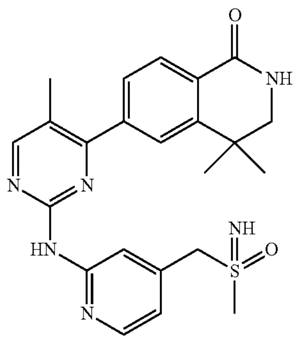
MS(ESI) m/z(M+1)+: 451.19.
Example 96: (1S,3R)-3-acetylamino-N-(5-chloro-4-(4,4-dimethyl-1-oxo-1,2,3,4-tetrahydroisoquinolin-6-yl)pyridin-2-yl)cyclohexyl-1-formamide 96
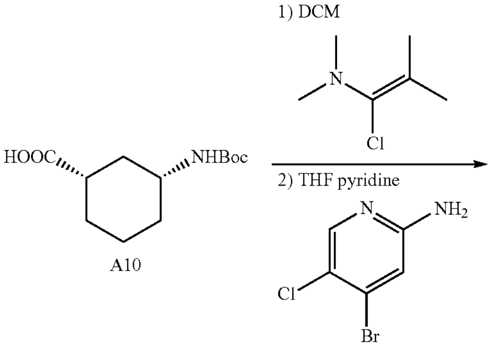
A10
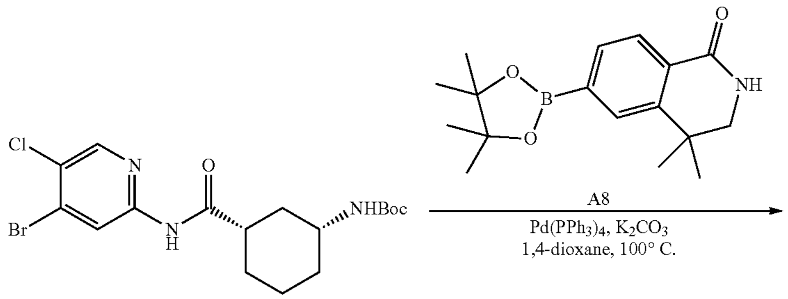
A11
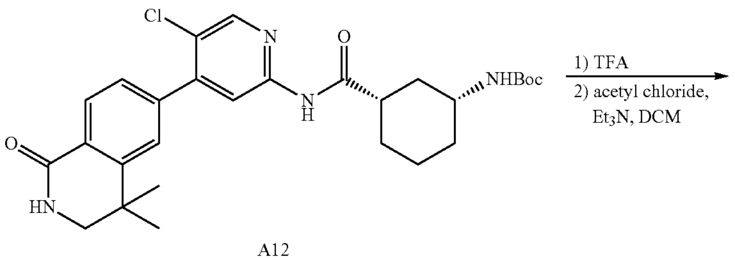
A12

-continued

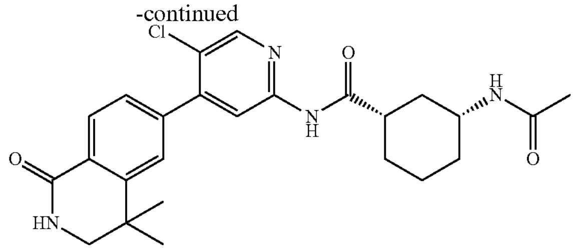

96 tert-Butyl ((1R,3S)-3-((4-bromo-5-chloropyridin-2-yl) carbamoyl)cyclohexyl) carbamate (A11): compound A10 (1.0 g, 4.11 mmol) was dissolved in dichloromethane, and then was dripped with 1-chloro-N,N,2-trimethyl propenylamine (0.82 g, 6.17 mmol, 1.5 equiv.) under ice bath. The reaction mixture was stirred continuously at 0° C. for 30 minutes. Then, 2-amino-4-bromo-5-chloropyridine (0.68 g, 3.28 mmol, 0.8 equiv.) and pyridine (0.32 g, 4.11 mmol, 1 equiv.) in tetrahydrofuran solution was added, and the resultant was stirred at room temperature for 3 hours. The reaction was stopped after TLC monitoring, showing no starting material remained. Saturated sodium carbonate solution was added, extracted with ethyl acetate, dried over anhydrous sodium sulfate, filtered, concentrated, and then loaded on silica gel for column chromatography (eluent system: PE/EA=3:1) to obtain white solid A11 (1.2 g, 68%).

tert-Butyl ((1R,3S)-3-((5-chloro-4-(4,4-dimethyl-1-oxo-1,2,3,4-tetrahydro isoquinolin-6-yl)pyridin-2-yl)carbamoyl) cyclohexyl)carbamate (A12): A11 (800 mg, 1.85 mmol, 1.0 eq) was dissolved in 1,4-dioxane (10 mL), then was added with A8 (613 mg, 2.03 mmol, 1.1 equiv.), potassium carbonate (0.51 g, 3.7 mmol, 2 equiv.) and $Pd(PPh_3)_4$ (0.21 g, 0.185 mmol, 0.1 eq), and stirred at 100° C. for 4 hours. TLC showed that the reaction has been completed. The reaction system was loaded on crude silica gel and separated by column chromatography (eluent system: DCM/EA=3:1) to obtain the target compound A12 (585 mg, 60%).

(1S,3R)-3-acetylamino-N-(5-chloro-4-(4,4-dimethyl-1-oxo-1,2,3,4-tetrahydro isoquinolin-6-yl)pyridin-2-yl)cyclohexyl-1-formamide (96): Compound A12 (100 mg, 0.19 mmol) was dissolved in dichloromethane (2 mL), and added with trifluoroacetic acid (2 mL) dropwisely, and stirred at room temperature for half an hour. After concentrate, the resultant was neutralized with saturated sodium bicarbonate to pH=10, and extracted with dichloromethane, dried over anhydrous sodium sulfate, filtered, and concentrated to obtain light yellow oil, which was directly used in the next step (60 mg).

The product obtained in the previous step was dissolved in dichloromethane, added with triethylamine (21 mg, 0.21 mmol), and then added with acetyl chloride (16 mg, 0.21 mmol) dripwisely under ice bath. The reaction was stopped after TLC showing that the reaction is completed. The resultant was concentrated for column chromatography (eluent system: DCM/MeOH=30:1) to obtain target compound 96 (white solid, 30 mg, 46%). MS: (M+1) 469.20. $^1$H NMR (500 MHz, DMSO-d6) δ 10.74 (s, 1H), 8.49 (s, 1H), 8.18 (s, 1H), 8.08 (d, J=3.1 Hz, 1H), 7.98 (d, J=7.9 Hz, 1H), 7.78 (d, J=7.9 Hz, 1H), 7.50 (d, J=1.7 Hz, 1H), 7.44 (dd, J=7.9, 1.7 Hz, 1H), 3.60-3.51 (m, 1H), 3.23 (d, J=3.0 Hz, 2H), 2.64-2.60 (m, 1H), 1.88 (d, J=12.4 Hz, 1H), 1.77 (s, 6H), 1.31-1.24 (m, 9H), 1.07 (q, J=11.3, 10.8 Hz, 1H).

The following Examples 97, 98, 102 and 107 were synthesized in a similar way as Example 96 unless otherwise specified.

Example 97: (1S,3R)-3-acetylamino-N-(5-chloro-4-(4,4-dimethyl-1-oxo-1,2,3,4-tetrahydroisoquinolin-6-yl)pyrimidin-2-yl)cyclohexyl-1-formamide 97

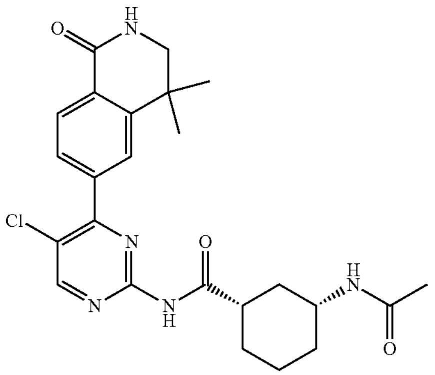 [SMILES: CC(=O)N[C@@H]1CCC[C@H](C(=O)Nc2ncc(Cl)c(-c3ccc4c(c3)C(C)(C)CNC4=O)n2)C1]

MS(ESI) m/z(M+1)+: 470.20.

Example 98: (1S,3R)-3-acetylamino-N-(4-(4,4-dimethyl-1-oxo-1,2,3,4-tetrahydro isoquinolin-6-yl)-5-methylpyrimidin-2-yl)cyclohexyl-1-formamide 98

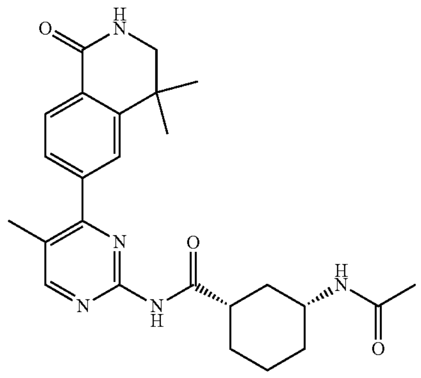 [SMILES: CC(=O)N[C@@H]1CCC[C@H](C(=O)Nc2ncc(C)c(-c3ccc4c(c3)C(C)(C)CNC4=O)n2)C1]

MS(ESI) m/z(M+1)+: 450.25.

Example 99: 6-(5-chloro-2-((4-((methylsulfonyl)methyl)phenyl)amino)pyrimidin-4-yl)-4,4-dimethyl-3,4-dihydroisoquinolin-1(2H)-one 99

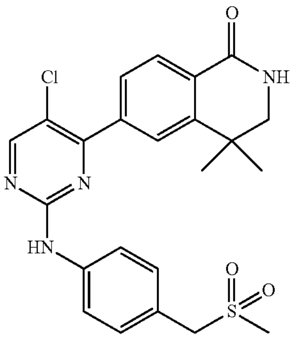 [SMILES: CC1(C)CNC(=O)c2ccc(-c3nc(Nc4ccc(CS(C)(=O)=O)cc4)ncc3Cl)cc21]

MS(ESI) m/z(M+1)+: 471.12.

Example 100: 6-(5-fluoro-2-((4-((((((methylsulfonyl)methyl)phenyl)amino) pyrimidin-4-yl)-4,4-dimethyl-3,4-dihydroisoquinolin-1(2H)-one 100

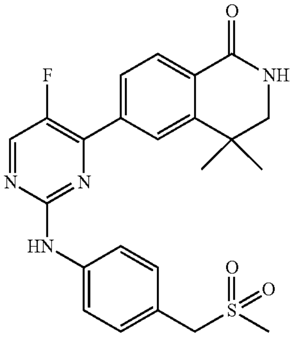 [SMILES: CC1(C)CNC(=O)c2ccc(-c3nc(Nc4ccc(CS(C)(=O)=O)cc4)ncc3F)cc21]

MS(ESI) m/z(M+1)+: 455.15.

Example 101: 5-(2-((2,4-difluoro-5-((methylsulfonyl)methyl)phenyl)amino) pyrimidin-4-yl)-3,3-dimethylisoindole-1-one 101

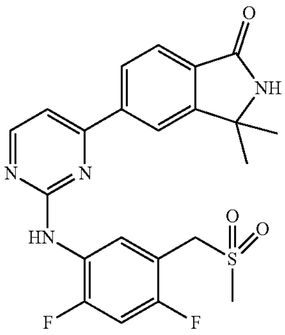 [SMILES: CC1(C)NC(=O)c2ccc(-c3ccnc(Nc4cc(CS(C)(=O)=O)c(F)cc4F)n3)cc21]

MS(ESI) m/z(M+1)+: 459.13.

Example 102: (1S,3R)-3-acetylamino-N-(5-chloro-4-(3,3-dimethyl-1-oxoindolin-5-yl)pyridin-2-yl)cyclohexane-1-formamide 102

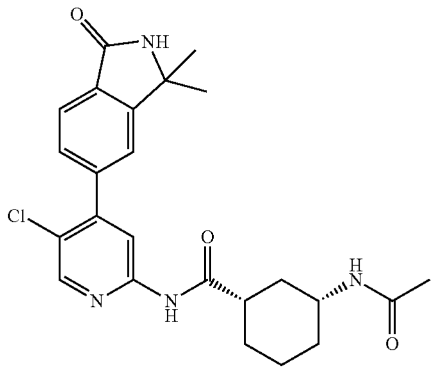 [SMILES: CC(=O)N[C@@H]1CCC[C@H](C(=O)Nc2cc(-c3ccc4c(c3)C(C)(C)NC4=O)c(Cl)cn2)C1]

MS(ESI) m/z(M+1)+: 455.18.

Example 103: (S)-4,4-dimethyl-6-(2-((1-(methanesulfonyl)piperidin-3-yl)amino) pyrimidin-4-yl)-3,4-dihydroisoquinolin-1(2H)-one 103

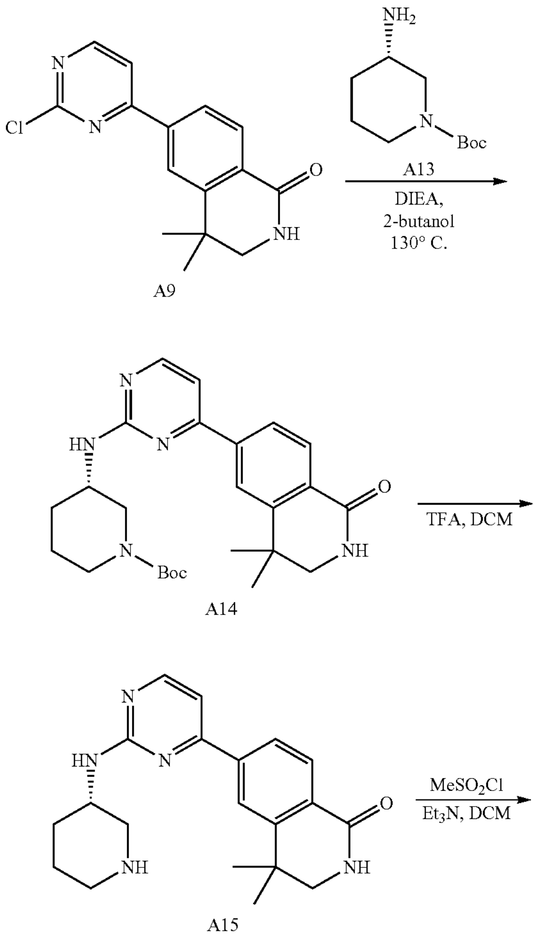

-continued

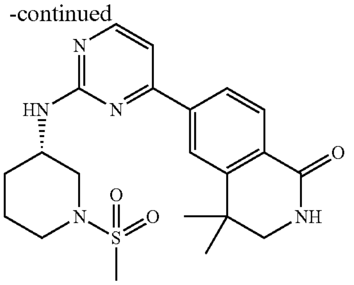

103

(S)-3-((4-(4,4-dimethyl-1-oxo-1,2,3,4-tetrahydroisoquinolin-6-yl)pyrimidin-2-yl) amino)piperidine-1-carboxylic acid tert-butyl ester (A14): A9 (100 mg, 0.35 mmol), A13 (105 mg, 0.52 mmol) and DIEA (90 mg, 0.7 mmol) were dissolved in sec-butanol (2 mL), and the mixture was reacted at 130° C. overnight. After the completion of the reaction as shown by LCMS, the reaction system was loaded on crude silica gel, and A14 (70 mg, 44%) was separated by column chromatography.

(S)-4,4-dimethyl-6-(2-(piperidin-3-ylamino)pyrimidin-4-yl)-3,4-dihydro isoquinolin-1(2H)-one (A15): A14 (70 mg) was dissolved in DCM (3 mL), added with TFA (1 mL), and stirred at room temperature. After the completion of the reaction as shown by LCMS, the resultant was neutralized with saturated sodium bicarbonate to alkaline, and then was extracted with ethyl acetate. The organic phase was dried, concentrated, and the residue was separated by column chromatography to obtain A15 (38 mg, 73%).

(S)-4,4-dimethyl-6-(2-((1-(methanesulfonyl)piperidin-3-yl)amino)pyrimidin-4-yl)-3,4-dihydroisoquinolin-1(2H)-one (103): A15 (38 mg, 0.11 mmol) was dissolved in DCM (2 mL), and was added with methanesulfonyl chloride (18 mg, 0.16 mmol) under ice bath. After the completion of the reaction as shown by LCMS, the resultant was concentrated, and the residue was separated by column chromatography to provide 103 (22 mg, 48%). $^1$H NMR (500 MHz, DMSO-d6) δ 8.43 (d, J=5.1 Hz, 1H), 8.11-7.94 (m, 4H), 7.32 (d, J=7.3 Hz, 1H), 7.27 (d, J=5.2 Hz, 1H), 3.99-3.94 (m, 1H), 3.47 (s, 1H), 3.21-3.20 (m, 2H), 2.87 (s, 3H), 2.75 (td, J=11.3, 2.8 Hz, 1H), 2.56 (t, J=10.3 Hz, 1H), 1.97-1.85 (m, 2H), 1.62-1.51 (m, 2H), 1.34 (d, J=6.0 Hz, 6H).

The following Examples 104-106 were synthesized in a similar way as Example 103 unless otherwise specified.

Example 104: (R)-4,4-dimethyl-6-(2-(((1-(methylsulfonyl)piperidin-3-yl)amino) pyrimidin-4-yl)-3,4-dihydroisoquinolin-1(2H)-one 104

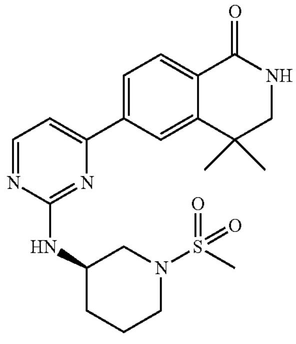 [SMILES: CC1(C)CNC(=O)c2ccc(-c3ccnc(N[C@@H]4CCCN(S(C)(=O)=O)C4)n3)cc21]

MS(ESI) m/z(M+1)+: 430.19.

Example 105: 4,4-dimethyl-6-(2-((1-(methylsulfonyl)piperidin-4-yl)amino) pyrimidin-4-yl)-3,4-dihydroisoquinolin-1(2H)-one 105

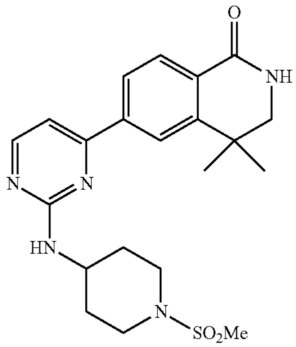 [SMILES: CC1(C)CNC(=O)c2ccc(-c3ccnc(NC4CCN(S(C)(=O)=O)CC4)n3)cc21]

MS(ESI) m/z(M+1)+: 430.19.

Example 106: 2-(1R,4R)-4-((4-(4,4-dimethyl-1-oxo-1,2,3,4-tetrahydroisoquinolin-6-yl)pyrimidin-2-yl) amino)cyclohexyl)acetic acid 106

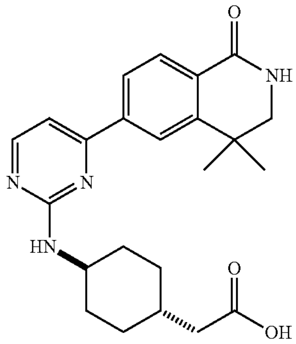

MS(ESI) m/z(M+1)+: 409.22.

Example 107: (R)—N-(5-chloro-4-(4,4-dimethyl-1-oxo-1,2,3,4-tetrahydro isoquinolin-6-yl)pyridin-2-yl) piperidine-3-formamide 107

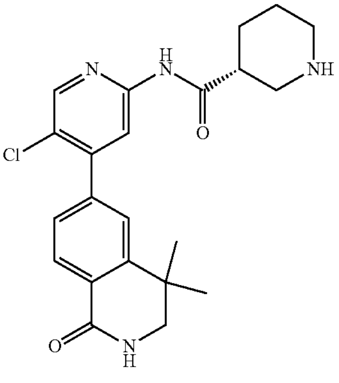 [SMILES: CC1(C)CNC(=O)c2ccc(-c3cc(NC(=O)[C@@H]4CCCNC4)ncc3Cl)cc21]

MS(ESI) m/z(M+1)+: 413.17.

Example 108: Influence of CDK9 Inhibitor on the Growth of Cancer Cells

By testing the influence of CDK9 inhibitor on the growth of cancer cells, we evaluated the selectivity of the compounds for inhibiting the proliferation of cancer cells.

In this example, the following were selected: acute myeloid leukemia cell lines OCI-AML-3, MV4-11, MOLM13, MOLM14, histiocytic lymphoma U-937, human chronic myeloid leukemia cell K562, human colorectal cancer cell HCT116, DLD1, human ovarian granulosa tumor cell COV434, human liver cancer cell line HepG2, lymphoma cell WSU-DLCL2, cervical cancer cell HeLa, gastrointestinal stromal tumor GIST-T1 (the above cells were all purchased from Nanjing Cobioer), MOLM13 drug resistant strain—MOLM13 BR1 obtained by long-term treatment with CDK9 inhibitor BAY1251152 (purchased from MCE, China), and HepG2 drug resistant strain—HepG2 KI C20-1 obtained by knockin through CRISPR Cas9 technology, with the following construction method: HepG2 cells were transfected with guide RNA-PX459 plasmid, and then HepG2 CDK9 KI cells were obtained through purinomycin screening and BAY1251152 screening, which then provided HepG2 KI C20-1 monoclone cells after monoclone screening; CDK9 resistant mutations were detected by sequencing.

In the example, different concentrations (0.000508 μM, 0.00152 μM, 0.00457 μM, 0.0137 μM, 0.0411 μM, 0.123 μM, 0.370 μM, 1.11 μM, 3.33 μM, 10 μM) of compounds of the invention and the control compounds Dinaciclib, JSH-009 and BAY1251152 (all purchased from MCE, China) were added to the above cells, respectively, and incubated for 72 hours, and then detected the number of living cells by quantitative determination of ATP in living cells using Cell Titer-Glo® (Promega, USA) chemiluminescence cell viability test kit, which was used as the basis for calculating $GI_{50}$. The results are shown in Table 1-3.

It is found in the test that the compounds of the invention have significant inhibitory effects on different cancer cell lines. As shown in Table 1 and the continuous table, the inhibitory effects thereof are comparative to that of the control compound pan-CDK inhibitor, Dinaciclib, and the selective CDK9 inhibitor, JSH-009; the anti-proliferative activities of most compounds on cells are comparative to or even better than that of the selective CDK9 inhibitor, BAY1251152. In addition, Table 2 shows significant anti-proliferative effects against the drug resistant strain, which was obtained by treating the acute myeloid leukemia cell MOLM13 with BAY1251152. Therefore, the compounds of the invention show the inhibition effects that overcome drug resistance. As shown in Table 3, the test results on the drug resistant strain of liver cancer cell HepG2 show that the compounds of the invention can overcome the drug resistance, while BAY1251152 has obvious drug resistance.

TABLE 1

| $GI_{50}$/μM | U937 | AML3 | WSU-DLCL2 | HeLa | GIST-T1 |
|---|---|---|---|---|---|
| Dinaciclib | 0.005 | 0.004 | 0.013 | 0.0165 | 0.015 |
| JSH-009 | | | 0.016 | 0.018 | 0.034 |
| Compound 11 | | 0.02 | 0.037 | 0.023 | 0.039 |
| Compound 20 | | 0.006 | 0.007 | 0.004 | 0.011 |
| Compound 21 | | 0.013 | 0.014 | 0.012 | 0.014 |
| Compound 26 | | 0.004 | 0.005 | 0.007 | 0.035 |
| Compound 27 | | 0.006 | 0.008 | 0.013 | 0.04 |
| Compound 28 | 0.002 | 0.002 | | | |
| Compound 29 | 0.186 | 0.153 | | | |
| Compound 31 | 0.016 | 0.023 | | | |
| Compound 32 | 0.007 | 0.012 | | | |
| Compound 33 | 0.063 | 0.048 | | | |
| Compound 34 | 0.007 | 0.008 | | | |
| Compound 35 | 0.023 | 0.033 | | | |
| Compound 39 | 0.0077 | 0.022 | | | |
| Compound 40 | 0.0046 | 0.005 | | | |
| Compound 41 | 0.013 | 0.023 | | | |
| Compound 42 | <0.0015 | 0.003 | | | |

| $GI_{50}$/μM | HepG2 | HCT116 | COV434 | MV4-11 | MOLM 13 | MOLM 14 | K562 | DLD1 |
|---|---|---|---|---|---|---|---|---|
| Dinaciclib | | 0.015 | 0.008 | 0.022 | 0.011 | 0.018 | 0.053 | 0.03 |
| JSH-009 | | 0.023 | 0.03 | 0.006 | 0.004 | 0.004 | 0.009 | 0.106 |
| BAY1251152 | | | | 0.027 | | 0.04 | | |
| Compound 11 | 0.05 | 0.025 | 0.03 | 0.035 | | | 0.081 | |
| Compound 12 | | | 0.078 | 0.086 | | | | |
| Compound 13 | 0.005 | 0.008 | | 0.003 | | | 0.022 | 0.028 |
| Compound 14 | 0.023 | 0.012 | | 0.017 | | | 0.026 | 0.063 |
| Compound 15 | | | | | 0.012 | 0.015 | | |
| Compound 16 | | | | | 0.005 | 0.005 | | |
| Compound 20 | | | | | 0.019 | 0.024 | 0.1 | |

TABLE 1-continued

| | | | | | | | | |
|---|---|---|---|---|---|---|---|---|
| Compound 21 | | | | | 0.06 | 0.055 | 0.38 | |
| Compound 22 | | | | | 0.028 | 0.041 | | |
| Compound 26 | 0.057 | 0.005 | | 0.004 | | | 0.018 | 0.021 |
| Compound 27 | 0.095 | 0.008 | | 0.005 | | | 0.043 | 0.013 |
| Compound 96 | | | | 0.009 | 0.008 | 0.017 | 0.072 | |
| Compound 28 | | | | 0.002 | 0.001 | 0.002 | 0.01 | |
| Compound 29 | | | | 0.057 | 0.035 | 0.059 | 0.942 | |
| Compound 31 | | | 0.013 | 0.009 | 0.019 | | 0.086 | |
| Compound 32 | | | 0.011 | 0.004 | 0.006 | | 0.033 | |
| Compound 33 | | | 0.008 | 0.006 | 0.01 | | 0.077 | |
| Compound 34 | | | 0.009 | 0.004 | 0.011 | | 0.024 | |
| Compound 35 | | | <0.001 | <0.001 | <0.001 | | 0.025 | |
| Compound 36 | | | | 0.003 | <0.001 | 0.002 | 0.009 | |
| Compound 37 | | | | <0.001 | <0.001 | <0.001 | 0.031 | |
| Compound 38 | | | | 0.013 | 0.005 | 0.016 | 0.095 | |
| Compound 39 | | | | 0.01 | 0.0098 | 0.037 | 0.037 | |
| Compound 40 | | | | 0.0017 | 0.003 | 0.0058 | 0.025 | |
| Compound 41 | | | | 0.0066 | 0.011 | 0.025 | 0.084 | |
| Compound 42 | | | | 0.0025 | 0.0022 | 0.003 | 0.012 | |
| Compound 44 | | | | | 0.011 | 0.013 | | |
| Compound 45 | | | | | 0.03 | 0.096 | | |
| Compound 48 | | | | | 0.0055 | 0.0052 | | |
| Compound 48 | | | | | | 0.0051 | | |
| Compound 49 | | | | | 0.056 | 0.078 | | |
| Compound 50 | | | | | | 0.0046 | | |
| Compound 51 | | | | | | 0.015 | | |
| Compound 56 | | | | | 0.004 | 0.0048 | | |
| Compound 63 | | | | | 0.019 | 0.044 | | |
| Compound 72 | | | | | <0.001 | 0.0055 | | |
| Compound 73 | | | | | <0.001 | <0.001 | 0.026 | |
| Compound 75 | | | | | 0.033 | 0.11 | | |
| Compound 80 | | | | | 0.0033 | 0.0072 | 0.015 | |
| Compound 82 | | | | | <0.001 | 0.0008 | 0.026 | |
| Compound 99 | | | | | 0.021 | 0.021 | | |
| Compound 100 | | | | | 0.0045 | 0.01 | | |
| Compound 104 | | | | 0.034 | | 0.01 | | |
| Compound 105 | | | | 0.082 | | 0.043 | | |

TABLE 2

| $GI_{50}$ (nM) | MOLM13 | MOLM13 BR1 |
|---|---|---|
| Compound 11 | 27.26 | 40.48 |
| Compound 13 | 6.099 | 10.03 |
| Compound 14 | 7.085 | 8.259 |
| Compound 26 | 3.483 | 6.143 |
| Compound 27 | 6.659 | 23.09 |
| Compound 82 | 0.8445 | 1.705 |
| Compound 35 | | 1.689 |
| Compound 37 | | 3.052 |
| Compound 40 | | 4.387 |
| Compound 42 | | 8.449 |
| Compound 73 | 1.64 | 0.345 |
| Compound 80 | 11.59 | 12.3 |
| Compound 96 | | 5.6 |
| BAY1251152 | 37.95 | 1188 |

TABLE 3

| GI50 (nM) | HepG2 | HepG2 CDK9 KI C20-1 |
|---|---|---|
| Compound 35 | 87.42 | 138.5 |
| Compound 37 | 27.77 | 74.8 |
| BAY1251152 | 36.07 | >1000 |

Example 109: Detection of Binding Activity of Compound and CDK9

The plasmid of split luciferase system was constructed by molecular cloning technology. The N-terminal domain (NLuc) and C-terminal domain (CLuc) of luciferase were respectively cloned and inserted into the vector PCDNA3 to construct NLuc-PCDNA3 and CLuc-PCDNA3 vectors, and the polyclonal sites were reserved at both ends of the sequence. Then CDC37 and CDK9 were cloned into the corresponding vectors to construct C37-CL and CDK9-NL vectors. C37-CL plasmid sequence is shown in SEQ ID NO. 1. CDK9-NL plasmid sequence is shown in SEQ ID NO. 2.

HEK-293T (purchased from ATCC, U.S.) was inoculated in a 10 cm cell culture dish, waiting for the cell density to reach 70% before use. 2 μg C37-CL (SEQ ID NO. 1) and 2 μg CDK9-NL plasmid (SEQ ID NO. 2) were added to 1 mL of Opti-MEM (Item No. 2120763, purchased from Gibco, U.S.), and then 6 μL of transfection reagent (Item No. 20200918, purchased from HanBio, China), and then mixed for use. The mixed transfection complex was added to the 10 cm cell culture dish and cultured at 37° C. and 5% $CO_2$ for 24 hours. After 24 hours, the HEK-293T cells were digested with trypsin. After counting, the transfected cells were placed in a 96-well white Corning cell culture plate (purchased from Corning, U.S.) with 100 μL, 5000 cells/well. After 12 hours, the medium was removed from the 96-well plate and 100 μL culture medium containing corresponding concentration of the testing compound was added, which was cultured continuously for 12 hours. After 12 hours, 20 μL Luciferase-Glo (purchased from Promega, U.S.) testing reagent was added to each well. After mixing, the fluorescence value was detected using a microplate reader. The relative activity $IC_{50}$ value was calculated according to the following formula: relative activity=(fluorescence value of testing drug−background value)/(fluorescence value of DMSO group−background value)×100%. The test results show that the compounds of the invention have strong binding activities with CDK9.

TABLE 4

| | Binding activity with CDK9 in HEK-293T cells ($IC_{50}$: μM) |
|---|---|
| Compound 11 | 0.06 |
| Compound 12 | 0.098 |
| Compound 20 | 0.036 |
| Compound 21 | 0.044 |
| Compound 26 | 0.016 |
| Compound 27 | 0.019 |
| Compound 28 | 0.015 |
| Compound 31 | 0.129 |
| Compound 32 | 0.049 |
| Compound 34 | 0.05 |
| Compound 35 | 0.3 |
| Compound 36 | 0.19 |
| Compound 37 | 0.049 |
| Compound 39 | 0.087 |
| Compound 40 | 0.067 |
| Compound 41 | 0.114 |
| Compound 42 | 0.09 |

Example 110: Enzyme Activity Assay of CDK9 Protein Inhibition In Vitro

The DMSO diluted compounds and the control compounds Dinaciclib, JSH-009, BAY-1211152, AZD4573 (all purchased from MCE, China) were mixed with the detected CDK9/CyclinT1 protein (Invitrogen, U.S.), CDK9-L156F mut/CyclinT1 mutant protein (this mutation is consistent with the mutation in HepG2 KI C20-1, which was constructed as described in Example 108), and incubated at room temperature for 30 minutes; Kinase Peptide Substrate Mixture (Invitrogen, U.S.) and 4×ATP were added for mixing, and the mixing system was transferred to a 384-well white opaque plate for reaction at room temperature for 1 hour; 5 μL Development Solution (Invitrogen, U.S.) was added and reacted at room temperature for 1 hour, and finally Stop Agent (Invitrogen, U.S.) was added to terminate the reaction; the fluorescence value was read using MD SpectraMax I3X microplate (Molecular Devices, U.S.). The $IC_{50}$ values of the compounds of the invention on the tested CDK9/CyclinT1 protein and CDK9 mutant protein CDK9-L156F mut/CyclinT1 were calculated by plotting using Prism 5.0 (GraphPad Software, San Diego, CA) based on the read fluorescence value, which were shown in Table 5 and Table 6 below. The results show that the compounds of the invention have significant inhibitory effects on CDK9 and its mutation: for the wild type CDK9/CyclinT1 protein, they show superior or comparative effects over the control compounds, while for the CDK9 mutant protein CDK9-L156F mut/CyclinT1, their inhibitory effects are significantly superior to that of the control compound, BAY1251152.

TABLE 5

| Compound No. | CDK9/CyclinT1 Protein activity ($IC_{50}$: nM) |
|---|---|
| Dinaciclib | 30 |
| HY-009 | 29 |
| BAY-1211152 | 12.3 |
| AZD4573 | 13 |
| Compound 1 | 38 |
| Compound 11 | 11.1 |
| Compound 20 | 1.04 |
| Compound 22 | 13 |
| Compound 26 | 3.1 |

TABLE 5-continued

| Compound No. | CDK9/CyclinT1 Protein activity ($IC_{50}$: nM) |
|---|---|
| Compound 27 | 0.89 |
| Compound 28 | 1 |
| Compound 29 | 27 |
| Compound 30 | 12 |
| Compound 34 | 6.1 |
| Compound 36 | 6.1 |
| Compound 37 | 2.8 |
| Compound 39 | 2.7 |
| Compound 40 | 6.6 |
| Compound 41 | 2.5 |
| Compound 42 | 6.2 |
| Compound 44 | 7 |
| Compound 48 | 5.9 |
| Compound 49 | 11 |
| Compound 50 | 1.59 |
| Compound 56 | 6.2 |
| Compound 72 | 15 |
| Compound 82 | 2.6 |
| Compound 96 | 0.52 |
| Compound 99 | 9.3 |
| Compound 100 | 8.9 |
| Compound 104 | 0.9 |
| Compound 105 | 15.02 |
| Compound 106 | 10.37 |

TABLE 6

| | CDK9 mutant protein CDK9-L156F mut/CyclinT1 ($IC_{50}$: nM) |
|---|---|
| Compound 11 | 178.2 |
| Compound 13 | 126.8 |
| Compound 14 | 98.59 |
| Compound 26 | 22.64 |
| Compound 27 | 124.6 |
| Compound 82 | 105.5 |
| BAY1251152 | 1252 |

INDUSTRIAL APPLICABILITY

The invention provides a CDK9 kinase inhibitor, which can be used to inhibit the activities of CDK9 and/or its mutated kinase and to treat or prevent diseases related to or mediated by the activities of CDK9 and/or its mutations. Therefore, it can be made into corresponding drugs suitable for industrial application.

Although the invention is described in detail herein, it is not limited to this. Those skilled in the art can make modification according to the principle of the invention. Therefore, all modifications made according to the principle of the invention should be understood to be within the protection scope of the invention.

The invention claimed is:

1. A kinase inhibitor, comprising a compound of formula (I) or a pharmaceutically acceptable salt, solvate, ester, acid, metabolite or prodrug thereof, Formula (I)

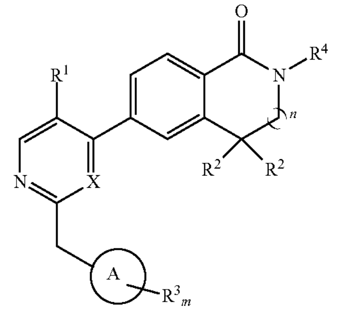

wherein, A is selected from the group consisting of cyclohexyl, phenyl, pyridinyl and piperidyl;

X is CH or N;

Z is —NH— or —NH—C(═O)—;

n is 0 or 1;

$R^1$ is selected from the group consisting of hydrogen, halogen, cyano, (C1-C6)alkyl, and (C1-C6)haloalkyl;

$R^2$ are selected from the group consisting of hydrogen and (C1-C6)alkyl, or two $R^2$ together form a (C3-C6) cycloalkyl;

m is selected from the integer of 1-3, and each $R^3$ is independently selected from the group consisting of hydrogen, —NH—(C1-C3)alkyl-(C1-C3)alkoxy, halogen, (C1-C6)alkyl, (C1-C6)alkoxy, (C1-C6)haloalkyl, (C1-C6)alkylacylamino, (C1-C6)alkylsulfonyl, (C1-C6)alkylsulfonamido, aminosulfonyl, (C1-C6)alkylaminosulfonyl, heterocyclyl sulfonyl with heteroatom(s) being optionally substituted by (C1-C6)alkyl, carboxyl(C1-C3)alkyl, aminosulfonyl(C1-C3)alkyl, (C1-C3)alkylsulfonyl(C1-C3)alkyl, (C1-C3)alkylsulfonyl(C3-C6)cycloalkyl, heterocyclyl aminoacyl with heteroatom(s) being optionally substituted by (C1-C6)alkyl, heterocyclyl with heteroatom(s) being optionally substituted by (C1-C6)alkyl, —S(═O)(═NH)(C1-C3)alkyl, and —(C1-C3)alkyl-S(═O)(═NH)(C1-C3)alkyl;

$R^4$ is selected from the group consisting of hydrogen and (C1-C6)alkyl.

2. The kinase inhibitor of claim 1, comprising a compound of formula (Ia) or a pharmaceutically acceptable salt, solvate, ester, acid, metabolite or prodrug thereof, Formula (Ia)

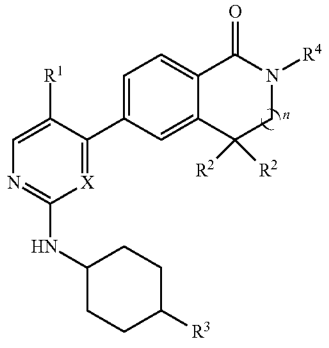

wherein, $R^3$ is —NH—(C1-C3)alkyl-(C1-C3)alkoxy or carboxyl(C1-C3)alkyl.

3. The kinase inhibitor of claim 1, comprising a compound of formula (Ib) or a pharmaceutically acceptable salt, solvate, ester, acid, metabolite or prodrug thereof, Formula (Ib)

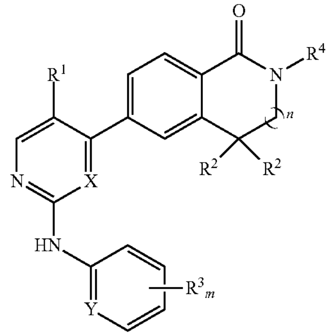

wherein, Y is CH or N;

m is selected from the integer of 1-3, and each $R^3$ is independently selected from the group consisting of halogen, (C1-C6)alkyl, (C1-C6)alkoxy, (C1-C6)haloalkyl, (C1-C6)alkylsulfonyl, (C1-C6)alkylsulfonamido, aminosulfonyl, (C1-C6)alkylaminosulfonyl, heterocyclyl sulfonyl with heteroatom(s) being optionally substituted by (C1-C6)alkyl, aminosulfonyl(C1-C3)alkyl, (C1-C3)alkylsulfonyl(C1-C3)alkyl, (C1-C3)alkylsulfonyl(C3-C6)cycloalkyl, heterocyclyl aminoacyl with heteroatom(s) being optionally substituted by (C1-C6)alkyl, heterocyclyl with heteroatom(s) being optionally substituted by (C1-C6)alkyl, —S(═O)(═NH)(C1-C3)alkyl, and —(C1-C3)alkyl-S(═O)(═NH)(C1-C3)alkyl.

4. The kinase inhibitor of claim 1, comprising a compound of formula (Ic) or a pharmaceutically acceptable salt, solvate, ester, acid, metabolite or prodrug thereof, Formula (Ic)

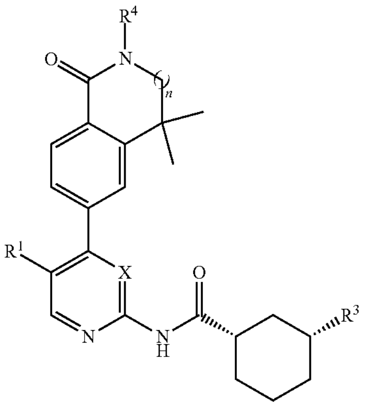

wherein, $R^3$ is (C1-C6)alkylacylamino.

5. The kinase inhibitor of claim 1, comprising a compound of formula (Id) or a pharmaceutically acceptable salt, solvate, ester, acid, metabolite or prodrug thereof, Formula (Id)
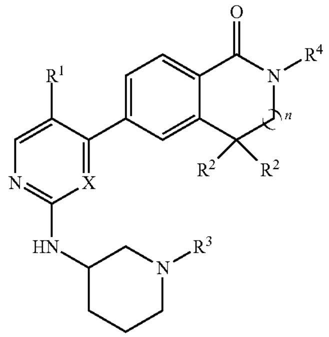
wherein, $R^3$ is (C1-C6)alkylsulfonyl.
6. The kinase inhibitor of claim 1, wherein X is N.
7. The kinase inhibitor of claim 1, comprising the following compound or a pharmaceutically acceptable salt, solvate, ester, acid, metabolite or prodrug thereof:
| Comp. No. | Comp. Structure |
|---|---|
| 1 | 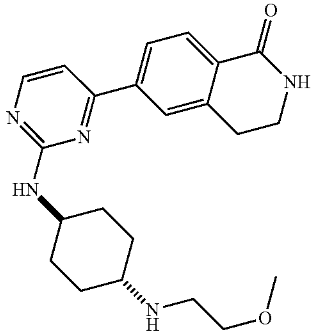 |
| 2 | 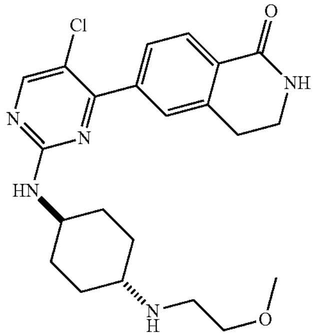 |
| 3 | 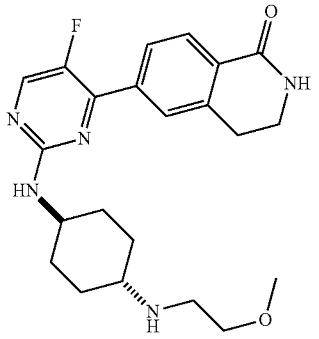 |
-continued
| Comp. No. | Comp. Structure |
|---|---|
| 4 | 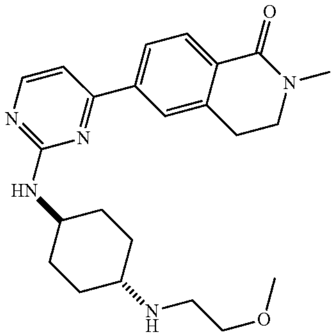 |
| 5 | 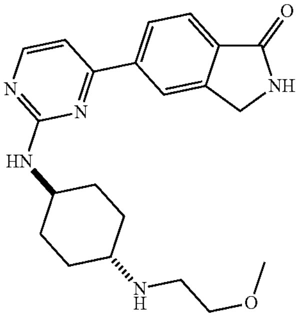 |
| 6 | 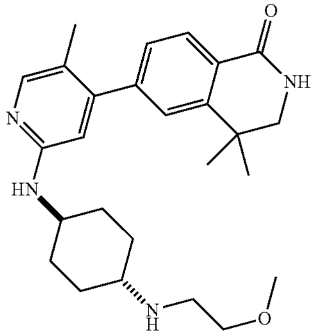 |
| 7 | 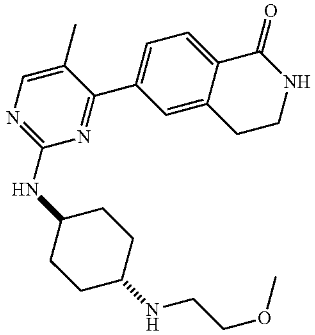 |

-continued
| Comp. No. | Comp. Structure |
|---|---|
| 8 | 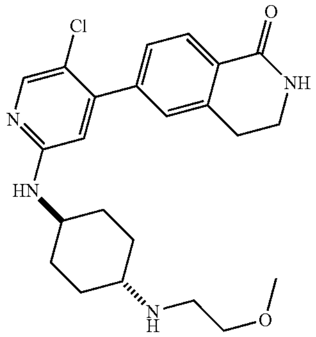 |
| 9 | 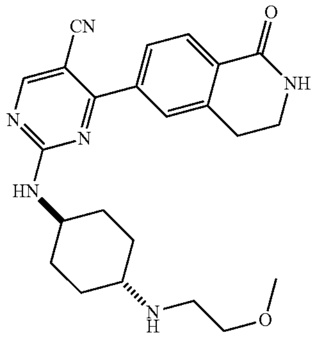 |
| 10 | 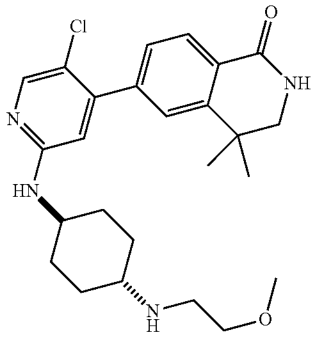 |
| 11 | 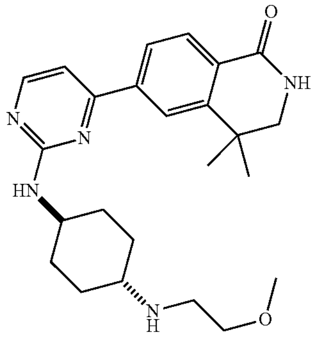 |
-continued
| Comp. No. | Comp. Structure |
|---|---|
| 12 | 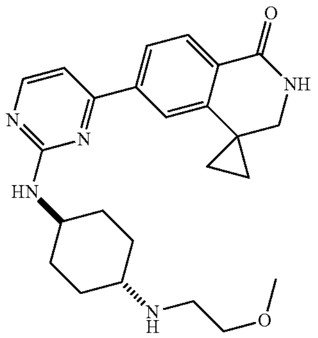 |
| 13 | 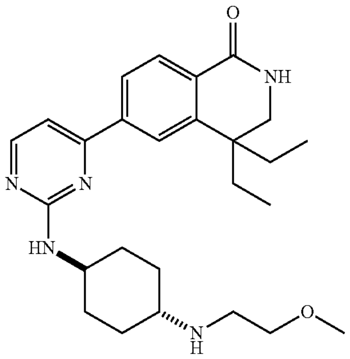 |
| 14 | 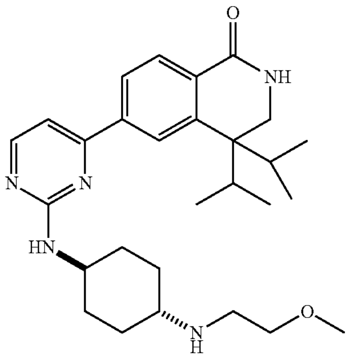 |
| 15 | 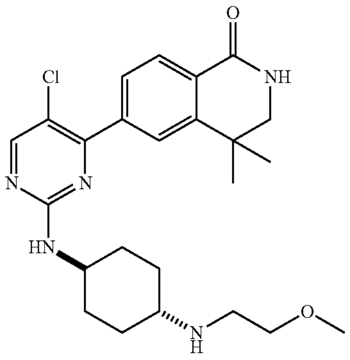 |

-continued
| Comp. No. | Comp. Structure |
|---|---|
| 16 | 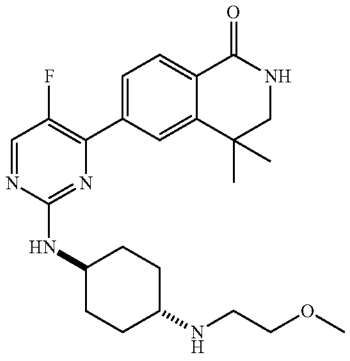 |
| 17 | 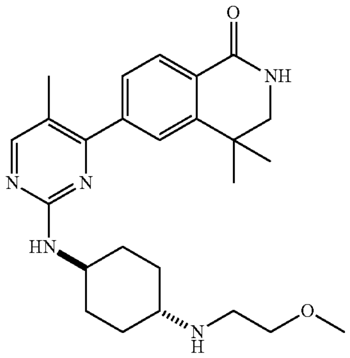 |
| 18 | 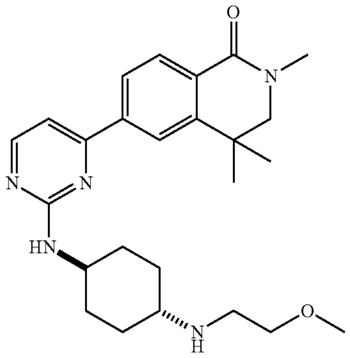 |
| 19 | 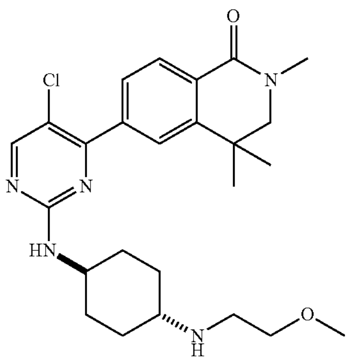 |
-continued
| Comp. No. | Comp. Structure |
|---|---|
| 20 | 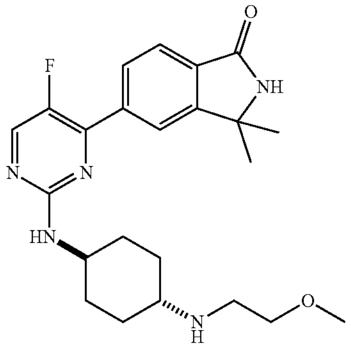 |
| 21 | 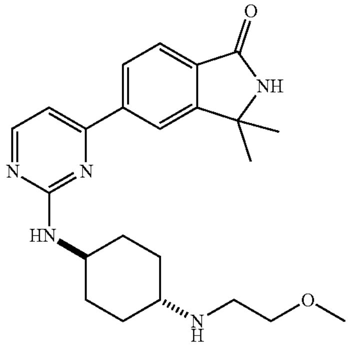 |
| 22 | 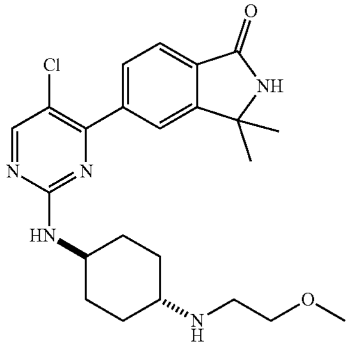 |
| 23 | 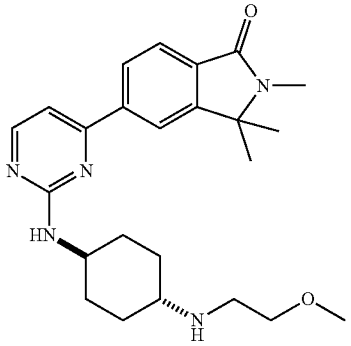 |

-continued
| Comp. No. | Comp. Structure |
|---|---|
| 24 | 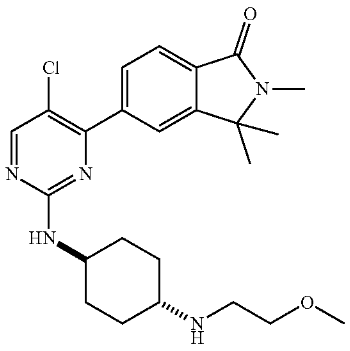 |
| 25 | 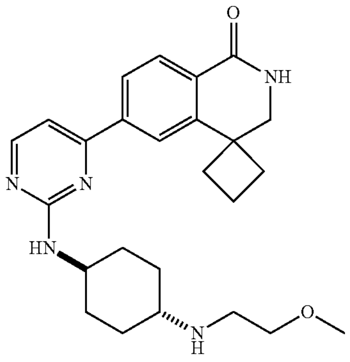 |
| 26 | 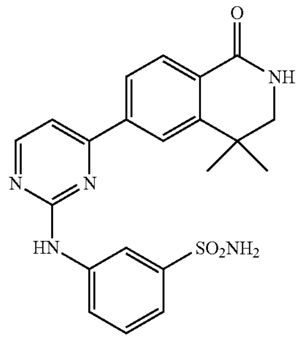 [SMILES: CC1(C)CNC(=O)c2ccc(-c3ccnc(Nc4cccc(S(N)(=O)=O)c4)n3)cc21] |
| 27 | 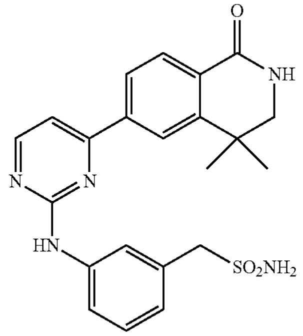 [SMILES: CC1(C)CNC(=O)c2ccc(-c3ccnc(Nc4cccc(CS(N)(=O)=O)c4)n3)cc21] |
-continued
| Comp. No. | Comp. Structure |
|---|---|
| 28 | 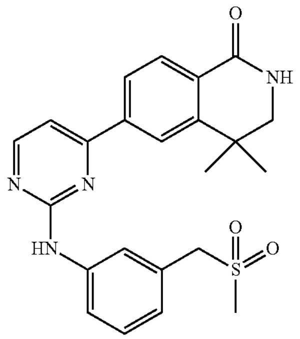 |
| 29 | 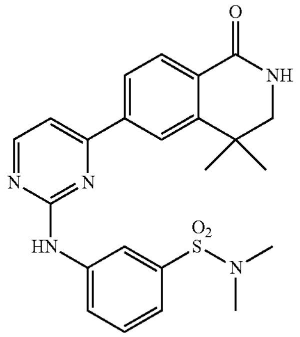 [SMILES: CN(C)S(=O)(=O)c1cccc(Nc2nccc(-c3ccc4c(c3)C(C)(C)CNC4=O)n2)c1] |
| 30 | 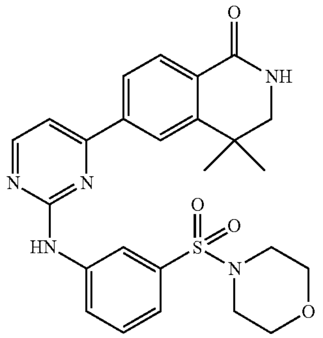 [SMILES: CC1(C)CNC(=O)c2ccc(-c3ccnc(Nc4cccc(S(=O)(=O)N5CCOCC5)c4)n3)cc21] |
| 31 | 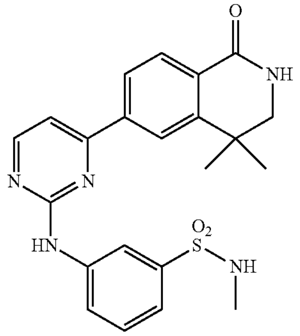 [SMILES: CNS(=O)(=O)c1cccc(Nc2nccc(-c3ccc4c(c3)C(C)(C)CNC4=O)n2)c1] |

-continued
| Comp. No. | Comp. Structure |
|---|---|
| 32 | 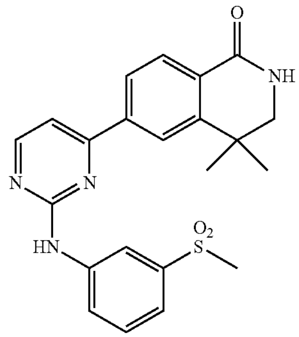 [SMILES: CC1(C)CNC(=O)c2ccc(-c3ccnc(Nc4cccc(S(C)(=O)=O)c4)n3)cc21] |
| 33 | 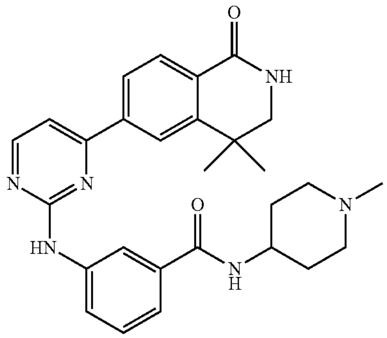 [SMILES: CN1CCC(NC(=O)c2cccc(Nc3nccc(-c4ccc5c(c4)C(C)(C)CNC5=O)n3)c2)CC1] |
| 34 | 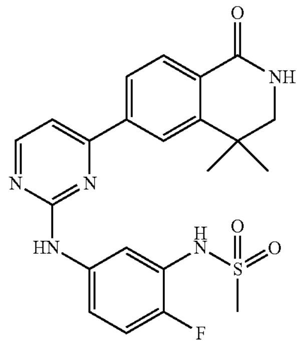 [SMILES: CC1(C)CNC(=O)c2ccc(-c3ccnc(Nc4ccc(F)c(NS(C)(=O)=O)c4)n3)cc21] |
| 35 | 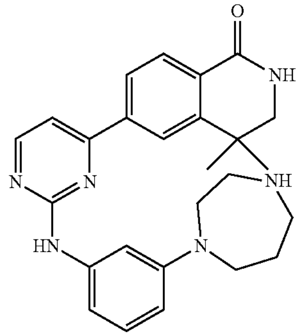 [SMILES: CC1(C)CNC(=O)c2ccc(-c3ccnc(Nc4cccc(N5CCCNCC5)c4)n3)cc21] |
-continued
| Comp. No. | Comp. Structure |
|---|---|
| 36 | 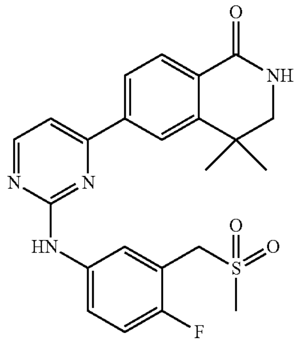 [SMILES: CC1(C)CNC(=O)c2ccc(-c3ccnc(Nc4ccc(F)c(CS(C)(=O)=O)c4)n3)cc21] |
| 37 | 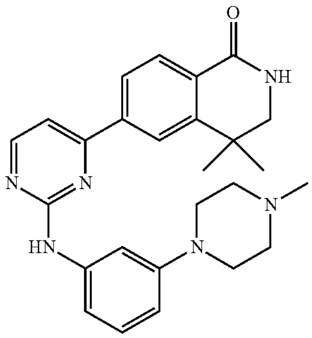 [SMILES: CN1CCN(c2cccc(Nc3nccc(-c4ccc5c(c4)C(C)(C)CNC5=O)n3)c2)CC1] |
| 38 | 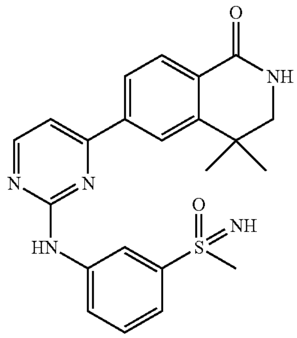 [SMILES: CC1(C)CNC(=O)c2ccc(-c3ccnc(Nc4cccc(S(C)(=N)=O)c4)n3)cc21] |
| 39 | 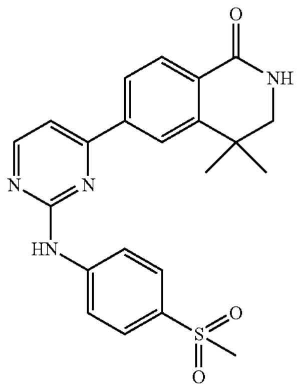 [SMILES: CC1(C)CNC(=O)c2ccc(-c3ccnc(Nc4ccc(S(C)(=O)=O)cc4)n3)cc21] |

-continued
| Comp. No. | Comp. Structure |
|---|---|
| 40 | 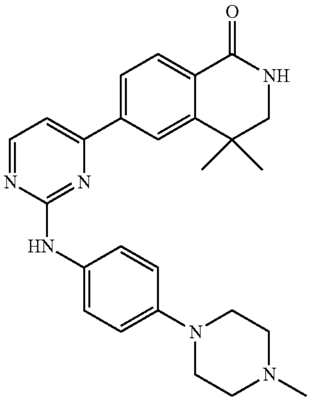 [SMILES: CN1CCN(c2ccc(Nc3nccc(-c4ccc5c(c4)C(C)(C)CNC5=O)n3)cc2)CC1] |
| 41 | 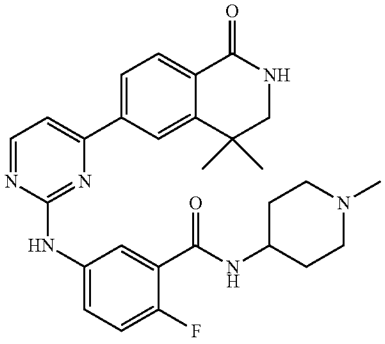 [SMILES: CN1CCC(NC(=O)c2cc(Nc3nccc(-c4ccc5c(c4)C(C)(C)CNC5=O)n3)ccc2F)CC1] |
| 42 | 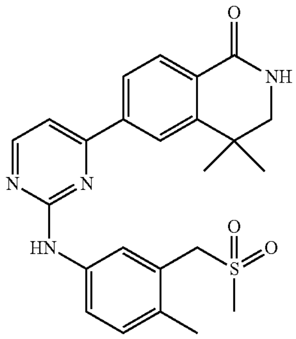 |
| 43 | 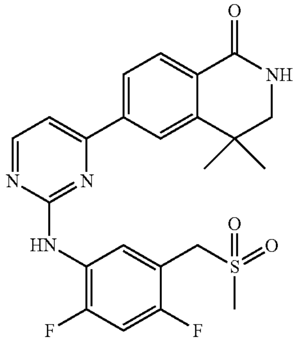 |
-continued
| Comp. No. | Comp. Structure |
|---|---|
| 44 | 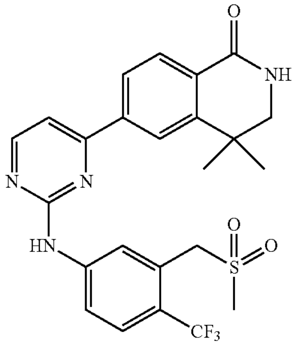 [SMILES: CC1(C)CNC(=O)c2ccc(-c3ccnc(Nc4ccc(C(F)(F)F)c(CS(C)(=O)=O)c4)n3)cc21] |
| 45 | 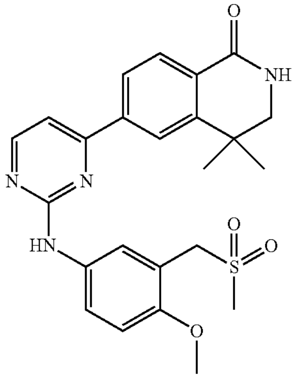 [SMILES: COc1ccc(Nc2nccc(-c3ccc4c(c3)C(C)(C)CNC4=O)n2)cc1CS(C)(=O)=O] |
| 46 | 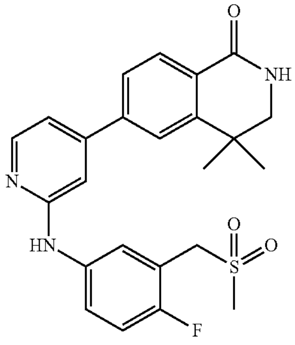 [SMILES: CC1(C)CNC(=O)c2ccc(-c3ccnc(Nc4ccc(F)c(CS(C)(=O)=O)c4)c3)cc21] |
| 47 | 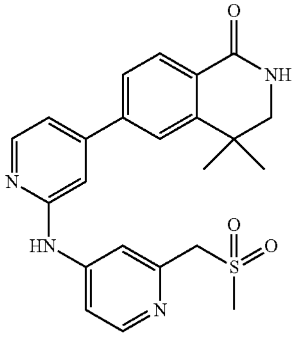 |

-continued
| Comp. No. | Comp. Structure |
| --- | --- |
| 48 | 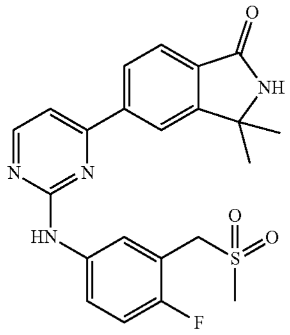 [SMILES: CC1(C)NC(=O)c2ccc(-c3ccnc(Nc4ccc(F)c(CS(C)(=O)=O)c4)n3)cc21] |
| 49 | 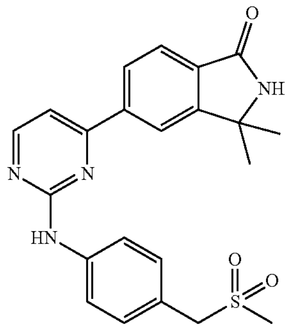 [SMILES: CC1(C)NC(=O)c2ccc(-c3ccnc(Nc4ccc(CS(C)(=O)=O)cc4)n3)cc21] |
| 50 | 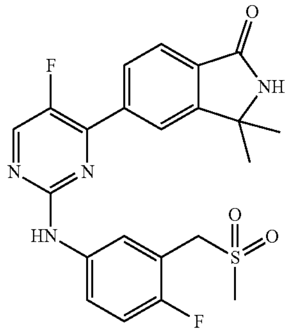 [SMILES: CC1(C)NC(=O)c2ccc(-c3nc(Nc4ccc(F)c(CS(C)(=O)=O)c4)ncc3F)cc21] |
| 51 | 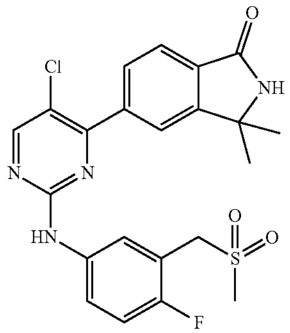 [SMILES: CC1(C)NC(=O)c2ccc(-c3nc(Nc4ccc(F)c(CS(C)(=O)=O)c4)ncc3Cl)cc21] |
-continued
| Comp. No. | Comp. Structure |
| --- | --- |
| 52 | 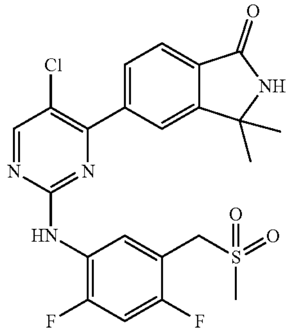 [SMILES: CC1(C)NC(=O)c2ccc(-c3nc(Nc4cc(CS(C)(=O)=O)c(F)cc4F)ncc3Cl)cc21] |
| 53 | 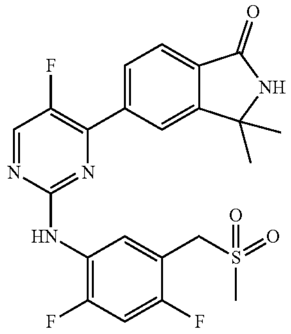 [SMILES: CC1(C)NC(=O)c2ccc(-c3nc(Nc4cc(CS(C)(=O)=O)c(F)cc4F)ncc3F)cc21] |
| 54 | 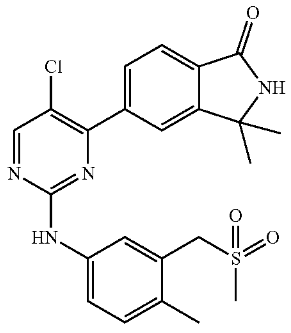 [SMILES: Cc1ccc(Nc2ncc(Cl)c(-c3ccc4c(c3)C(C)(C)NC4=O)n2)cc1CS(C)(=O)=O] |
| 55 | 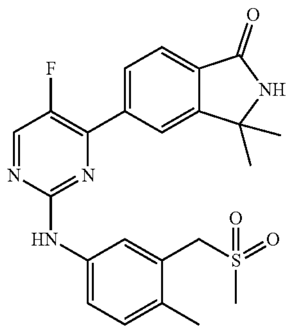 [SMILES: Cc1ccc(Nc2ncc(F)c(-c3ccc4c(c3)C(C)(C)NC4=O)n2)cc1CS(C)(=O)=O] |

-continued
| Comp. No. | Comp. Structure |
|---|---|
| 56 | 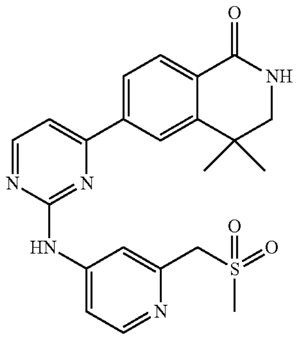 [SMILES: CC1(C)CNC(=O)c2ccc(-c3ccnc(Nc4ccnc(CS(C)(=O)=O)c4)n3)cc21] |
| 57 | 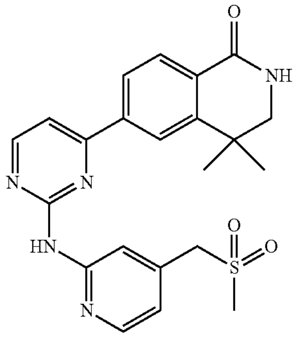 [SMILES: CC1(C)CNC(=O)c2ccc(-c3ccnc(Nc4cc(CS(C)(=O)=O)ccn4)n3)cc21] |
| 58 | 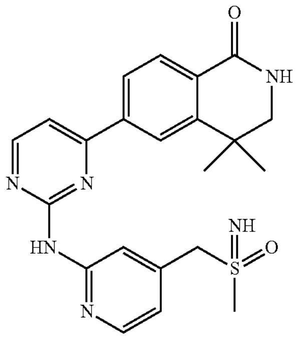 [SMILES: CC1(C)CNC(=O)c2ccc(-c3ccnc(Nc4cc(CS(C)(=N)=O)ccn4)n3)cc21] |
| 59 | 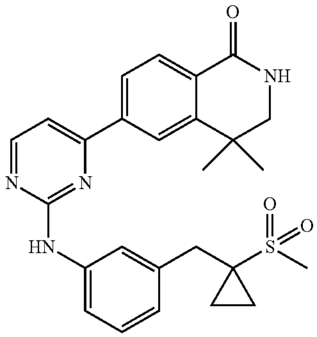 [SMILES: CC1(C)CNC(=O)c2ccc(-c3ccnc(Nc4cccc(CC5(S(C)(=O)=O)CC5)c4)n3)cc21] |
-continued
| Comp. No. | Comp. Structure |
|---|---|
| 60 | 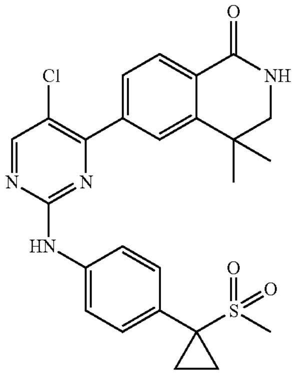 [SMILES: CC1(C)CNC(=O)c2ccc(-c3nc(Nc4ccc(C5(S(C)(=O)=O)CC5)cc4)ncc3Cl)cc21] |
| 61 | 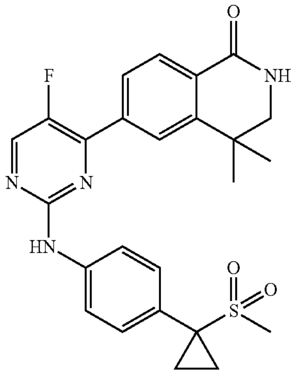 [SMILES: CC1(C)CNC(=O)c2ccc(-c3nc(Nc4ccc(C5(S(C)(=O)=O)CC5)cc4)ncc3F)cc21] |
| 62 | 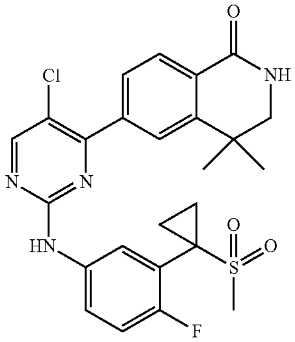 [SMILES: CC1(C)CNC(=O)c2ccc(-c3nc(Nc4ccc(F)c(C5(S(C)(=O)=O)CC5)c4)ncc3Cl)cc21] |
| 63 | 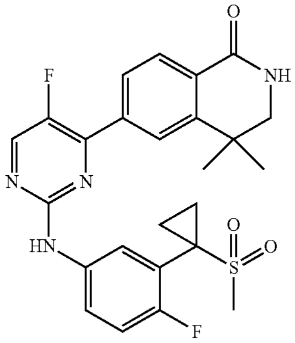 [SMILES: CC1(C)CNC(=O)c2ccc(-c3nc(Nc4ccc(F)c(C5(S(C)(=O)=O)CC5)c4)ncc3F)cc21] |

-continued
| Comp. No. | Comp. Structure |
| --- | --- |
| 64 | 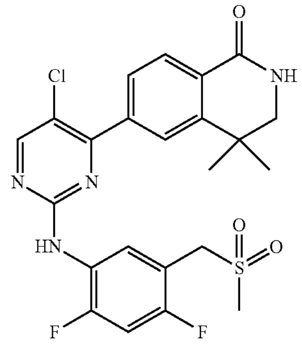 [SMILES: CC1(C)CNC(=O)c2ccc(-c3nc(Nc4cc(CS(C)(=O)=O)c(F)cc4F)ncc3Cl)cc21] |
| 65 | 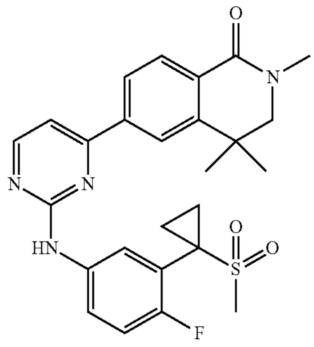 [SMILES: CN1CC(C)(C)c2cc(-c3ccnc(Nc4ccc(F)c(C5(S(C)(=O)=O)CC5)c4)n3)ccc2C1=O] |
| 66 | 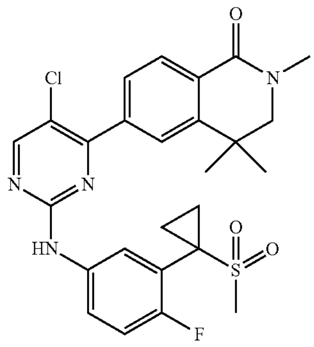 [SMILES: CN1CC(C)(C)c2cc(-c3nc(Nc4ccc(F)c(C5(S(C)(=O)=O)CC5)c4)ncc3Cl)ccc2C1=O] |
| 67 | 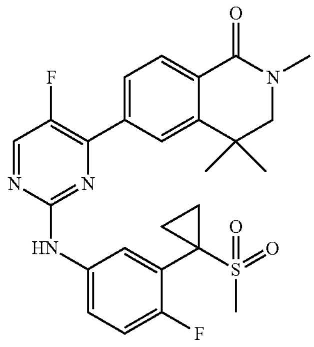 [SMILES: CN1CC(C)(C)c2cc(-c3nc(Nc4ccc(F)c(C5(S(C)(=O)=O)CC5)c4)ncc3F)ccc2C1=O] |
-continued
| Comp. No. | Comp. Structure |
| --- | --- |
| 68 | 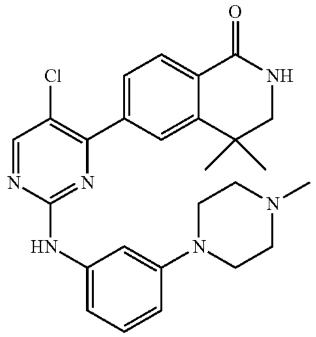 [SMILES: CN1CCN(c2cccc(Nc3ncc(Cl)c(-c4ccc5c(c4)C(C)(C)CNC5=O)n3)c2)CC1] |
| 69 | 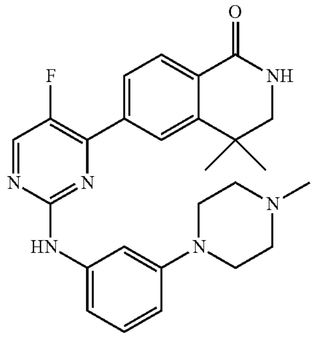 [SMILES: CN1CCN(c2cccc(Nc3ncc(F)c(-c4ccc5c(c4)C(C)(C)CNC5=O)n3)c2)CC1] |
| 70 | 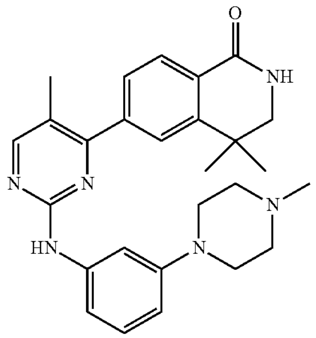 [SMILES: Cc1cnc(Nc2cccc(N3CCN(C)CC3)c2)nc1-c1ccc2c(c1)C(C)(C)CNC2=O] |
| 71 | 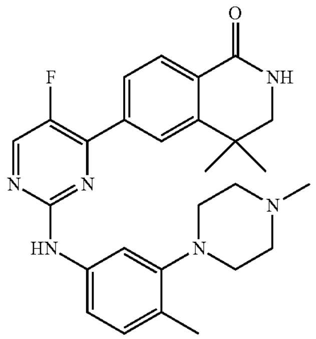 [SMILES: Cc1ccc(Nc2ncc(F)c(-c3ccc4c(c3)C(C)(C)CNC4=O)n2)cc1N1CCN(C)CC1] |

-continued
| Comp. No. | Comp. Structure |
| --- | --- |
| 72 | 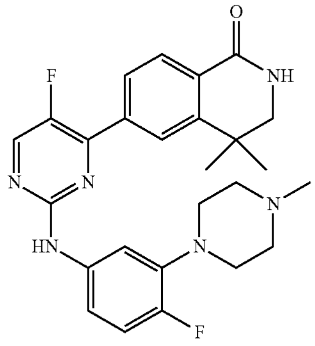 [SMILES: CN1CCN(c2cc(Nc3ncc(F)c(-c4ccc5c(c4)C(C)(C)CNC5=O)n3)ccc2F)CC1] |
| 73 | 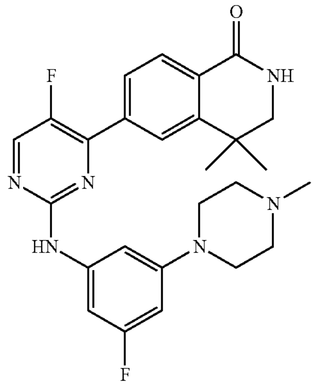 [SMILES: CN1CCN(c2cc(F)cc(Nc3ncc(F)c(-c4ccc5c(c4)C(C)(C)CNC5=O)n3)c2)CC1] |
| 74 | 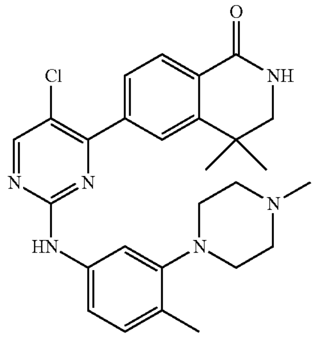 [SMILES: Cc1ccc(Nc2ncc(Cl)c(-c3ccc4c(c3)C(C)(C)CNC4=O)n2)cc1N1CCN(C)CC1] |
| 75 | 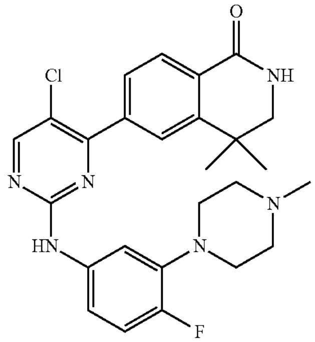 [SMILES: CN1CCN(c2cc(Nc3ncc(Cl)c(-c4ccc5c(c4)C(C)(C)CNC5=O)n3)ccc2F)CC1] |
-continued
| Comp. No. | Comp. Structure |
| --- | --- |
| 76 | 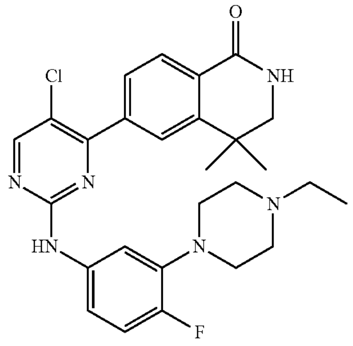 |
| 77 | 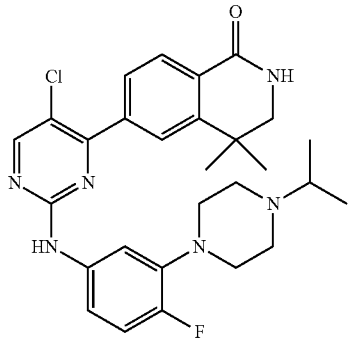 [SMILES: CC(C)N1CCN(c2cc(Nc3ncc(Cl)c(-c4ccc5c(c4)C(C)(C)CNC5=O)n3)ccc2F)CC1] |
| 78 | 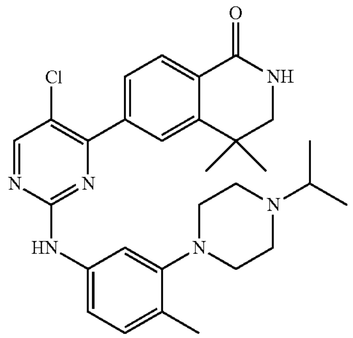 [SMILES: Cc1ccc(Nc2ncc(Cl)c(-c3ccc4c(c3)C(C)(C)CNC4=O)n2)cc1N1CCN(C(C)C)CC1] |
| 79 | 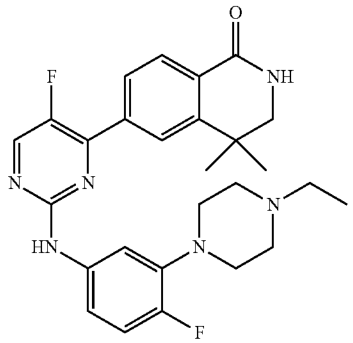 [SMILES: CCN1CCN(c2cc(Nc3ncc(F)c(-c4ccc5c(c4)C(C)(C)CNC5=O)n3)ccc2F)CC1] |

-continued
| Comp. No. | Comp. Structure |
|---|---|
| 80 | 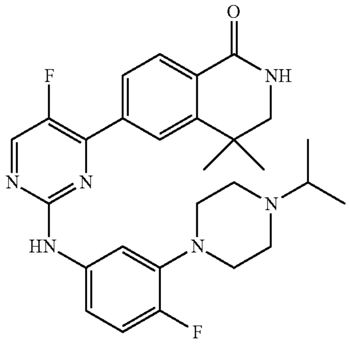 |
| 81 | 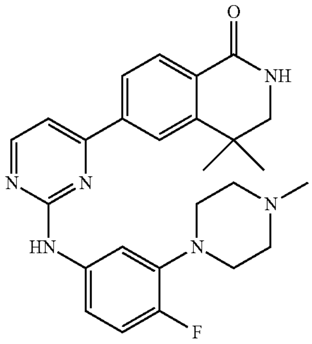 [SMILES: CN1CCN(c2cc(Nc3nccc(-c4ccc5c(c4)C(C)(C)CNC5=O)n3)ccc2F)CC1] |
| 82 | 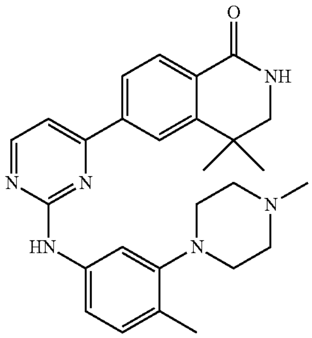 [SMILES: Cc1ccc(Nc2nccc(-c3ccc4c(c3)C(C)(C)CNC4=O)n2)cc1N1CCN(C)CC1] |
| 83 | 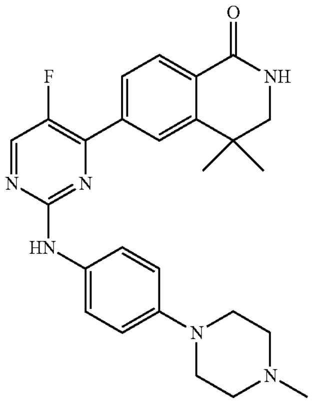 [SMILES: CN1CCN(c2ccc(Nc3ncc(F)c(-c4ccc5c(c4)C(C)(C)CNC5=O)n3)cc2)CC1] |
-continued
| Comp. No. | Comp. Structure |
|---|---|
| 84 | 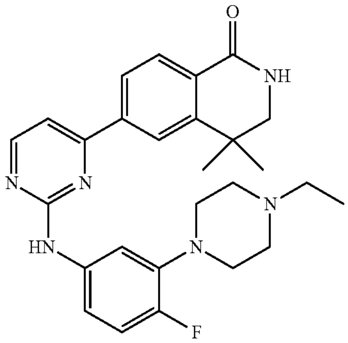 [SMILES: CCN1CCN(c2cc(Nc3nccc(-c4ccc5c(c4)C(C)(C)CNC5=O)n3)ccc2F)CC1] |
| 85 | 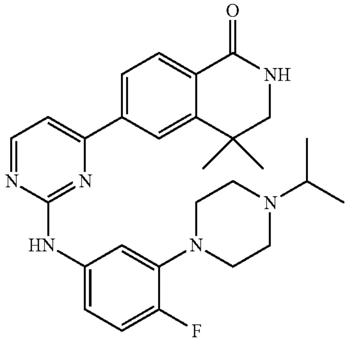 [SMILES: CC(C)N1CCN(c2cc(Nc3nccc(-c4ccc5c(c4)C(C)(C)CNC5=O)n3)ccc2F)CC1] |
| 86 | 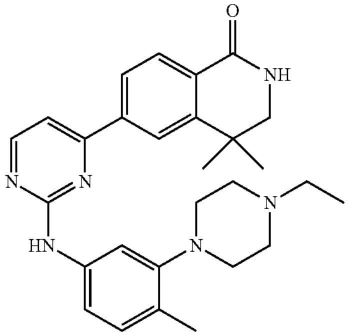 [SMILES: CCN1CCN(c2cc(Nc3nccc(-c4ccc5c(c4)C(C)(C)CNC5=O)n3)ccc2C)CC1] |
| 87 | 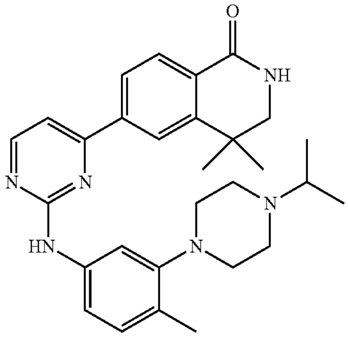 [SMILES: Cc1ccc(Nc2nccc(-c3ccc4c(c3)C(C)(C)CNC4=O)n2)cc1N1CCN(C(C)C)CC1] |

-continued
| Comp. No. | Comp. Structure |
| --- | --- |
| 88 | 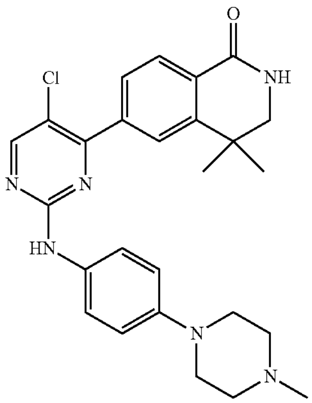 [SMILES: CN1CCN(c2ccc(Nc3ncc(Cl)c(-c4ccc5c(c4)C(C)(C)CNC5=O)n3)cc2)CC1] |
| 89 | 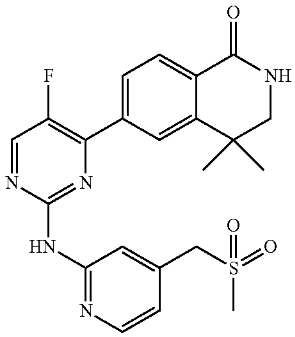 [SMILES: CC1(C)CNC(=O)c2ccc(-c3nc(Nc4cc(CS(C)(=O)=O)ccn4)ncc3F)cc21] |
| 90 | 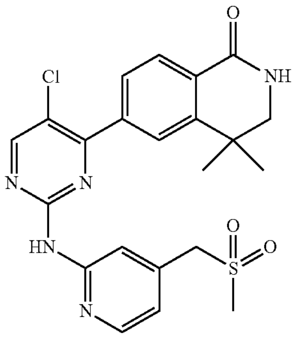 [SMILES: CC1(C)CNC(=O)c2ccc(-c3nc(Nc4cc(CS(C)(=O)=O)ccn4)ncc3Cl)cc21] |
| 91 | 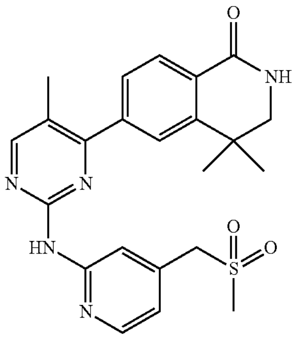 [SMILES: Cc1cnc(Nc2cc(CS(C)(=O)=O)ccn2)nc1-c1ccc2c(c1)C(C)(C)CNC2=O] |
-continued
| Comp. No. | Comp. Structure |
| --- | --- |
| 92 | 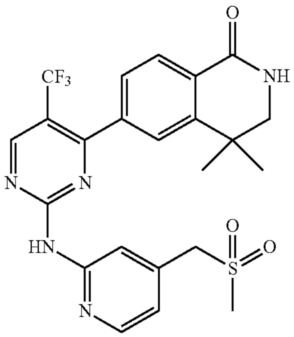 [SMILES: CC1(C)CNC(=O)c2ccc(-c3nc(Nc4cc(CS(C)(=O)=O)ccn4)ncc3C(F)(F)F)cc21] |
| 93 | 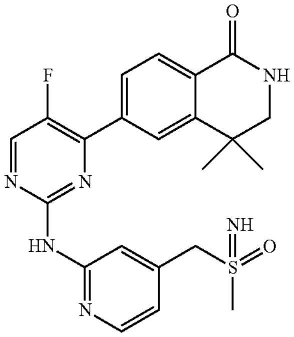 [SMILES: CC1(C)CNC(=O)c2ccc(-c3nc(Nc4cc(CS(C)(=N)=O)ccn4)ncc3F)cc21] |
| 94 | 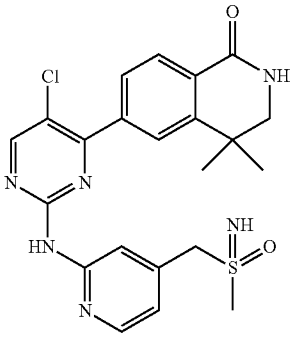 [SMILES: CC1(C)CNC(=O)c2ccc(-c3nc(Nc4cc(CS(C)(=N)=O)ccn4)ncc3Cl)cc21] |
| 95 | 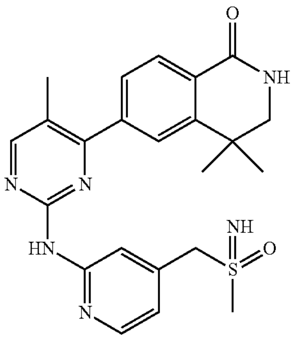 [SMILES: Cc1cnc(Nc2cc(CS(C)(=N)=O)ccn2)nc1-c1ccc2c(c1)C(C)(C)CNC2=O] |

-continued
| Comp. No. | Comp. Structure |
|---|---|
| 96 | 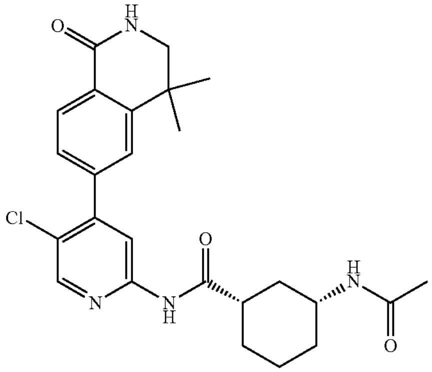 [SMILES: CC(=O)N[C@@H]1CCC[C@H](C(=O)Nc2cc(-c3ccc4c(c3)C(C)(C)CNC4=O)c(Cl)cn2)C1] |
| 97 | 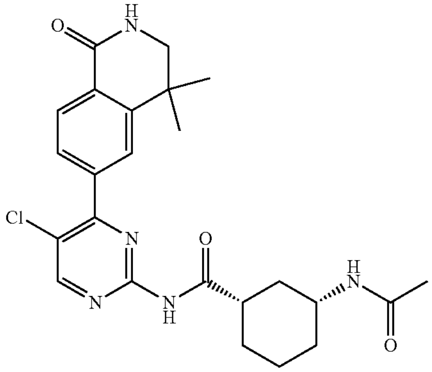 [SMILES: CC(=O)N[C@@H]1CCC[C@H](C(=O)Nc2ncc(Cl)c(-c3ccc4c(c3)C(C)(C)CNC4=O)n2)C1] |
| 98 | 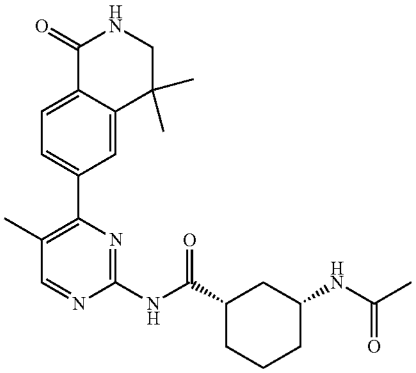 [SMILES: CC(=O)N[C@@H]1CCC[C@H](C(=O)Nc2ncc(C)c(-c3ccc4c(c3)C(C)(C)CNC4=O)n2)C1] |
| 99 | 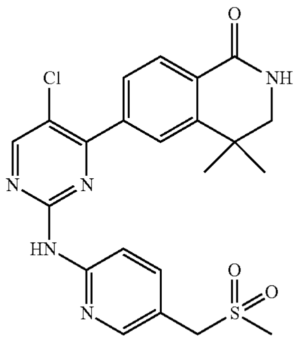 |
-continued
| Comp. No. | Comp. Structure |
|---|---|
| 100 | 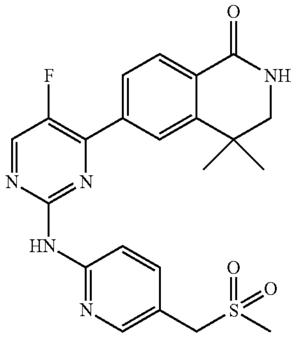 |
| 101 | 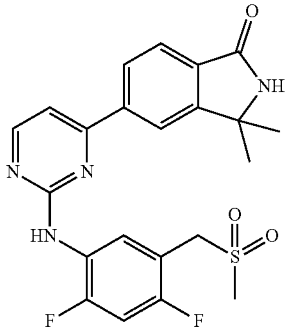 [SMILES: CC1(C)NC(=O)c2ccc(-c3ccnc(Nc4cc(CS(C)(=O)=O)c(F)cc4F)n3)cc21] |
| 102 | 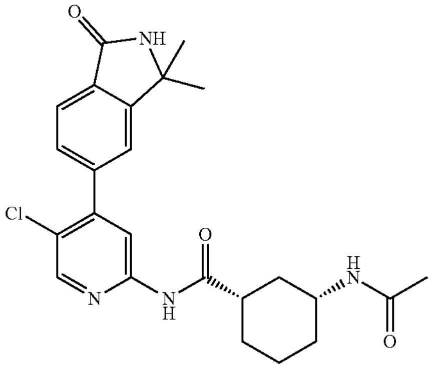 [SMILES: CC(=O)N[C@@H]1CCC[C@H](C(=O)Nc2cc(-c3ccc4c(c3)C(C)(C)NC4=O)c(Cl)cn2)C1] |
| 103 | 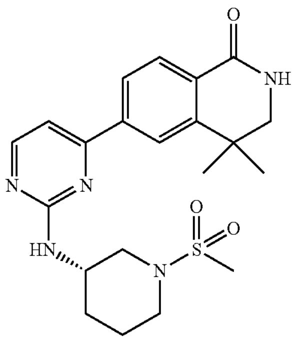 [SMILES: CC1(C)CNC(=O)c2ccc(-c3ccnc(N[C@H]4CCCN(S(C)(=O)=O)C4)n3)cc21] |

-continued

| Comp. No. | Comp. Structure |
|---|---|
| 104 | 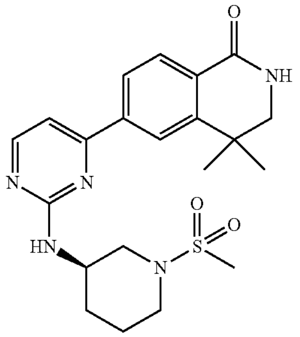 [SMILES: CC1(C)CNC(=O)c2ccc(-c3ccnc(N[C@@H]4CCCN(S(C)(=O)=O)C4)n3)cc21] |
| 105 | 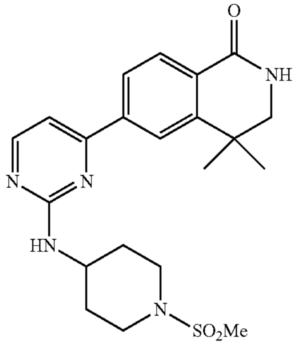 [SMILES: CC1(C)CNC(=O)c2ccc(-c3ccnc(NC4CCN(S(C)(=O)=O)CC4)n3)cc21] |
| 106 | 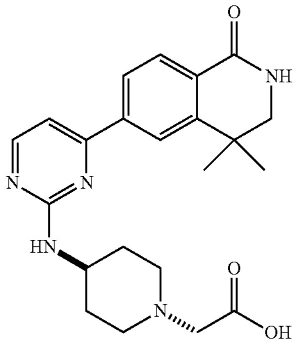 |
| 107 | 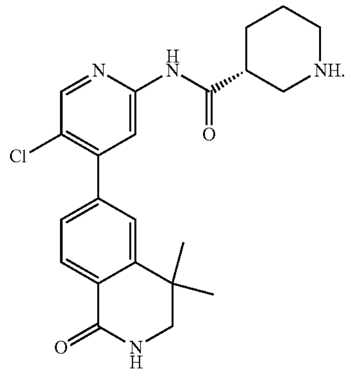 [SMILES: CC1(C)CNC(=O)c2ccc(-c3cc(NC(=O)[C@@H]4CCCNC4)ncc3Cl)cc21] |

8. A pharmaceutical composition, comprising the kinase inhibitor of claim 1, and a pharmaceutically acceptable diluent or carrier, and optionally one or more other active ingredients.

9. A method of treating a disease relating to CDK9 and/or CDK9 mutations, comprising administering the kinase inhibitor of claim 1 to a subject having said disease.

10. A method of treating a disease selected from the group consisting of hyperproliferative diseases, virus induced infectious diseases and cardiovascular diseases, comprising administering the kinase inhibitor of claim 1 to a subject having said disease.

11. The method of claim 10, wherein the hyperproliferative disease is cancer.

12. The method of claim 11, wherein the cancer is selected from the group consisting of leukemia, liver cancer, ovarian cancer, cervical cancer, colorectal cancer, gastrointestinal stromal tumor, and lymphoma.

* * * * *